United States Patent
Kugimiya et al.

(10) Patent No.: US 7,842,692 B2
(45) Date of Patent: Nov. 30, 2010

(54) AZAINDOLE DERIVATIVE HAVING PGD2 RECEPTOR ANTAGONISTIC ACTIVITY

(75) Inventors: Akira Kugimiya, Osaka (JP); Itsuo Makino, Osaka (JP); Naohiro Onodera, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 307 days.

(21) Appl. No.: 11/989,132

(22) PCT Filed: Jul. 20, 2006

(86) PCT No.: PCT/JP2006/314346
§ 371 (c)(1),
(2), (4) Date: Mar. 26, 2008

(87) PCT Pub. No.: WO2007/010965
PCT Pub. Date: Jan. 25, 2007

(65) Prior Publication Data
US 2009/0197881 A1    Aug. 6, 2009

(30) Foreign Application Priority Data
Jul. 22, 2005  (JP) .............................. 2005-212910
Dec. 16, 2005  (JP) .............................. 2005-362754

(51) Int. Cl.
C07D 471/04 (2006.01)
A61K 31/5377 (2006.01)
A61K 31/437 (2006.01)

(52) U.S. Cl. .................... 514/234.5; 514/300; 544/127; 546/113

(58) Field of Classification Search ............. 514/234.5, 514/300; 546/113; 544/127
See application file for complete search history.

(56) References Cited

U.S. PATENT DOCUMENTS

| | | | |
|---|---|---|---|
| 2005/0004096 A1 | 1/2005 | Torisu et al. | |
| 2005/0004097 A1 | 1/2005 | Torisu et al. | |
| 2005/0096376 A1 | 5/2005 | Sundermann et al. | |
| 2005/0171143 A1 | 8/2005 | Tanimoto et al. | |
| 2005/0272756 A1 | 12/2005 | Leblanc et al. | |

FOREIGN PATENT DOCUMENTS

| | | |
|---|---|---|
| EP | 1 424 325 | 6/2004 |
| EP | 1 424 335 | 6/2004 |
| EP | 1 505 061 | 2/2005 |
| GB | 2 407 318 | 4/2005 |
| WO | 01/79169 | 10/2001 |
| WO | 02/094830 | 11/2002 |
| WO | 03/022813 | 3/2003 |
| WO | 03/022814 | 3/2003 |
| WO | 03/062200 | 7/2003 |
| WO | 03/066047 | 8/2003 |
| WO | 03/097042 | 11/2003 |
| WO | 03/097598 | 11/2003 |
| WO | 03/101961 | 12/2003 |
| WO | 03/101981 | 12/2003 |
| WO | 2004/007451 | 1/2004 |
| WO | 2004/039807 | 5/2004 |
| WO | 2004/103970 | 12/2004 |
| WO | 2004/106302 | 12/2004 |
| WO | 2004/111047 | 12/2004 |
| WO | 2005/009958 | * 2/2005 |
| WO | 2005/019171 | 3/2005 |
| WO | 2005/019208 | 3/2005 |
| WO | 2005/040112 | 5/2005 |
| WO | 2005/040114 | 5/2005 |
| WO | 2005/044260 | 5/2005 |
| WO | 2005/054232 | 6/2005 |
| WO | 2005/056527 | 6/2005 |

OTHER PUBLICATIONS

Robert A. Coleman et al., "VIII. International Union of Pharmacology Classification of Prostanoid Receptors: Properties, Distribution, and Structure of the Receptors and Their Subtypes", Pharmacological Reviews, vol. 46, No. 2, pp. 205-229, 1994.
International Search Report issued Sep. 5, 2006 in the International (PCT) Application PCT/JP2006/314346 of which the present application is the U.S. National Stage.

* cited by examiner

*Primary Examiner*—D. Margaret Seaman
*Assistant Examiner*—Niloofar Rahmani
(74) *Attorney, Agent, or Firm*—Wenderoth, Lind & Ponack, L.L.P.

(57) ABSTRACT

The present invention creates an azaindole derivative having DP receptor antagonistic activity and a pharmaceutical composition comprising the said compound as an active ingredient, and further providing a therapeutic agent for treating allergic diseases.

A compound of the general formula (I)

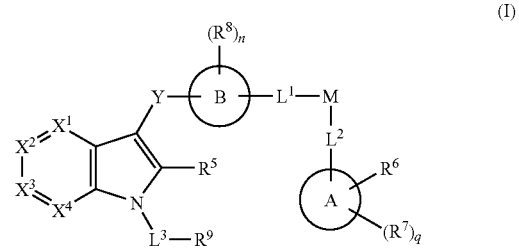

wherein the ring A is an aromatic carbocyclic ring etc.; the ring B is a 3- to 8-membered nitrogen-containing non-aromatic heterocyclic ring etc.; the formula of —$X^1$=$X^2$—$X^3$=$X^4$— is a formula of —C($R^1$)=C($R^2$)—C($R^3$)=N— etc.; $R^1$, $R^2$, $R^3$, $R^4$ and $R^5$ are independently a hydrogen atom or a halogen atom etc.; $R^6$ is optionally substituted C1-C6 alkyloxy etc.; $R^7$ is independently a halogen atom etc.; $R^8$ is optionally substituted C1-C6 alkyl etc.; $R^9$ is carboxy etc.; M is sulfonyl etc.; Y is a single bond etc.; $L^1$, $L^2$ and $L^3$ are a single bond or alkylene optionally containing one or two heteroatoms etc.; n is 0 etc.; q is 0 etc.; a pharmaceutically acceptable salt or hydrate thereof.

11 Claims, No Drawings

AZAINDOLE DERIVATIVE HAVING PGD2 RECEPTOR ANTAGONISTIC ACTIVITY

TECHNICAL FIELD

This invention relates to an azaindole derivative having DP receptor antagonistic activity and a medicinal use thereof.

BACKGROUND ART

Prostaglandin D2(PGD2) is a metabolic product of arachidonic acid through PGG2 and PGH2, and known to have various potent physiological activities. For example, in non-patent literature 1 it is described that PGD2 is involved in sleeping and secretion of hormones in central nervous system, and in inhibiting activity of platelet aggregation, contraction of bronchial smooth muscle, vasodilation and constriction of a blood vessel etc. in peripheral system. Moreover, PGD2 is considered to be involved in forming pathological condition of an allergic disease such as bronchial asthma since it is a major metabolic product of arachidonic acid produced from a mast cell, and has a potent bronchoconstricting effect, causing an increase of blood vessel permeability and migration of inflammatory cell such as an eosinophil.

A DP receptor (also called DP1 receptor) or CRTH2 receptor (also called DP2 receptor) is known as a receptor of PGD2 but these are completely different receptors. In Patent literatures 1-9 indole derivatives having a DP receptor antagonistic activity is disclosed, and in Patent literatures 10-21 indole derivatives having a CRTH2 receptor antagonistic activity is disclosed Also, indole derivatives having inhibitory activity against noradrenaline re-uptake are disclosed in Patent literature 22.

Patent literature 1: WO 2005/056527 Pamphlet
Patent literature 2: WO 2004/111047 Pamphlet
Patent literature 3: WO 2004/103970 Pamphlet
Patent literature 4: WO 2004/039807 Pamphlet
Patent literature 5: WO 2003/062200 Pamphlet
Patent literature 6: WO 2002/094830 Pamphlet
Patent literature 7: WO 2001/079169 Pamphlet
Patent literature 8: WO 2003/022814 Pamphlet
Patent literature 9: WO 2003/022813 Pamphlet
Patent literature 10: WO 2003/097598 Pamphlet
Patent literature 11: WO 2003/097042 Pamphlet
Patent literature 12: WO 2005/019171 Pamphlet
Patent literature 13: WO 2004/106302 Pamphlet
Patent literature 14: WO 2004/007451 Pamphlet
Patent literature 15: WO 2003/101981 Pamphlet
Patent literature 16: WO 2003/101961 Pamphlet
Patent literature 17: WO 2003/066047 Pamphlet
Patent literature 18: WO 2005/040112 Pamphlet
Patent literature 19: WO 2005/040114 Pamphlet
Patent literature 20: WO 2005/044260 Pamphlet
Patent literature 21: GB 2407318A Pamphlet
Patent literature 22: WO 2005/019208 Pamphlet
Non-patent literature 1: Pharmacol. Review, Vol. 46, page 205-229 (1994)

DISCLOSURE OF INVENTION

Problem to be Solved

The present invention provides a novel compound having DP receptor antagonistic activity and a pharmaceutical composition comprising the said compound as an active ingredient. The said pharmaceutical composition is useful as a therapeutic agent for treating allergic diseases.

Means for Solving Problem

The present inventors have found that the azaindole derivative shown below has a potent DP receptor antagonistic activity and the pharmaceutical composition comprising the said compound as an active ingredient is useful as a therapeutic agent for treating allergic diseases.

The present invention relates to 1) a compound of the general formula (I):

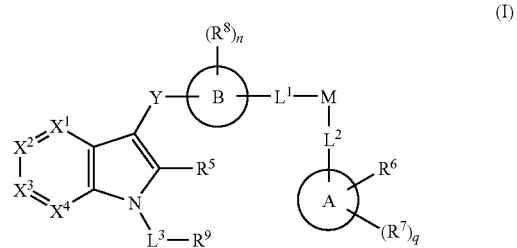

wherein the ring A is an aromatic carbocyclic ring or an aromatic heterocyclic ring;

the ring B is a 3- to 8-membered nitrogen-containing non-aromatic heterocyclic ring or a 3- to 8-membered nitrogen-containing aromatic heterocyclic ring;

the formula of $-X^1=X^2-X^3=X^4-$ is a formula of $-N=C(R^2)-C(R^3)=C(R^4)-$, $-C(R^1)=N-C(R^3)=C(R^4)-$, $-C(R^1)=C(R^2)-N=C(R^4)-$ or $-C(R^1)=C(R^2)-C(R^3)=N-$;

$R^1$, $R^2$, $R^3$, $R^4$ and $R^5$ are independently a hydrogen atom, a halogen atom, optionally substituted alkyl, optionally substituted alkenyl, optionally substituted alkynyl, optionally substituted cyloalkyl, optionally substituted cyloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkynylsulfonyl, optionally substituted alkynylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, amino, acyl, optionally substituted alkyloxycarbonyl, optionally substituted alkenyloxycarbonyl, optionally substituted alkynyloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfony, optionally substituted arylsulfonyoxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group;

$R^6$ is a hydrogen atom, optionally substituted C1-C6 alkyloxy, optionally substituted C2-C6 alkenyloxy, optionally substituted C2-C6 alkynyloxy, optionally substituted C3-C6 cycloalkyloxy, optionally substituted C3-C6 cycloalkenyloxy, optionally substituted aryloxy, optionally substituted heteroaryloxy, optionally substituted C1-C6 alkylthio, optionally substituted C2-C6 alkenylthio, optionally substituted C2-C6 alkynylthio, optionally substituted C3-C6 cycloalkylthio, optionally substituted C3-C6 cycloalkenylthio, optionally substituted arylthio, or optionally substituted heteroarylthio;

$R^7$ is independently a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or optionally substituted non-aromatic heterocyclic group;

$R^8$ is independently a halogen atom, optionally substituted alkyl, optionally substituted alkenyl, optionally substituted alkynyl, optionally substituted cycloalkyl, optionally substituted alkyloxy, oxo, optionally substituted aryl, optionally substituted heteroaryl or optionally substituted non-aromatic heterocyclic group;

$R^9$ is carboxy, optionally substituted alkyloxycarbonyl, optionally substituted carbamoyl or carboxy equivalent;

M is carbonyl or sulfonyl;

Y is a single bond, optionally substituted alkylene optionally containing one or two heteroatom(s), an oxygen atom, a sulfur atom or —N($R^{10}$)—;

$L^1$, $L^2$ and $L^3$ are independently a single bond, optionally substituted alkylene optionally containing one or two heteroatom(s), optionally substituted alkenylene optionally containing one or two heteroatom(s), optionally substituted alkynylene optionally containing one or two heteroatom(s) or —N($R^{11}$)—;

$R^{10}$ and $R^{11}$ are independently a hydrogen atom, optionally substituted alkyl, optionally substituted alkenyl, optionally substituted alkynyl, optionally substituted cycloalkyl, acyl, optionally substituted alkyloxy, optionally substituted aryl, optionally substituted heteroaryl, or optionally substituted non-aromatic heterocyclic group;

n is 0, 1 or 2; and q is 0, 1, 2 or 3;

a pharmaceutically acceptable salt or hydrate thereof, 2) a compound of 1) wherein the formula of —$X^1$=$X^2$—$X^3$=$X^4$— is a formula of —N=C($R^2$)—C($R^3$)=C($R^4$)—, a pharmaceutically acceptable salt or hydrate thereof, 3) a compound of 1) wherein the formula of —$X^1$=$X^2$—$X^3$=$X^4$— is a formula of —C($R^1$)=N—C($R^3$)=C($R^4$)—, a pharmaceutically acceptable salt or hydrate thereof, 4) a compound of 1) wherein the formula of —$X^1$=$X^2$—$X^3$=$X^4$— is a formula of —C($R^1$)=C($R^2$)—N=C($R^4$)—, a pharmaceutically acceptable salt or hydrate thereof, 5) a compound of 1) wherein the formula of —$X^1$=$X^2$—$X^3$=$X^4$— is a formula of —C($R^1$)=C($R^2$)—C($R^3$)=N—, a pharmaceutically acceptable salt or hydrate thereof, 6) a compounds of any of 1) to 5) wherein $R^6$ is optionally substituted C1-C6 alkyloxy, optionally substituted C1-C6 alkylthio, optionally substituted C3-C6 cycloalkyloxy, optionally substituted C3-C6 cycloalkylthio, optionally substituted aryloxy or optionally substituted arylthio, a pharmaceutically acceptable salt or hydrate thereof, 7) a compound of any of 1) to 6) wherein the ring A is a benzene or pyridine ring, a pharmaceutically acceptable salt or hydrate thereof, 8) a compound of any of 1) to 7) wherein $R^5$ is a hydrogen atom, a halogen atom, optionally substituted alkyl or optionally substituted aryl, a pharmaceutically acceptable salt or hydrate thereof, 9) a compound of any of 1) to 8) wherein Y is a single bond or optionally substituted alkylene optionally containing one or two heteroatom(s), a pharmaceutically acceptable salt or hydrate thereof, 10) a compound of any of 1) to 9), wherein $R^9$ is carboxy and $L^3$ is optionally substituted alkylene optionally containing one or two heteroatom(s), pharmaceutically acceptable salt or hydrate thereof, 11) a compound of any of 1) to 10) wherein M is sulfonyl, a pharmaceutically acceptable salt or hydrate thereof, 12) a compound of any of 1) to 12) wherein $L^1$ and $L^2$ is a single bond, the ring B is a formula of

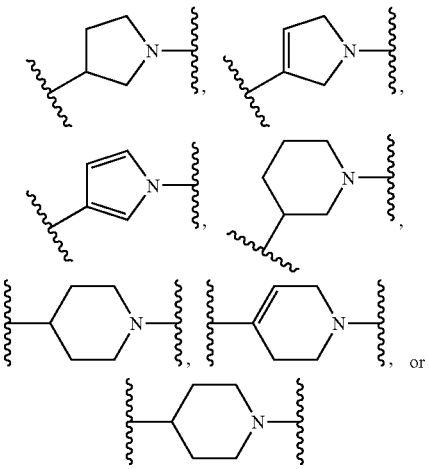

and n is 0, a pharmaceutically acceptable salt or hydrate thereof;

13) a compound of the general formula (II):

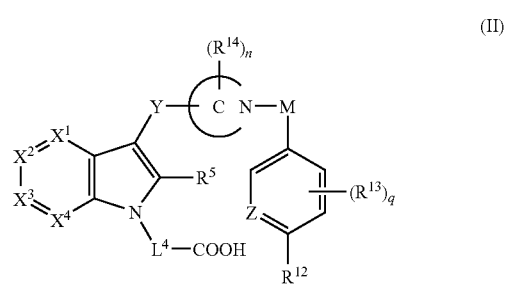

wherein the ring C is a ring of the formula of

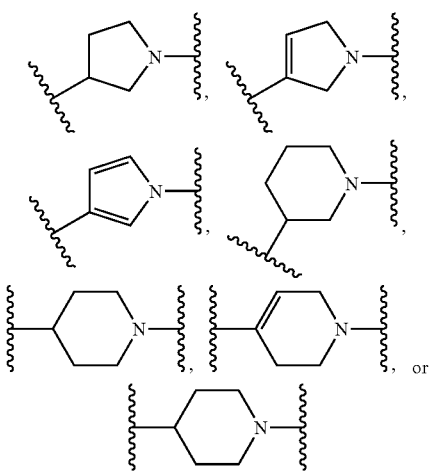

the formula of —$X^1$=$X^2$—$X^3$=$X^4$— is a formula of —N=C($R^2$)—C($R^3$)=C($R^4$)—, —C($R^1$)=N—C($R^3$)=C($R^4$)—, —C($R^1$)=C($R^2$)—N=C($R^4$)— or —C($R^1$)=C($R^2$)—C($R^3$)=N—;

$R^1$, $R^2$, $R^3$, $R^4$ and $R^5$ are independently a hydrogen atom, halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or optionally substituted non-aromatic heterocyclic group;

$R^{12}$ is optionally substituted C1-C6 alkyloxy, optionally substituted C2-C6 alkenyloxy, optionally substituted C2-C6 alkynyloxy, optionally substituted C1-C6 alkylthio, optionally substituted C2-C6 alkenylthio, optionally substituted C2-C6 alkynylthio, optionally substituted C3-C6 cycloalkyloxy, optionally substituted C3-C6 cycloalkylthio, optionally substituted aryloxy or optionally substituted arylthio;

$R^{13}$ is independently a halogen atom, optionally substituted alkyl, optionally substituted cycloalkyl, optionally substituted amino, acyl, optionally substituted alkyloxycarbonyl, optionally substituted carbamoyl, optionally substituted sulfamoyl, cyano, nitro, optionally substituted aryl, optionally substituted arylsulfonyloxy, optionally substituted heteroaryl or optionally substituted non-aromatic heterocyclic group;

$R^{14}$ is independently optionally substituted alkyl, optionally substituted alkenyl, optionally substituted alkynyl, oxo, optionally substituted aryl, optionally substituted heteroaryl, or optionally substituted non-aromatic heterocyclic group;

M is carbonyl or sulfoyl;

Y and $L^4$ are independently a single bond or optionally substituted alkylene optionally containing one or two heteroatom(s);

Z is CH, C($R^{13}$) or N;

n is 0, 1 or 2; and q is 0, 1, 2 or 3;

a pharmaceutically acceptable salt or hydrate thereof, 14) a compound of 13) wherein the formula of —$X^1$=$X^2$—$X^3$=$X^4$— is a formula of —C($R^1$)=N—C($R^3$)=C($R^4$)—, a pharmaceutically acceptable salt or hydrate thereof, 15) a compound of 13) wherein the formula of —$X^1$=$X^2$—$X^3$=$X^4$— is a formula of —C($R^1$)=C($R^2$)—N=C($R^4$)—, a pharmaceutically acceptable salt or hydrate thereof, 16) a compound of 13) wherein the formula of —$X^1$=$X^2$—$X^3$=$X^4$— is a formula of —C($R^1$)=C($R^2$)—C($R^3$)=N—, a pharmaceutically acceptable salt or hydrate thereof, 17) a compound of 13) or 16) wherein $R^1$, $R^2$ and $R^5$ are independently a hydrogen atom, a halogen atom or optionally substituted alkyl, a pharmaceutically acceptable salt or hydrate thereof, 18) a compound of 17) wherein $R^1$, $R^2$ and $R^5$ are hydrogen atoms, a pharmaceutically acceptable salt or hydrate thereof, 19) a compound of any of 13) to 18) wherein $R^3$ is a hydrogen atom, a halogen atom, optionally substituted alkyl, optionally substituted alkyloxy, optionally substituted amino, optionally substituted carbamoyl, optionally substituted aryl, optionally substituted heteroaryl or optionally substituted non-aromatic heterocyclic group, a pharmaceutically acceptable salt or hydrate thereof, 20) a compound of any of 13) or 16) to 19) wherein $R^3$ is a hydrogen atom, a halogen atom, optionally substituted alkyloxy, optionally substituted amino, optionally substituted aryl, optionally substituted heteroaryl or optionally substituted non-aromatic heterocyclic group;

a pharmaceutically acceptable salt or hydrate thereof, 21) a compound of any of 13) to 20) wherein $R^{12}$ is optionally substituted C1-C6 alkyl or optionally substituted C1-C6 alkylthio;

a pharmaceutically acceptable salt or hydrate thereof, 22) a compound of any of 13) to 21) wherein $R^{13}$ is a halogen atom or optionally substituted alkyl and q is 0 or 1;

a pharmaceutically acceptable salt or hydrate thereof, 23) a compound of any of 13) to 22) wherein M is sulfonyl, a pharmaceutically acceptable salt or hydrate thereof, 24) a compound of any of 13) to 23) wherein $R^{14}$ is alkyl and n is 0 or 1, a pharmaceutically acceptable salt or hydrate thereof, 25) a compound of any of 13) to 24) wherein Y is a single bond or optionally substituted alkylene, a pharmaceutically acceptable salt or hydrate thereof, 26) a compound of any of 13) to 25) wherein $L^4$ is optionally substituted alkylene, a pharmaceutically acceptable salt or hydrate thereof, 27) a compound of the general formula (III):

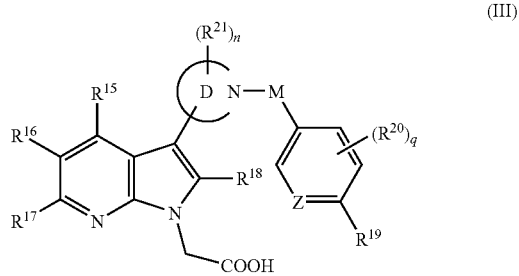

(III)

wherein the ring D is a formula of

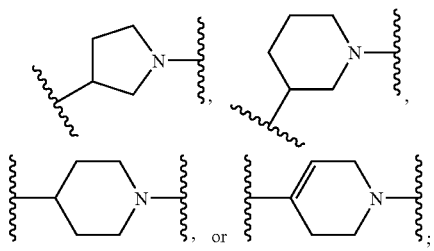

$R^{15}$, $R^{16}$ and $R^{18}$ are independently a hydrogen atom, a halogen atom, optionally substituted alkyl, optionally substituted alkyloxy, optionally substituted alkylthio, optionally substituted alkylsulfinyl, optionally substituted alkylsulfonyl, optionally substituted amino, cyano, nitro, optionally substituted aryl, optionally substituted heteroaryl or optionally substituted non-aromatic heterocyclic group;

$R^{17}$ is a hydrogen atom, a halogen atom, optionally substituted alkyl, optionally substituted alkenyl, optionally substituted alkynyl, optionally substituted cyloalkyl, optionally substituted cyloalkenyl, hydroxy, optionally substituted alkyloxy, optionally substituted alkenyloxy, optionally substituted alkynyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group;

$R^{19}$ is optionally substituted C1-C6 alkyloxy, optionally substituted C2-C6 alkenyloxy, optionally substituted C2-C6 alkynyloxy, optionally substituted C1-C6 alkylthio, optionally substituted C2-C6 alkenylthio, optionally substituted C2-C6 alkynylthio, optionally substituted C3-C6 cycloalkyloxy, optionally substituted C3-C6 cycloalkyltho, optionally substituted aryloxy or optionally substituted arylthio;

$R^{20}$ is independently a halogen atom, optionally substituted alkyl, optionally substituted cyloalkyl, optionally substituted amino, optionally substituted alkyloxycarbonyl, optionally substituted carbamoyl, optionally substituted sulfamoyl, cyano, nitro, optionally substituted aryl, optionally substituted arylsulfonyloxy, optionally substituted heteroaryl or an optionally substituted non-aromatic heterocyclic group;

$R^{21}$ is independently optionally substituted alkyl, optionally substituted alkenyl, optionally substituted alkynyl, oxo, optionally substituted aryl, optionally substituted heteroaryl, or an optionally substituted non-aromatic heterocyclic group;

M is carbonyl or sulfonyl;

Z is CH, $C(R^{20})$, or N;

n is 0, 1 or 2 and q is 0, 1, 2 or 3;

a pharmaceutically acceptable salt or hydrate thereof, 28) a compound of 27) wherein $R^{17}$ is a hydrogen atom, a halogen atom, optionally substituted alkyl, optionally substituted alkyloxy, optionally substituted amino, optionally substituted carbamoyl, optionally substituted aryl, optionally substituted heteroaryl or optionally substituted non-aromatic heterocyclic group;

a pharmaceutically acceptable salt or hydrate thereof, 29) a compound of 27) or 28) wherein $R^{17}$ is a hydrogen atom, a halogen atom, optionally substituted alkyloxy, optionally substituted amino, optionally substituted aryl, optionally substituted heteroaryl or optionally substituted non-aromatic heterocyclic group;

a pharmaceutically acceptable salt or hydrate thereof, 30) a compound of any of 27) to 29) wherein $R^{15}$, $R^{16}$ and $R^{18}$ are hydrogen atoms, a pharmaceutically acceptable salt or hydrate thereof, 31) a compound of any of 27) to 30) wherein $R^{19}$ is optionally substituted C1-C6 alkyl or optionally substituted C1-C6 alkylthio, a pharmaceutically acceptable salt or hydrate thereof, 32) a compound of any of 27) to 31) wherein $R^{20}$ is optionally substituted alkyl or optionally substituted alkyloxy and q is 0 or 1, a pharmaceutically acceptable salt or hydrate thereof, 33) a compound of any of 27) to 32) wherein M is sulfonyl, a pharmaceutically acceptable salt or hydrate thereof, 34) a compound of any of 27) to 33) wherein the ring D is a formula of

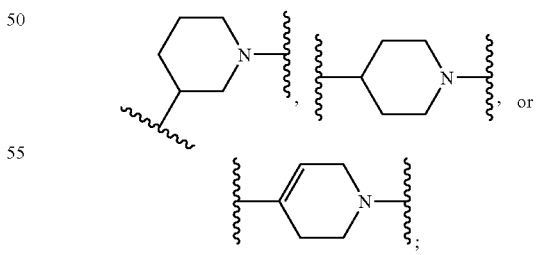

a pharmaceutically acceptable salt or hydrate thereof, 35) a compound of any of 27) to 34) wherein n is 0, a pharmaceutically acceptable salt or hydrate thereof, 36) a pharmaceutical composition comprising the compound of any of 1) to 35), pharmaceutically acceptable salt or hydrate thereof, 37) a pharmaceutical composition of 36) which is a DP receptor antagonist;

38) a pharmaceutical composition of 36) which is a therapeutic agent for allergy, 39) a pharmaceutical composition of 38) wherein the therapeutic agent for allergy is a medicine for asthma, 40) a method for treating a disease related to DP receptor characterized by administration of the compound of any of 1) to 35), pharmaceutically acceptable salt or hydrate thereof, 41) a method of 40) wherein the disease related to DP receptor is asthma, 42) use of the compound of any of 1) to 35), pharmaceutically acceptable salt or hydrate thereof, in the manufacturing of a therapeutic agent for treating diseases related to DP receptor, 43) use of the compound of 42), pharmaceutically acceptable salt or hydrate thereof wherein the disease related to DP receptor is asthma, 44) a compound of the general formula:

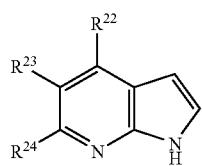

(IV)

wherein $R^{22}$ and $R^{23}$ are independently a hydrogen atom, a halogen atom, optionally substituted alkyl or optionally substituted aryl or optionally substituted heteroaryl;

$R^{24}$ is optionally substituted alkoxy, optionally substituted alkylthio, optionally substituted carbamoyl or optionally substituted non-aromatic heterocyclic group;

a pharmaceutically acceptable salt or hydrate thereof, and 45) a compound of 44) wherein $R^{23}$ is optionally substituted alkoxy, a pharmaceutically acceptable salt or hydrate thereof.

The present invention also includes the following inventions;

(1) a compound of the general formula (I-b):

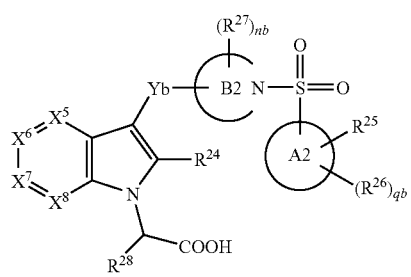

(I-b)

wherein the ring A2 is an aromatic carbocyclic ring or an aromatic heterocyclic ring;

the ring B2 is a 3- to 8-membered nitrogen-containing heterocyclic ring containing only nitrogen atom as a heteroatom;

the formula of $-X^5=X^6-X^7=X^8-$ is a formula of $-N=C(R^{23b})-C(R^{23c})=C(R^{23d})-$, $-C(R^{23a})=N-C(R^{23c})=C(R^{23d})-$, $-C(R^{23a})=C(R^{23b})-N=C(R^{23d})-$ or $-C(R^{23a})=C(R^{23b})-C(R^{23c})=N-$;

$R^{23a}$, $R^{23b}$, $R^{23c}$, and $R^{23d}$ are independently a hydrogen atom, a halogen atom, optionally substituted alkyl, optionally substituted alkenyl, optionally substituted alkynyl, optionally substituted cyloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, amino, acyl, optionally substituted alkyloxycarbonyl, optionally substituted alkenyloxycarbonyl, optionally substituted alkynyloxycarbonyl, optionally substituted carbamoyl cyano, nitro, optionally substituted aryl, optionally substituted aryloxy, optionally substituted arylthio, optionally substituted arylsulfinyl, optionally substituted arylsulfony, optionally substituted arylsulfonyoxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group;

$R^{24}$ is a hydrogen atom, a halogen atom, optionally substituted alkyl, acyl, optionally substituted aryl or optionally substituted heteroaryl;

$R^{25}$ is a hydrogen atom, optionally substituted C1-C6 alkyloxy, optionally substituted C2-C6 alkenyloxy, optionally substituted C2-C6 alkynyloxy, optionally substituted C3-C6 cycloalkyloxy, optionally substituted C3-C6 cycloalkylmethyloxy, optionally substituted aryloxy, optionally substituted heteroaryloxy, optionally substituted C1-C6 alkylthio, optionally substituted. C2-C6 alkenylthio, optionally substituted C2-C6 alkynylthio, optionally substituted C3-C6 cycloalkylthio, optionally substituted C3-C6 cycloalkylmethylthio, optionally substituted arylthio or optionally substituted heteroarylthio;

$R^{26}$ is independently a halogen atom, optionally substituted alkyl, optionally substituted alkenyl, optionally substituted alkynyl, optionally substituted cyloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfony, optionally substituted arylsulfonyoxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group;

$R^{27}$ is independently C1-C4 alkyl;

$R^{28}$ is a hydrogen atom, a halogen atom or C1-C4 alkyl;

Yb is a single bond or optionally substituted C1-C2 alkylene;

nb is 0, 1 or 2; and qb is 0, 1 or 2;

a pharmaceutically acceptable salt or hydrate thereof, (2) a compound of (1) wherein the formula of $-X^5=X^6-X^7=X^8-$ is a formula of $-N=C(R^{23b})-C(R^{23c})=C(R^{23d})-$, a pharmaceutically acceptable salt or hydrate thereof, (3) a compound of (1) wherein the formula of —$X^5$=$X^6$—$X^7$=$X^8$— is a formula of —C($R^{23a}$)=N—C($R^{23c}$)=C($R^{23d}$)—, a pharmaceutically acceptable salt or hydrate thereof, (4) a compound of (1) wherein the formula of —$X^5$=$X^6$—$X^7$=$X^8$— is a formula of —C($R^{23a}$)=C($R^{23b}$)—N=C($R^{23d}$)—, a pharmaceutically acceptable salt or hydrate thereof, (5) a compound of (1) wherein the formula of —$X^5$=$X^6$—$X^7$=$X^8$— is a formula of —C($R^{23a}$)=C($R^{23b}$)—C($R^{23c}$)=N—, a pharmaceutically acceptable salt or hydrate thereof, (6) a compound of any of (1) to (5) wherein $R^{24}$ is a hydrogen atom, a pharmaceutically acceptable salt or hydrate thereof, (7) a compound of any of (1) to (6) wherein Yb is a single bond, a pharmaceutically acceptable salt or hydrate thereof, (8) a compound of any of (1) to (7) wherein the ring B2 is a formula of

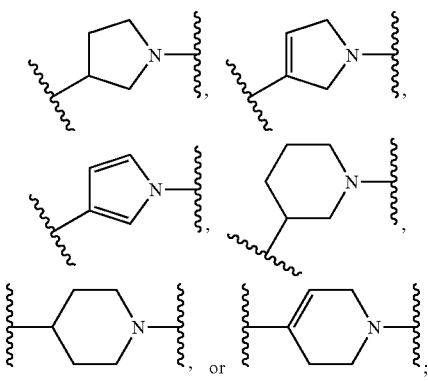

and nb is 0, a pharmaceutically acceptable salt or hydrate thereof, (9) a compound of any of (1) to (8) wherein the ring A2 is a benzene ring, $R^{25}$ is C2-C4 alkyloxy, C1-C4 alkyloxy substituted with a halogen atom, C2-C4 alkylthio, C1-C4 alkylthio substituted with a halogen atom, C3-C4 cycloalkyloxy, C3-C4 cycloalkylmethyloxy or optionally substituted phenoxy;

a pharmaceutically acceptable salt or hydrate thereof,

(10) a compound of the general formula (II-b):

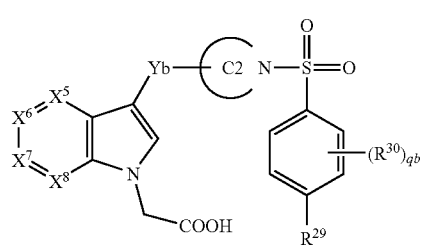

(II-b)

wherein the ring C2 is a formula of

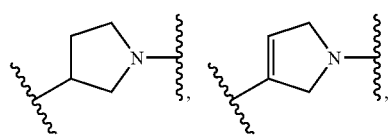

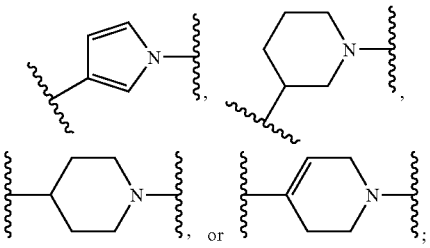

the formula of —$X^5$=$X^6$—$X^7$=$X^8$— is a formula of —N=C($R^{23b}$)—C($R^{23c}$)=C($R^{23d}$)—, —C($R^{23a}$)=N—C($R^{23c}$)=C($R^{23d}$)—, —C($R^{23a}$)=C($R^{23b}$)—N=C($R^{23d}$)— or —C($R^{23a}$)=C($R^{23b}$)—C($R^{23c}$)=N—;

$R^{23a}$, $R^{23b}$, $R^{23c}$ and $R^{23d}$ are independently a hydrogen atom, a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or optionally substituted non-aromatic heterocyclic group;

$R^{29}$ is C2-C4 alkyloxy, C1-C4 alkyloxy substituted with a halogen atom, C2-C4 alkylthio, C1-C4 alkylthio substituted with a halogen atom, C3-C4 cycloalkyloxy, C3-C4 cycloalkylmethyloxy or optionally substituted phenoxy;

$R^{30}$ is independently a halogen atom, optionally substituted alkyl, optionally substituted cycloalkyl, optionally substituted amino, acyl, optionally substituted alkyloxycarbonyl, optionally substituted carbamoyl, cyano, nitro, optionally substituted aryl, optionally substituted arylsulfonyloxy, optionally substituted heteroaryl or optionally substituted non-aromatic heterocyclic group;

Yb is a single bond or optionally substituted C1-C2 alkylene; and qb is 0, 1 or 2;

a pharmaceutically acceptable salt or hydrate thereof,

(11) a compound of (10) wherein the formula of —$X^5$=$X^6$—$X^7$=$X^8$— is a formula of —C($R^{23a}$)=N—C($R^{23c}$)=C($R^{23d}$)—, a pharmaceutically acceptable salt or hydrate thereof,

(12) a compound of (10) wherein the formula of —$X^5$=$X^6$—$X^7$=$X^8$— is a formula of —C($R^{23a}$)=C($R^{23b}$)—N=C($R^{23d}$)—, a pharmaceutically acceptable salt or hydrate thereof,

(13) a compound of (1) wherein the formula of —$X^5$=$X^6$—$X^7$=$X^8$— is a formula of —C($R^{23a}$)=C($R^{23b}$)—C($R^{23c}$)=N—, a pharmaceutically acceptable salt or hydrate thereof,

(14) a compound of any of (10) to (13) wherein Yb is a single bond, a pharmaceutically acceptable salt or hydrate thereof,

(15) a compound of any of (10) to (14) wherein $R^{29}$ is C2-C4 alkyloxy, C1-C4 alkyloxy substituted with a halogen atom, C2-C4 alkylthio or C1-C4 alkylthio substituted with a halogen atom;

a pharmaceutically acceptable salt or hydrate thereof,

(16) a compound of the general formula (III-b):

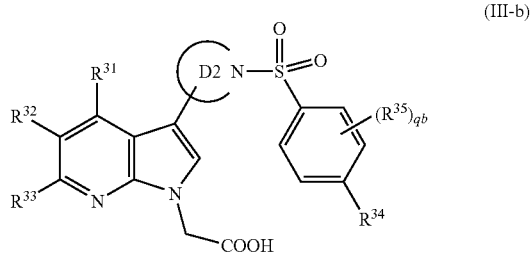

(III-b)

wherein the ring D2 is a formula of

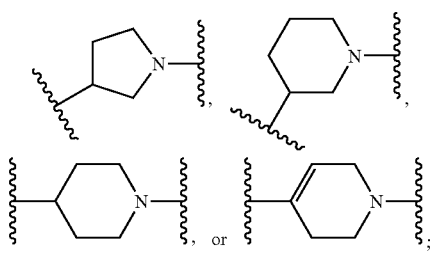

$R^{31}$ and $R^{32}$ are independently a hydrogen atom, a halogen atom, optionally substituted alkyl, optionally substituted alkyloxy, optionally substituted alkylthio, optionally substituted alkylsulfinyl, optionally substituted alkylsulfonyl, optionally substituted amino, cyano, nitro, optionally substituted aryl, optionally substituted heteroaryl or optionally substituted non-aromatic heterocyclic group;

$R^{33}$ is a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or optionally substituted non-aromatic heterocyclic group;

$R^{34}$ is C2-C4 alkyloxy, C1-C4 alkyloxy substituted with a halogen atom, C2-C4 alkylthio, C1-C4 alkylthio substituted with a halogen atom, C3-C4 cycloalkyloxy, C3-C4 cycloalkylmethyloxy or optionally substituted phenoxy;

$R^{35}$ is a halogen atom, optionally substituted alkyl, optionally substituted cycloalkyl, optionally substituted amino, acyl, optionally substituted alkyloxycarbonyl, optionally substituted carbamoyl, cyano, nitro, optionally substituted aryl, optionally substituted arylsulfonyloxy, optionally substituted heteroaryl or optionally substituted non-aromatic heterocyclic group; and qb is 0, 1 or 2;

a pharmaceutically acceptable salt or hydrate thereof,

(17) a compound of (16) wherein $R^{31}$ and $R^{32}$ are hydrogen atoms, a pharmaceutically acceptable salt or hydrate thereof,

(18) a compound of (16) or (17) wherein $R^{33}$ is a halogen atom, optionally substituted alkyloxy, optionally substituted amino, optionally substituted aryl or optionally substituted heteroaryl;

a pharmaceutically acceptable salt or hydrate thereof,

(19) a compound of any of (16) to (19) wherein the ring D2 is a formula of

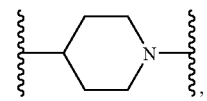

a pharmaceutically acceptable salt or hydrate thereof,

(20) a pharmaceutical composition comprising the compound of any of (1) to (19), pharmaceutically acceptable salt or hydrate thereof,

(21) a pharmaceutical composition of (20) which is a DP receptor antagonist,

(22) a pharmaceutical composition of (20) which is a therapeutic agent for allergy,

(23) a pharmaceutical composition of (20) wherein the therapeutic agent for allergy is a medicine for asthma,

(24) a method for treating a disease related to DP receptor characterized by administration of the compound of any of (1) to (19), pharmaceutically acceptable salt or hydrate thereof,

(25) a method of (24) wherein the disease related to DP receptor is asthma,

(26) use of the compound of any of (1) to (19), pharmaceutically acceptable salt or hydrate thereof, in the manufacturing of a therapeutic agent for treating diseases related to DP receptor, and

(27) use of the compound of (26), pharmaceutically acceptable salt or hydrate thereof wherein the disease related to DP receptor is asthma.

The present invention also includes the following inventions;

[1] a compound of the general formula (I-a):

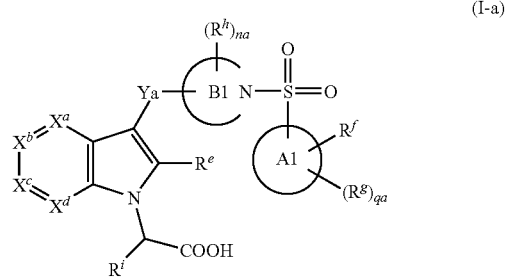

(I-a)

wherein the ring A1 is an aromatic carbocyclic ring or an aromatic heterocyclic ring;

the ring B1 is a 5- or 6-membered nitrogen-containing heterocyclic ring containing only one nitrogen atom as a heteroatom;

the formula of —$X^a$=$X^b$—$X^c$=$X^d$— is a formula of —N=C($R^b$)—C($R^c$)=C($R^d$)—, —C($R^a$)=N—C($R^c$)=C($R^d$)—, —C($R^a$)=C($R^b$)—N=C($R^d$)— or —C($R^a$)=C($R^b$)—C($R^c$)=N—;

$R^a$, $R^b$, $R^c$ and $R^d$ are independently a hydrogen atom, a halogen atom, optionally substituted alkyl, optionally substituted alkenyl, optionally substituted alkynyl, optionally substituted cyloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfony, optionally substituted arylsulfonyoxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group;

$R^e$ is a hydrogen atom, a halogen atom, optionally substituted alkyl, acyl, optionally substituted aryl or optionally substituted heteroaryl;

$R^f$ is a hydrogen atom, optionally substituted C1-C6 alkyloxy, optionally substituted C2-C6 alkenyloxy, optionally substituted C2-C6 alkynyloxy, optionally substituted C3-C6 cycloalkyloxy, optionally substituted C3-C6 cycloalkylmethyloxy, optionally substituted aryloxy, optionally substituted heteroaryloxy, optionally substituted C1-C6 alkylthio, optionally substituted C2-C6 alkenylthio, optionally substituted C2-C6 alkynylthio, optionally substituted C3-C6 cycloalkylthio, optionally substituted C3-C6 cycloalkylmethylthio, optionally substituted arylthio or optionally substituted heteroarylthio;

$R^g$ is independently a halogen atom, optionally substituted alkyl, optionally substituted alkenyl, optionally substituted alkynyl, optionally substituted cyloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfony, optionally substituted arylsulfonyoxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group;

$R^h$ is independently C1-C4 alkyl;

$R^j$ is a hydrogen atom, a halogen atom or C1-C4 alkyl;

Ya is a single bond or optionally substituted C1-C2 alkylene;

na is 0, 1 or 2; and qa is 0, 1 or 2;

a pharmaceutically acceptable salt or hydrate thereof,

[2] a compound of [1] wherein the formula of —$X^a$=$X^b$—$X^c$=$X^d$— is a formula of —N=C($R^b$)—C($R^c$)=C($R^d$)—, a pharmaceutically acceptable salt or hydrate thereof,

[3] a compound of [1] wherein the formula of —$X^a$=$X^b$—$X^c$=$X^d$-, is a formula of —C($R^a$)=N—C($R^c$)=C($R^d$)—, a pharmaceutically acceptable salt or hydrate thereof,

[4] a compound of [1] wherein the formula of —$X^a$=$X^b$—$X^c$=$X^d$-, is a formula of —C($R^a$)=C($R^b$)—N=C($R^d$)—, a pharmaceutically acceptable salt or hydrate thereof,

[5] a compound of [1] wherein the formula of —$X^a$=$X^b$—$X^c$=$X^d$— is a formula of —C($R^a$)=C($R^b$)—C($R^c$)=N—, a pharmaceutically acceptable salt or hydrate thereof,

[6] a compound of any of [1] to [5] wherein $R^e$ is a hydrogen atom, a pharmaceutically acceptable salt or hydrate thereof,

[7] a compound of any of [1] to [6] wherein Ya is a single bond, a pharmaceutically acceptable salt or hydrate thereof,

[8] a compound of any of [1] to [7] wherein the ring B1 is a formula of

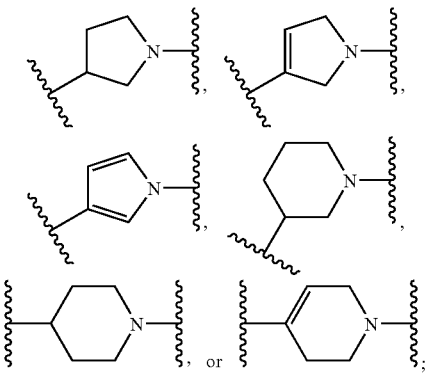

and na is 0;

a pharmaceutically acceptable salt or hydrate thereof,

[9] a compound of any of [1] to [8] wherein the ring A1 is a benzene ring, $R^f$ is C2-C4 alkyloxy, C1-C4 alkyloxy substituted with a halogen atom, C2-C4 alkylthio, C1-C4 alkylthio substituted with a halogen atom, C3-C4 cycloalkyloxy, C3-C4 cycloalkylmethyloxy or optionally substituted phenoxy;

a pharmaceutically acceptable salt or hydrate thereof,

[10] a compound of the general formula (II-a):

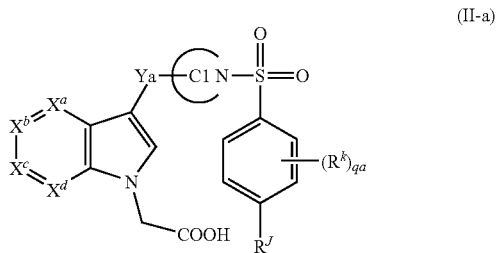

(II-a)

wherein the ring C1 is a ring of the formula of

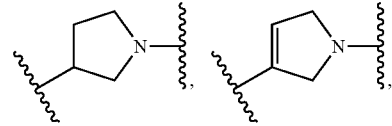

-continued

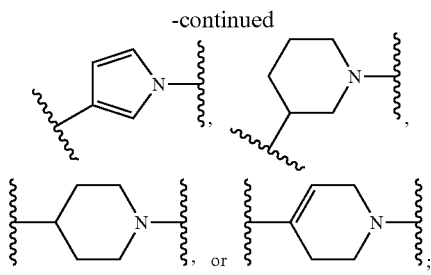

the formula of —X$^a$═X$^b$—X$^c$═X$^d$— is a formula of —N═C(R$^b$)—C(R$^c$)═C(R$^d$)—, —C(R$^a$)═N—C(R$^c$)═C(R$^d$)—, —C(R$^a$)═C(R$^b$)—N═C(R$^d$)— or —C(R)═C(R$^b$)—C(R$^c$)═N—;

R$^a$, R$^b$, R$^c$ and R$^d$ are independently a hydrogen atom, a halogen atom, optionally substituted alkyl, optionally substituted alkenyl, optionally substituted alkynyl, optionally substituted cyloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfony, optionally substituted arylsulfonyoxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group;

R$^j$ is C2-C4 alkyloxy, C1-C4 alkyloxy substituted with a halogen atom, C2-C4 alkylthio, C1-C4 alkylthio substituted with a halogen atom, C3-C4 cycloalkyloxy, C3-C4 cycloalkylmethyloxy or optionally substituted phenoxy;

R$^k$ is independently a halogen atom, optionally substituted alkyl, optionally substituted cycloalkyl, optionally substituted amino, acyl, optionally substituted alkyloxycarbonyl, optionally substituted carbamoyl, cyano, nitro, optionally substituted aryl, optionally substituted arylsulfonyloxy, optionally substituted heteroaryl or optionally substituted non-aromatic heterocyclic group;

Ya is a single bond or optionally substituted C1-C2 alkylene; and qa is 0, 1 or 2;

a pharmaceutically acceptable salt or hydrate thereof,

[11] a compound of [10] wherein the formula of —X$^a$═X$^b$—X$^c$═X$^d$— is a formula of —C(R$^a$)═N—C(R$^c$)═C(R$^d$)—, a pharmaceutically acceptable salt or hydrate thereof,

[12] a compound of [10] wherein the formula of —X$^a$═X$^b$—X$^c$═X$^d$— is a formula of —C(R$^a$)═C(R$^b$)—N═C(R$^d$)—, a pharmaceutically acceptable salt or hydrate thereof,

[13] a compound of [10] wherein the formula of —X$^a$═X$^b$—X$^c$═X$^d$— is a formula of —C(R$^a$)═C(R$^b$)—C(R$^c$)═N—, a pharmaceutically acceptable salt or hydrate thereof,

[14] a compound of any of [10] to [13] wherein Ya is a single bond, a pharmaceutically acceptable salt or hydrate thereof,

[15] a compound of any of [10] to [13] wherein Rj is C2-C4 alkyloxy, C1-C4 alkyloxy substituted with a halogen atom, C2-C4 alkylthio, C1-C4 alkylthio substituted with a halogen atom;

a pharmaceutically acceptable salt or hydrate thereof,

[16] a pharmaceutical composition comprising the compound of any of [1] to [15], pharmaceutically acceptable salt or hydrate thereof,

[17] a pharmaceutical composition of [16] which is a therapeutic agent for allergy,

[18] a pharmaceutical composition of [17] wherein the therapeutic agent for allergy is a medicine for asthma,

[19] a method for treating a disease related to DP receptor characterized by administration of the compound of any of [1] to [15], pharmaceutically acceptable salt or hydrate thereof,

[20] a method of [19] wherein the disease related to DP receptor is asthma,

[21] use of the compound of any of [1] to [15], pharmaceutically acceptable salt or hydrate thereof, in the manufacturing of a therapeutic agent for treating diseases related to DP receptor, and

[22] use of the compound of [21], pharmaceutically acceptable salt or hydrate thereof wherein the disease related to DP receptor is asthma.

Terms herein used are explained below. In the present specification each term is used under the unified definition and has the same meaning when used alone or in combination with other terms.

In the present specification, a term of "halogen atom" means a fluorine atom, a chlorine atom, a bromine atom and an iodine atom. A fluorine atom, a chlorine atom and a bromine atom are preferable.

In the present specification, a term of "hetero atom" means an oxygen atom, a sulfur atom and a nitrogen atom.

In the present specification, a term of "alkyl" means a monovalent straight or branched hydrocarbon group having one to eight carbon atom(s). For example, methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl and the like are exemplified. C1-C6 alkyl is preferred. C1-C4 alkyl is further preferred. When a number of carbon is specified, it means "alkyl" having the carbon number within the range.

In the present specification, a term of "alkenyl" means a monovalent straight or branched hydrocarbon group having two to eight carbon atoms and one or more double bond(s). For example, vinyl, allyl, 1-propenyl, 2-butenyl, 2-pentenyl, 2-hexenyl, 2-heptenyl, 2-octenyl and the like are exemplified. C2-C6 alkenyl is preferred. Moreover, C2-C4 alkenyl is further preferred.

In the present specification, a term of "alkynyl" means a monovalent straight or branched hydrocarbon group having two to eight carbon atoms and one or more triple bond(s). For example, ethynyl, 1-propynyl, 2-propynyl, 2-butynyl, 2-pentynyl, 2-hexynyl, 2-heptynyl, 2-octynyl and the like are exemplified. C2-C6 alkynyl is preferred. Moreover, C2-C4 alkynyl is further preferred.

In the present specification, a term of "cycloalkyl" means a cycloalkyl having three to eight carbon atoms and for example, cyclopropyl, cyclobutyl, cyclopentyl, cyclohexyl, cycloheptyl, cyclooctyl and the like are exemplified. C3-C6 cycloalkyl is preferred.

In the present specification, a term of "cycloalkenyl" means a cycloalkenyl having three to eight carbon atoms and for example, cyclopropenyl, cyclobutenyl, cyclopentenyl, cyclohexenyl, cycloheptenyl, cyloocentyl and the like are exemplified. C3-C6 cycloalkenyl is preferred.

In the present specification, a term of "alkyloxy" means a group wherein an oxygen atom is substituted with one "alkyl" above and for example, methyloxy, ethyloxy, n-propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hexyloxy, n-heptyloxy, n-octyloxy, and the like are exemplified. C1-C6 alkyloxy is preferred. Moreover, C1-C4 alkyloxy is further preferred. When a number of carbon is specified, it means "alkyloxy" having the carbon number within the range.

In the present specification, a term of "alkenyloxy" means a group wherein an oxygen atom is substituted with one "alkenyl" above and for example, vinyloxy, allyloxy, 1-propenyloxy, 2-butenyloxy, 2-pentenyloxy, 2-hexenyloxy, 2-heptenyloxy, 2-octenyloxy and the like are exemplified. C2-C6 alkenyloxy is preferred. Moreover, C2-C4 alkenyloxy is further preferred. When a number of carbon is specified, it means "alkenyloxy" having the carbon number within the range.

In the present specification, a term of "alkynyloxy" means a group wherein an oxygen atom is substituted with one "alkynyl" above and for example, ethynyloxy, 1-propynyloxy, 2-propynyloxy, 2-butynyloxy, 2-pentynyloxy, 2-hexynyloxy, 2-heptynyloxy, 2-octynyloxy and the like are exemplified. C2-C6 alkynyloxy is preferred. Moreover, C2-C4 alkynyloxy is further preferred. When a number of carbon is specified, it means "alkynyloxy" having the carbon number within the range.

In the present specification, a term of "cycloalkyloxy" means a group wherein an oxygen atom is substituted with one "cycloalkyl" above and for example, cyclopropyloxy, cyclobutyloxy, cyclopentyloxy, cyclohexyloxy, cycloheptyloxy and cyclooctyloxy are exemplified. C3-C6 cycloalkyloxy is preferred. When a number of carbon is specified, it means "cycloalkyloxy" having the carbon number within the range.

In the present specification, a term of "cycloalkenyloxy" means a group wherein an oxygen atom is substituted with one "cycloalkenyl" above and for example, cyclopropenyloxy, cyclobutenyloxy, cyclopentenyloxy, cyclohexenyloxy, cycloheptenyloxy, and cyclooctenyloxy are exemplified. C3-C6 cycloalkenyloxy is preferred. When a number of carbon is specified, it means "cycloalkenyloxy" having the carbon number within the range.

In the present specification, a term of "alkylthio" means a group wherein a sulfur atom is substituted with one "alkyl" above, and for example, methylthio, ethylthio, n-propylthio, isopropylthio, n-butylthio, isobutylthio, sec-butylthio, tert-butylthio, n-pentylthio, isopentylthio, 2-pentylthio, 3-pentylthio, n-hexylthio, isohexylthio, 2-hexylthio, 3-hexylthio, n-heptylthio, n-octylthio, and the like are exemplified. C1-C6 Alkylthio is preferred. Moreover, C1-C4 alkylthio is more preferred. When a number of carbon is specified, it means "alkylthio" having the carbon number within the range.

In the present specification, a term of "alkynylthio" means a group wherein a sulfur atom is substituted with one "alkynyl" above and for example, ethynylthio, 1-propynylthio, 2-propynylthio, 2-butynylthio, 2-pentynylthio, 2-hexynylthio, 2-heptynylthio, 2-octynylthio and the like are exemplified. C2-C6 alkynylthio is preferred. Moreover, C2-C4 alkynylthio is further preferred. When a number of carbon is specified, it means "alkynylthio" having the carbon number within the range.

In the present specification, a term of "alkylsulfinyl" means a group wherein sulfinyl is substituted with one "alkyl" above and for example, methylsulfinyl, ethylsulfinyl, n-propylsulfinyl, isopropylsulfinyl, n-butylsulfinyl, isobutylsulfinyl, sec-butylsulfinyl, tert-butylsulfinyl, n-pentylsulfinyl, isopentylsulfinyl, 2-pentylsulfinyl, 3-pentylsulfinyl, n-hexylsulfinyl, isohexylsulfinyl, 2-hexylsulfinyl, 3-hexylsulfinyl, n-heptylsulfinyl, n-octylsulfinyl and the like are exemplified. C1-C6 alkylsulfinyl is preferred. Moreover, C1-C4 alkylsulfinyl is further preferred.

In the present specification, a term of "alkylsulfonyl" means a group wherein sulfonyl is substituted with one "alkyl" above and for example, methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, 2-pentylsulfonyl, 3-pentylsulfonyl, n-hexylsulfonyl, isohexylsulfonyl, 2-hexylsulfonyl, 3-hexylsulfonyl, n-heptylsulfonyl, n-octylsulfonyl and the like are exemplified. C1-C6 alkylsulfonyl is preferred. Moreover, C1-C4 alkylsulfonyl is further preferred.

In the present specification, a term of "alkylsulfonyloxy" means a group wherein an oxygen atom is substituted with one "alkylsulfonyl" above and for example, methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, n-pentylsulfonyloxy, isopentylsulfonyloxy, 2-pentylsulfonyloxy, 3-pentylsulfonyloxy, n-hexylsulfonyloxy, isohexylsulfonyloxy, 2-hexylsulfonyloxy, 3-hexylsulfonyloxy, n-heptylsulfonyloxy, n-octylsulfonyloxy and the like are exemplified. C1-C6 alkylsulfonyl is preferred. Moreover, C1-C4 alkylsulfonyl is further preferred.

In the present specification, a term of "cycloalkylthio" means a group wherein a sulfur atom is substituted with one "cycloalkyl" above and for example, cyclopropylthio, cyclobutylthio, cyclopentylthio, cyclohexylthio, cycloheptylthio, cyclooctylthio and the like are exemplified. C3-C6 cycloalkylthio is preferred. When a number of carbon is specified, it means "cycloalkylthio" having the carbon number within the range.

In the present specification, a term of "cycloalkylsulfinyl" includes a substituent group in which sulfinyl is substituted with one "cycloalkyl" above. For example, cyclopropylsulfinyl, cyclobutylsulfinyl, cyclopentylsulfinyl, cyclohexylsulfinyl, cycloheptylsulfinyl, and cyclooctylsulfinyl are exemplified. Preferably C3-C6 cycloalkylsulfinyl is exemplified.

In the present specification, a term of "cycloalkylsulfonyl" includes a substituent group in which sulfonyl is substituted with one "cycloalkyl" described. For example, cyclopropylsulfonyl, cyclobutylsulfonyl, cyclopentylsulfonyl, cyclohexylsulfonyl, cycloheptylsulfonyl, and cyclooctylsulfonyl are exemplified. Preferably C3-C6 cycloalkylsulfonyl is exemplified.

In the present specification, a term of "cycloalkylsulfinyloxy" includes a substituent group in which an oxygen atom is substituted with one "cycloalkylsulfonyl" above. For example, cyclopropylsulfonyloxy, cyclobutylsulfonyloxy, cyclopentylsulfonyloxy, cyclohexylsulfonyloxy, cycloheptylsulfonyloxy, and cyclooctylsulfonyloxy are exemplified. Preferably C3-C6 cycloalkylsulfonyloxy is exemplified.

In the present specification, a term of "cycloalkenylthio" includes a substituent group in which a sulfur atom is substituted with one "cycloalkenyl" above. For example, cyclopropenylthio, cyclobutenylthio, cyclopentenylthio, cyclohexenylthio, cycloheptenylthio, and cyclooctenylthio are exemplified. Preferably C3-C6 cycloalkenylthio is exemplified. When a number of carbon is specified, it means "cycloalkenylthio" having the carbon number within the range.

In the present specification, a term of "cycloalkenylsulfinyl" includes a substituent group in which sulfinyl is substituted with one "cycloalkenyl" above. For example, cyclopropenylsulfinyl, cyclobutenylsulfinyl, cyclopentenylsulfinyl, cyclohexenylsulfinyl, cycloheptenylsulfinyl, and cyclooctenylsulfinyl are exemplified. Preferably C3-C6 cycloalkenylsulfinyl is exemplified.

In the present specification, a term of "cycloalkenylsulfonyl" includes a substituent group in which sulfonyl is substituted with one "cycloalkenyl" above. For example, cyclopropenylsulfonyl, cyclobutenylsulfonyl, cyclopentenylsulfonyl, cyclohexenylsulfonyl, cycloheptenylsulfonyl, and cyclooctenylsulfonyl are exemplified. Preferably C3-C6 cycloalkenylsulfonyl is exemplified.

In the present specification, a term of "cycloalkenylsulfonyloxy" includes a substituent group in which an oxygen atom is substituted with one "cycloalkenylsulfonyl" above. For example, cyclopropenylsulfonyloxy, cyclobutenylsulfonyloxy, cyclopentenylsulfonyloxy, cyclohexenylsulfonyloxy, cycloheptenylsulfonyloxy, and cyclooctenylsulfonyloxy are exemplified. Preferably C3-C6 cycloalkenylsulfonyloxy is exemplified.

In the present specification, a term of "alkyloxycarbonyl" includes a substituent group in which carbonyl is substituted with one "alkyloxy" above. For example, methyloxycarbonyl, ethyloxycarbonyl, n-propyloxycarbonyl, isopropyloxycarbonyl, n-butyloxycarbonyl, tert-butyloxycarbonyl and n-pentyloxycarbonyl are exemplified. Preferably C1-C2 alkyloxycarbonyl is exemplified.

In the present specification, a term of "alkenyloxycarbonyl" includes a substituent group in which carbonyl is substituted with one "alkenyloxy" above. For example, vinyloxycarbonyl, allyloxycarbonyl, 1-propenyloxycarbonyl, and 2-pentenyloxyarbonyl are exemplified. Preferably C2-C4 alkyloxycarbonyl is exemplified.

In the present specification, a term of "alkynyloxycarbonyl" includes a substituent group in which carbonyl is substituted with one "alkynyloxy" above. For example, ethynyloxycarbonyl, 1-propynyloxycarbonyl, 2-propynyloxycarbonyl, 2-butynyloxyarbonyl and 2-pentynyloxycarbonyl are exemplified. Preferably C2-C4 alkynyloxycarbonyl is exemplified.

In the present specification, a term of "acyl" includes alkylcarbonyl wherein the part of alkyl is "alkyl" described before, alkenylcarbonyl wherein the part of alkenyl is "alkenyl" described before, alkynylcarbonyl wherein the part of alkynyl is "alkynyl" described before, cycloalkylcarbonyl wherein the part of cycloalkyl is "cycloalkyl" described before, arylcarbonyl wherein the part of aryl is "aryl" described below, heteroarylcarbonyl wherein the part of heteroaryl is "heteroaryl" described below and non-aromatic heterocycliccarbonyl wherein the part of non-aromatic heterocyclic group is "non-aromatic heterocyclic group" described below. "Alkyl", "alkenyl", "alkynyl", "cycloalkyl", "aryl", "heteroaryl" and "non-aromatic heterocyclic" may be substituted respectively with substituent groups exemplified in "optionally substituted alkyl", "optionally substituted alkenyl", "optionally substituted alkynyl", "optionally substituted cycloalkyl", "optionally substituted aryl", "optionally substituted heteroaryl" and "optionally substituted non-aromatic heterocyclic group" described below. Examples of the acyl group include acetyl, propionyl, butyroyl, cyclohexylcarbonyl, benzoyl, pyridinecarbonyl and the like.

In the present specification, a term of "optionally substituted amino" includes an amino group which may be substituted with one or two group(s) of "alkyl" before, "alkenyl" before, "alkynyl" before, "cycloalkyl" before, "cycloalkenyl" before, "aryl" below, "heteroaryl" below, "acyl" before, "alkyloxycarbonyl" before, "alkenyloxycarbonyl" before, "alkynyloxycarbonyl" before, "alkylsulfonyl", "alkenylsulfonyl", "alkynylsulfonyl", "arylsulfonyl" and/or "heteroarylsulfonyl" before. Examples of the optionally substituted amino group include amino, methylamino, dimethylamino, ethylamino, diethylamino, ethylmethylamino, benzylamino, acetylamino, benzoylamino, methyloxycarbonylamino and methanesulfonylamino. Preferably, amino, methylamino, dimethylamino, diethylamino, ethylmethylamino, acetylamino and methanesulfonylamino are exemplified.

In the present specification, a term of "optionally substituted carbamoyl" includes an aminocarbonyl group wherein the part of optionally substituted amino is "optionally substituted amino" described before and examples of the optionally substituted carbamoyl group includes carbamoyl, N-methylcarbamoyl, N,N-dimethylcarbamoyl, N-ethyl-N-methylcarbamoyl, N,N-diethylcarbamoyl, N-phenylcarbamoyl, N-benzylcarbamoyl, N-acetylcarbamoyl and N-methylsulfonylcarbamoyl etc. Preferably, carbamoyl, N-methylcarbamoyl, N,N-dimethylcarbamoyl and N-methylsulfonylcarbamoyl etc. are exemplified.

In the present specification, a term of "optionally substituted sulfamoyl" includes an aminosulfonyl group wherein the part of optionally substituted amino is "optionally substituted amino" described before and examples of the optionally substituted sulfamoyl group include sulfamoyl, N-methylsulfamoyl, N,N-dimethylsulfamoyl, N-ethyl-N-methylsulfamoyl, N,N-diethylsulfamoyl, N-phenylsulfamoyl, N-benzylsulfamoyl, N-acetylsulfamoyl and N-methylsulfonylsulfamoyl etc. Preferably, sulfamoyl, N-methylsulfamoyl, N,N-dimethylsulfamoyl and N-methylsulfonylsulfamoyl etc. are exemplified.

In the present specification, a term of "alkylene" includes a straight or branched alkylene group having one to eight carbon atom(s) and for example, methylene, ethylene, 1-methylethylene, trimethylene, 1-methyltrimethylene, pentamethylene, hexamethylene etc. are exemplified. C1-C4 alkylene is preferred. Moreover, C1-C2 alkylene is further preferred.

In the present specification, a term of "aryl" includes a monocyclic or fused cyclic aromatic hydrocarbons and it may be fused with "cycloalkyl" before, "cycloalkenyl" before or "non-aromatic heterocyclic group" below at any possible position. Both of monocyclic ring and fused ring may be substituted at any position and for example, phenyl, 1-naphthyl, 2-naphthyl, anthryl, tetrahydronaphthyl, 1,3-benzodioxolyl, 1,4-benzodioxanyl etc. are exemplified. Phenyl, 1-naphthyl and 2-naphthyl are preferred. Moreover, phenyl is further preferred.

In the present specification, a term of "non-aromatic heterocyclic group" in $R^1$, $R^2$, $R^3$, $R^4$, $R^5$, $R^{15}$, $R^{16}$, $R^{17}$ and $R^{18}$ includes a 5- to 7-membered non-aromatic heterocyclic ring containing one or more of heteroatom(s) selected independently from oxygen, sulfur and nitrogen atoms or a multicyclic ring formed by fusing the two or more rings thereof. For example, pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidyl (e.g., piperidino, 2-piperidyl), piperadinyl (e.g., 1-piperadinyl), indolinyl (e.g., 1-indolinyl), isoindolinyl (e.g., isoindolinyl), morpholinyl (e.g., morpholino, 3-morpholinyl) etc. are exemplified.

In the present specification, a term of "non-aromatic heterocyclic group" in $R^7$, $R^8$, $R^{10}$, $R^{11}$, $R^{13}$, $R^{14}$, $R^{20}$ and $R^{21}$ includes a 5- to 7-membered non-aromatic heterocyclic ring containing one or more of heteroatom(s) selected independently from oxygen, sulfur and nitrogen atoms or a multicyclic ring formed by fusing the two or more rings thereof. For example, pyrrolidinyl (e.g., 1-pyrrolidinyl, 2-pyrrolidinyl), piperidyl (e.g., piperidino, 2-piperidyl), piperadinyl (e.g., 1-piperadinyl), morpholinyl (e.g., morpholino, 3-morpholinyl) etc. are exemplified.

In the present specification, a term of "heteroaryl" in $R^1$, $R^2$, $R^3$, $R^4$, $R^5$, $R^{15}$, $R^{16}$, $R^{17}$ and $R^{18}$ includes a 5- to 6-membered aromatic ring containing one or more of heteroatom(s) selected independently from oxygen, sulfur and nitrogen atoms and it may be fused with "cycloalkyl" before, "aryl" before, "non-aromatic heterocyclic group" or other heteroaryl at any possible position. The heteroaryl group may be substituted at any position whenever it is a monocyclic ring or a fused ring. For example, pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolidinyl (e.g., 2-indolidinyl, 6-indolidinyl), isoindolynyl (e.g., 2-isoindolynyl), indolyl (e.g., 1-indolyl, 2-indolyl, 3-indolyl), indazolyl (e.g., 3-indazolyl), purinyl (e.g., 8-purinyl), quinolidinyl (e.g., 2-quinolidinyl), isoquinolyl (e.g., 3-isoquinolyl), quinolyl (e.g., 2-quinolyl, 5-quinolyl), phtharazinyl (e.g., 1-phtharazinyl), naphthylidinyl (e.g., 2-naphthylidinyl), quinolanyl (e.g., 2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzoimidazolyl (e.g., 2-benzoimidazolyl), benzoisoxazolyl (e.g., 3-benzoisoxazolyl), benzooxazolyl (e.g., 2-benzooxazolyl), benzooxadiazolyl (e.g., 4-benzooxadiazolyl), benzoisothiazolyl (e.g., 3-benzoisothiazolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl) and benzodioxolyl (e.g., 1,3-benzodioxolyl) are exemplified.

In the present specification, a term of "heteroaryl" in $R^7$, $R^8$, $R^{10}$, $R^{11}$, $R^{13}$, $R^{14}$, $R^{20}$ and $R^{21}$ includes a 5- to 6-membered aromatic ring containing one or more of heteroatom(s) selected independently from oxygen, sulfur and nitrogen atoms and it may be fused with "cycloalkyl" before, "aryl" before, "non-aromatic heterocyclic group" before or other heteroaryl at any possible position. The heteroaryl group may be substituted at any position whenever it is monocyclic or fused ring. For example, furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), oxadiazolyl (e.g., 1,3,4-oxadiazolyl), thiadiazolyl (e.g., 1,3,4-thiadiazolyl), benzoimidazolyl (e.g., 2-benzoimidazolyl), benzoisoxazolyl (e.g., 3-benzoisoxazolyl), benzooxazolyl (e.g., 2-benzooxazolyl), benzofuryl (e.g., 3-benzofuryl), benzothienyl (e.g., 2-benzothienyl) are exemplified.

In the present specification, a term of "aryloxy" includes a substituent group in which an oxygen atom is substituted with one "aryl" above and for example, phenyloxy and naphthyloxy etc. are exemplified.

In the present specification, a term of "arylthio" includes a substituent group in which a sulfur atom is substituted with one "aryl" above and for example, phenylthio and naphthylthio etc. are exemplified.

In the present specification, a term of "arylsulfinyl" includes a substituent group in which sulfinyl is substituted with one "aryl" above and for example, phenylsulfinyl and naphthylsulfinyl etc. are exemplified.

In the present specification, a term of "arylsulfonyl" includes a substituent group in which sulfonyl is substituted with one "aryl" above and for example, phenylsulfonyl and naphthylsulfinyl etc. are exemplified.

In the present specification, examples of "arylsulfonyloxy" include phenylsulfonyloxy and naphthylsulfonyloxy etc.

In the present specification, a term of "heteroaryloxy" includes a substituent group in which an oxygen atom is substituted with one "heteroaryl" above. For example, pyrrolyloxy, furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, pyridazinyloxy, tetrazolyloxy, oxadiazolyloxy, thiadiazolyloxy, indolidinyloxy, isoindolynyloxy, indolyloxy, indazolyloxy, purinyloxy, quinolidinyloxy, isoquinolyloxy, quinolyloxy, phtharazinyloxy, naphthylidinyloxy, quinolanyloxy, quinazolinyloxy, cinnolinyloxy, pteridinyloxy, carbazolyloxy, phenanthridinyloxy, acridinyloxy, dibenzofuranyloxy, benzoimidazolyloxy, benzoisoxazolyloxy, benzooxazolyloxy, benzooxadiazolyloxy, benzoisothiazolyloxy, benzothiazolyloxy, benzofuryloxy, benzothienyloxy, dibenzothienyloxy and benzodioxolyloxy are exemplified. Preferably furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy and pyridazinyloxy are exemplified In the present specification, a term of "heteroarylthio" includes a substituent group in which a sulfur atom is substituted with one "heteroaryl" above. For example, pyrrolylthio, furylthio, thienylthio, imidazolylthio, pyrazolylthio, isothiazolylthio, isoxazolylthio, oxazolylthio, thiazolylthio, pyridylthio, pyrazinylthio, pyrimidinylthio, pyridazinylthio, tetrazolylthio, oxadiazolylthio, thiadiazolylthio, indolidinylthio, isoindolynylthio, indolylthio, indazolylthio, purinylthio, quinolidinylthio, isoquinolylthio, quinolylthio, phtharazinylthio, naphthylidinylthio, quinolanylthio, quinazolinylthio, cinnolinylthio, pteridinylthio, carbazolylthio, phenanthridinylthio, acridinylthio, dibenzofuranylthio, benzoimidazolylthio, benzoisoxazolylthio, benzooxazolylthio, benzooxadiazolylthio, benzoisothiazolylthio, benzothiazolylthio, benzofurylthio, benzothienylthio, dibenzothienylthio and benzodioxolylthio etc. are exemplified. Preferably furylthio, thienylthio, imidazolylthio, pyrazolylthio, isothiazolylthio, isoxazolylthio, oxazolylthio, thiazolylthio, pyridylthio, pyrazinylthio, pyrimidinylthio, and pyridazinylthio etc. are exemplified.

In the present specification, a term of "heteroarylsulfinyl" includes a substituent group in which sulfinyl is substituted with one "heteroaryl" above. For example, pyrrolylsulfinyl, furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl, pyridazinylsulfinyl, tetrazolylsulfinyl, oxadiazolylsulfinyl, thiadiazolylsulfinyl, indolidinylsulfinyl, isoindolynylsulfinyl, indolylsulfinyl, indazolylsulfinyl, purinylsulfinyl, quinolidinylsulfinyl, isoquinolylsulfinyl, quinolylsulfinyl, phtharazinylsulfinyl, naphthylidinylsulfinyl, quinolanylsulfinyl, quinazolinylsulfinyl, cinnolinylsulfinyl, pteridinylsulfinyl, carbazolylsulfinyl, phenanthridinylsulfinyl, acridinylsulfinyl, dibenzofuranylsulfinyl, benzoimidazolylsulfinyl, benzoisoxazolylsulfinyl, benzooxazolylsulfinyl, benzooxadiazolylsulfinyl, benzoisothiazolylsulfinyl, benzothiazolylsulfinyl, benzofurylsulfinyl, benzothienylsulfinyl, dibenzothienylsulfinyl and benzodioxolylsulfinyl etc. are exemplified. Preferably furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl and pyridazinylsulfinyl etc. are exemplified.

In the present specification, a term of "heteroarylsulfonyl" includes a substituent group in which sulfonyl is substituted with one "heteroaryl" above. For example, pyrrolylsulfonyl, furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl, pyridazinylsulfonyl, tetrazolylsulfonyl, oxadiazolylsulfonyl, thiadiazolylsulfonyl, indolizinylsulfonyl, isoindolylsulfonyl, indolylsulfonyl, indazolylsulfonyl, purinylsulfonyl, quinolidinylsulfonyl, isoquinolylsulfonyl, quinolylsulfonyl, phtharazinylsulfonyl, naphthilidinylsulfonyl, quinolanyl sulfonyl, quinazolinylsulfonyl, cinnolinylsulfonyl, pteridinylsulfonyl, carbazolylsulfonyl, phenanthridinylsulfonyl, acridinylsulfonyl, dibenzofuranylsulfonyl, benzoimidazolylsulfonyl, benzoisoxazolylsulfonyl, benzooxazolylsulfonyl, benzooxadiazolylsulfonyl, benzoisothiazolylsulfonyl, benzothiazolylsulfonyl, benzofurylsulfonyl, benzothienylsulfonyl, dibenzothienylsulfonyl and benzodioxolylsulfonyl are exemplified. Preferably furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl and pyridazinylsulfonyl are exemplified.

In the present specification, a term of "heteroarylsulfonyloxy" includes a substituent group in which an oxygen atom is substituted with one "heteroarylsulfonyl" above. For example, pyrrolylsulfonyloxy, furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy, pyridazinylsulfonyloxy, tetrazolylsulfonyloxy, oxadiazolylsulfonyloxy, thiadiazolylsulfonyloxy, indolizinylsulfonyloxy, isoindolylsulfonyloxy, indolylsulfonyloxy, indazolylsulfonyloxy, purinylsulfonyloxy, quinolidinylsulfonyloxy, isoquinolylsulfonyloxy, quinolylsulfonyloxy, phtharazinylsulfonyloxy, naphthilidinylsulfonyloxy, quinolanylsulfonyloxy, quinazolinylsulfonyloxy, cinnolinylsulfonyloxy, pteridinylsulfonyloxy, carbazolylsulfonyloxy, phenanthridinylsulfonyloxy, acridinylsulfonyloxy, dibenzofuranylsulfonyloxy, benzoimidazolylsulfonyloxy, benzoisoxazolylsulfonyloxy, benzooxazolylsulfonyloxy, benzooxadiazolylsulfonyloxy, benzoisothiazolylsulfonyloxy, benzothiazolylsulfonyloxy, benzofurylsulfonyloxy, benzothienylsulfonyloxy, dibenzothienylsulfonyloxy and benzodioxolylsulfonyloxy etc. are exemplified. Preferably, furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy and pyridazinylsulfonyloxy etc. are exemplified.

In the present specification, a term of "aromatic carbocyclic ring" includes an aromatic monocyclic or fused carbocyclic ring and for example, a benzene ring, a naphthalene ring and an anthracene ring are exemplified. A benzene ring is preferred.

In the present specification, a term of "aromatic heterocyclic ring" includes an aromatic monocyclic or fused heterocyclic ring. For example, a pyrrole ring, a furan ring, a thiophen ring, a pyrazole ring, an imidazole ring, an isothiazole ring, an isoxazole ring, an oxazole ring, a thiazole ring, a pyrazine ring, a pyrimidine ring, a pyridazine ring, a tetrazole ring, an oxadiazole ring, a thiadiazole ring, an indolizine ring, an isoindole ring, an indole ring, an indazole ring, a purine ring, a quinolidine ring, an isoquinoline ring, a quinoline ring, a phtharazine ring, a naphthyridine ring, a quinolane ring, a quinazoline ring, a cinnoline ring, a pteridine ring, a carbazole ring, a phenanthridine ring, an acridine ring, a dibenzofuran ring, a benzoimidazole ring, a benzoisoxazole ring, a benzooxazole ring, a benzooxadiazole ring, a benzoisothiazole ring, a benzothiazole ring, a benzofuran ring, a benzothiophen ring, a dibenzothiophen ring and a benzodixolane ring are exemplified. Preferably a pyridine ring, a furan ring and a thiophen ring are exemplified.

In the present specification, a term of "C1-C6 alkylene" includes a straight or branched alkylene group having one to six carbon atoms, and for example, —CH$_2$—, —CH(CH$_3$)—, —C(CH$_3$)$_2$—, —CH$_2$CH$_2$—, —CH(CH$_3$)CH$_2$—, —C(CH$_3$)$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH$_2$CH$_2$CH$_2$CH$_2$CH$_2$— are exemplified. Preferably, —CH$_2$—, —CH$_2$CH$_2$—, —CH$_2$CH$_2$CH$_2$— and —CH$_2$CH$_2$CH$_2$CH$_2$— are exemplified.

In the present specification, a term of "alkylene optionally containing one or two heteroatom(s)" includes a straight or branched alkylene group having one to six carbon atoms, optionally containing one or two heteroatom(s) which may be substituted with "alkyl" above, and for example, —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$O—, —OCH$_2$CH$_2$—, —CH$_2$CH$_2$S—, —SCH$_2$CH$_2$—, —CH$_2$CH$_2$OCH$_2$CH$_2$—, —OCH$_2$CH$_2$O—, —OCH$_2$O—, —NHCH$_2$CH$_2$CH$_2$— and —N(CH$_3$)CH$_2$CH$_2$CH$_2$— etc. are exemplified. Preferably, —CH$_2$—, —CH$_2$CH$_2$—, —CH$_2$CH$_2$CH$_2$—, —CH$_2$CH$_2$CH$_2$CH$_2$—, —OCH$_2$CH$_2$O—, —OCH$_2$O— and —N(CH$_3$)CH$_2$CH$_2$CH$_2$— are exemplified.

In the present specification, a term of "alkenylene optionally containing one or two heteroatom(s)" includes a straight or branched alkenylene group having two to six carbon atoms, optionally containing one or two heteroatom(s) which may be substituted with "alkyl" above, and for example, —CH═CHCH═CH—, —CH═CHO—, —OCH═CH—, —CH═CHS—, —SCH═CH—, —CH═CHNH—, —NHCH═CH—, —CH═CH—CH═N— and —N═CH—CH═CH— are exemplified. Preferably, —CH═CHCH═CH—, —CH═CHCH═N— and —N═CHCH═CH— are exemplified.

In the present specification, a term of "alkynylene optionally containing one or two heteroatom(s)" includes a straight or branched alkynylene group having two to six carbon atoms, optionally containing one or two heteroatom(s) which may be substituted with "alkyl" above, and for example, —C≡CCH$_2$—, —CH$_2$C≡CCH$_2$—, —CH$_2$C≡CCH$_2$O—, —OCH$_2$C≡CH—, —CH$_2$C≡CCH$_2$S—, —SCH₂C≡CH—, —CH₂C≡CCH₂NH—, —NHCH₂C≡CH—, —CH₂C≡CCH₂N(CH₃)— and —N(CH₃)CH₂C≡CH— are exemplified. Especially, —CH₂C≡CCH₂— and —OCH₂C≡CH— are preferred.
In the present specification, examples of "3- to 8-membered nitrogen-containing non-aromatic heterocyclic ring" includes rings shown in the formulae of
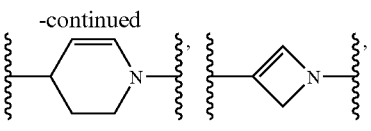
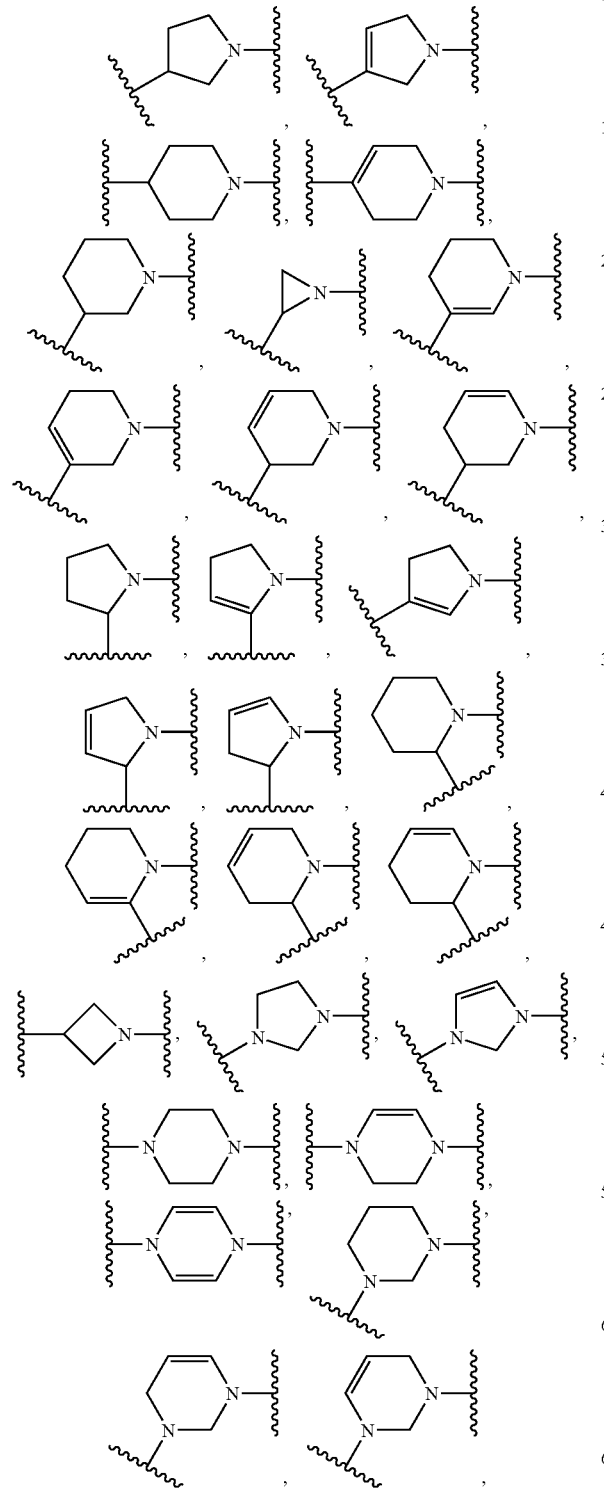

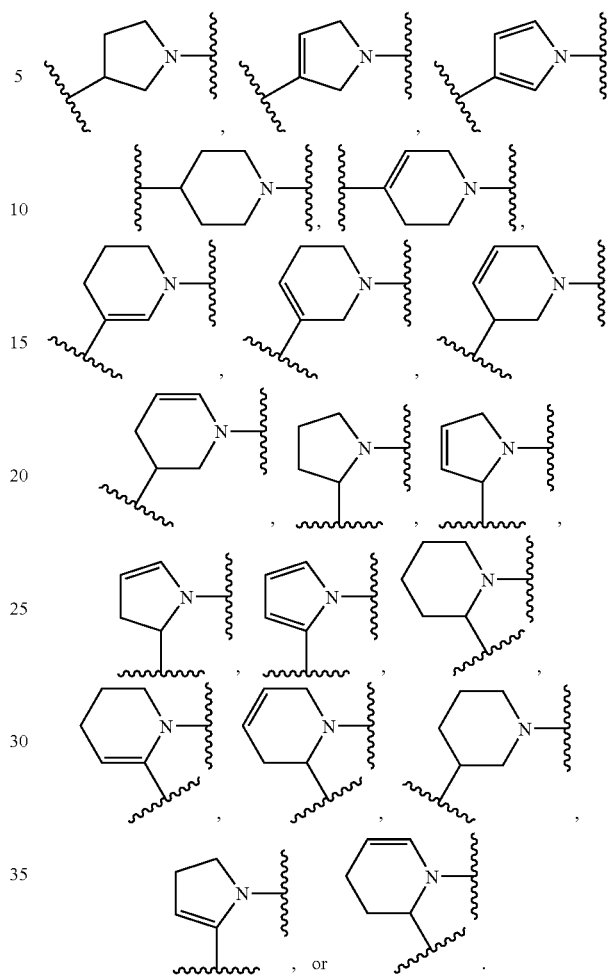

In the present specification, a term of "3- to 8-membered nitrogen-containing heteroaromatic ring" includes a 3- to 8-membered heteroaromatic ring containing one or more of nitrogen atom(s), and further optionally an oxygen atom and/ or sulfur atom in the ring. For example, pyrrolyl (e.g., 1-pyrrolyl, 2-pyrrolyl, 3-pyrrolyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl) and thiadiazolyl (e.g., 1,3,4-thiadiazolyl) are exemplified.

In the present specification, examples of "5- or 6-membered nitrogen-containing heteroaromatic ring containing only one nitrogen atom as a heteroatom" includes rings shown in the formulae of In the present specification, examples of substituents in "optionally substituted alkyl", "optionally substituted alkyloxy", "optionally substituted alkylthio", "optionally substituted alkylsulfinyl", "optionally substituted alkylsulfonyl", "optionally substituted alkylsulfonyloxy" and "the optionally substituted alkyloxycarbonyl" include cycloalkyl, alkylene optionally containing one or two heteroatom(s), hydroxy, oxo, alkyloxy optionally substituted with a substituent group A at one to three position(s), mercapto, alkylthio, halogen atom, nitro, cyano, carboxy, alkyloxycarbonyl, optionally substituted amino, optionally substituted carbamoyl, acyl, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), optionally substituted non-aromatic heteroaromatic ring group which may be substituted with a substituent group C at one to three position(s) (e.g., morpholinyl, pyrrolidinyl, piperadinyl), aryloxy optionally substituted with a substituent group B at one to three position(s) (e.g., phenyloxy), alkylsulfonyl and the like. These can be substituted with one to three substituent(s) at any possible position.

In the present specification, examples of substituents in "optionally substituted alkenyl", "optionally substituted alkynyl", "optionally substituted alkenyloxy", "optionally substituted alkynyloxy", "optionally substituted alkenylthio", "optionally substituted alkynylthio", "optionally substituted alkenyloxycarbonyl", "optionally substituted alkynyloxycarbonyl", "optionally substituted cycloalkyl", "optionally substituted cycloalkenyl", "optionally substituted cycloalkyloxy, "optionally substituted cycloalkenyloxy, "optionally substituted cycloalkylthio", "optionally substituted cycloalkenylthio", "optionally substituted cycloalkylsulfinyl", "optionally substituted cycloalkenylsulfinyl", "optionally substituted cycloalkylsulfonyl", "optionally substituted cycloalkenylsulfonyl", "optionally substituted cycloalkylsulfonyloxy", "optionally substituted cycloalkenylsulfonyloxy", "optionally substituted alkenyloxycarbonyl", "optionally substituted C1-C6 alkylene", "optionally substituted alkenylene" and "the optionally substituted alkynylene" include alkyl optionally substituted with a substituent group D at one to three position(s), cycloalkyl, alkylene optionally containing one or two heteroatom(s), hydroxy, oxo, alkoxyl optionally substituted with a substituent group A at one to three position(s), mercapto, alkylthio, a halogen atom, nitro, cyano, carboxy, alkyloxycarbonyl, optionally substituted amino, optionally substituted carbamoyl, acyl acyloxy, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), non-aromatic heterocyclic group optionally substituted with a substituent group C at one to three position(s) (e.g., morpholinyl, pyrrolidinyl, piperadinyl), aryloxy optionally substituted with a substituent group C at one to three position(s) (e.g., phenyloxy), alkylsulfonyl and the like. These can be substituted with one or more substituent(s) at any possible position.

In the present specification, examples of substituents in "optionally substituted aryl", "optionally substituted phenoxy", "optionally substituted aryloxy", "optionally substituted phenylthio", "optionally substituted arylthio", "optionally substituted arylsulfinyl", "optionally substituted arylsulfonyl", "optionally substituted arylsulfonyloxy", "optionally substituted heteroaryl", "optionally substituted heteroaryloxy", "optionally substituted heteroarylthio", "optionally substituted heteroarylsulfinyl", "optionally substituted heteroarylsulfonyl", "optionally substituted heteroarylsulfonyloxy" and "optionally substituted non-aromatic heterocyclic group" include alkyl optionally substituted with a substituent group D at one to three position(s), cycloalkyl, alkenyl, alkynyl, hydroxy, alkyloxy optionally substituted with a substituent group A at one to three position(s), aryloxy optionally substituted with a substituent group B at one to three position(s) (e.g., phenoxy), mercapto, alkylthio, a halogen atom, nitro, cyano, carboxy, alkyloxycarbonyl, acyl, alkylsulfonyl, optionally substituted amino, optionally substituted carbamoyl, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), non-aromatic heterocyclic group optionally substituted with a substituent group C at one to three position(s) (e.g., morpholinyl, pyrrolidinyl, piperadinyl) and the like. These can be substituted with one or more substituent(s) at any possible position.

Substituent group A is a group of a halogen atom and phenyl optionally substituted with one to three substituent(s) selected from the Substituent group B.

Substituent group B is a group of a halogen atom, alkyl, alkyloxy, cyano and nitro.

Substituent group C is a group of a halogen atom and alkyl.

Substituent group D is a group of a halogen atom and alkyloxy.

In the specification a term of "carboxy equivalent" means a biological equivalent and includes substituents having the same polar effect as a carboxy group. For example, —CONHCN, —CONHOH, —CONHOMe, —CONHOt-Bu, —CONHOCH$_2$Ph, —SO$_3$H, —SO$_2$NH$_2$, —SO$_2$NHMe, —NHCONH$_2$, —NHCONMe$_2$, —P(=O)(OH)$_2$, —P(=O)(OH)(OEt), —P(=O)(OH)NH$_2$, —P(=O)(OH)NHMe, —CONHSO$_2$Ph, —SO$_2$NHCOMe, —SO$_2$NHCOPh, and the formula;

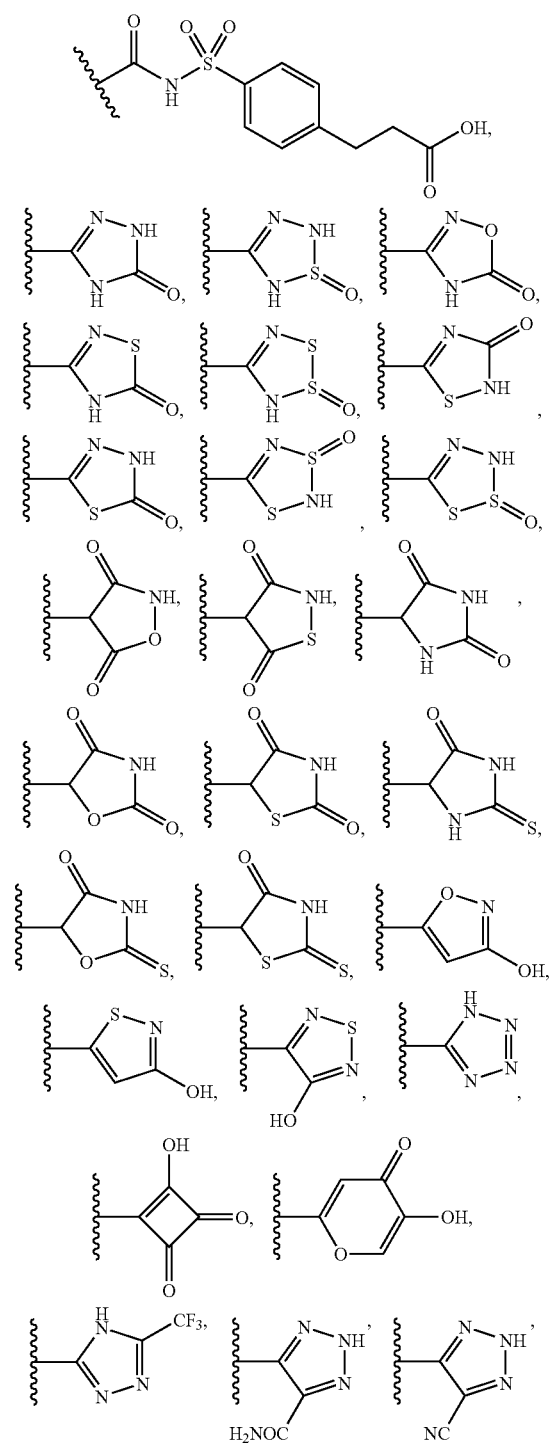

-continued

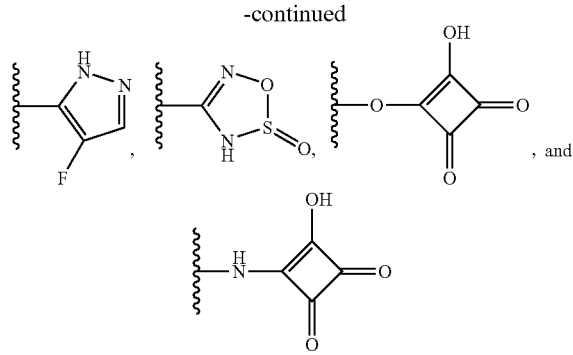

are exemplified.

Preferably, —CONHOt-Bu, —CONHOCH$_2$Ph, —SO$_3$H, —CONHSO$_2$Ph, —SO$_2$NHCOMe, —SO$_2$NHCOPh, and the formula;

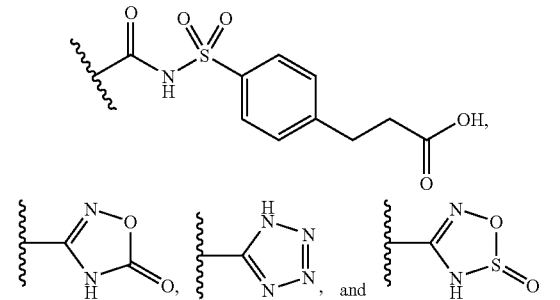

are exemplified.

Groups of preferred substituents in the ring A, ring B, the formula of —X$^1$=X$^2$—X$^3$=X$^4$—, R$^1$ to R$^9$, M, Y, L$^1$, L$^2$, L$^3$, n and q of the compound of general formula (I) are shown with (Ia) to (IIk). Compounds having possible combination of them are preferable. The substituent of the general formula (I) is applicable as each corresponding substituent of the formula (I-a) and (I-b).

In the ring A, (Ia) a benzen ring, a furan ring, a thiophen ring or a furan ring is preferable, and further (Ib) a benzene ring or a pyridine ring is preferable.

In the ring B, (Ic) a formula of

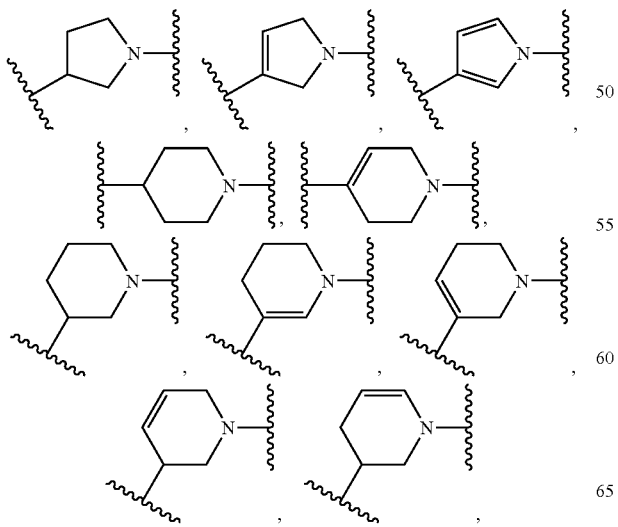

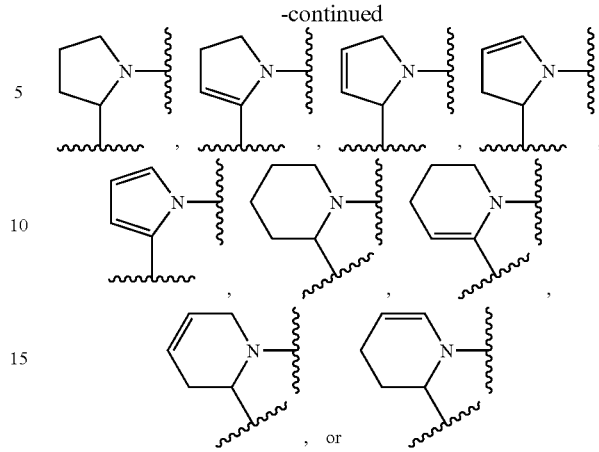

is preferable, (Id) a formula of

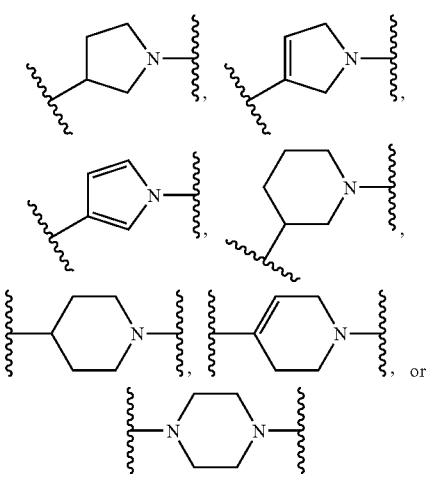

is more preferable, (Ie) a formula of

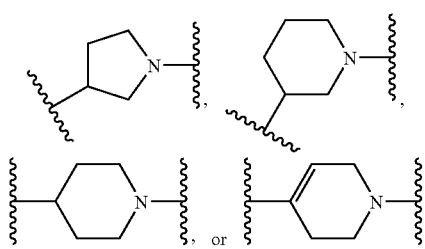

is further more preferable, and (If) a formula of

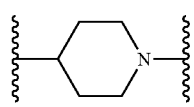

is most preferable.

In the formula of —X$^1$=X$^2$—X$^3$=X$^4$—, (Ig) a formula of —N=C(R$^2$)—C(R$^3$)=C(R$^4$)—, —C(R$^1$)=C(R$^2$)—N=C ($R^4$)— or —C($R^1$)=C($R^2$)—C($R^3$)=N— is preferable, and (Ih) a formula of —C($R^1$)=C($R^2$)—C($R^3$)=N— is further preferable.

In $R^1$, $R^2$, $R^4$ and $R^5$ independently, (Ii) a hydrogen atom, a halogen atom, optionally substituted alkyl, optionally substituted alkyloxy, optionally substituted amino, cyano, nitro, optionally substituted aryl or optionally substituted heteroaryl is preferable, (Ij) a hydrogen atom, a halogen atom or optionally substituted alkyl is more preferable and (Ik) a hydrogen atom is most preferable.

In $R^3$, (Il) a hydrogen atom, a halogen atom, optionally substituted alkyl, optionally substituted alkyloxy, optionally substituted cycloalkyloxy, optionally substituted amino, acyl, optionally substituted carbamoyl, cyano, nitro, optionally substituted aryl, optionally substituted heteroaryl or optionally substituted non-aromatic heterocyclic group is preferable, (Im) a hydrogen atom, a halogen atom, optionally substituted alkyl, optionally substituted alkyloxy, optionally substituted amino, optionally substituted carbamoyl, optionally substituted aryl, optionally substituted heteroaryl or optionally substituted non-aromatic heterocyclic group is more preferable and (In) a halogen atom, optionally substituted alkyloxy, optionally substituted amino, optionally substituted aryl, optionally substituted heteroaryl or optionally substituted non-aromatic heterocyclic group is most preferable.

In $R^6$, (Io) optionally substituted C1-C6 alkyloxy, optionally substituted C1-C6 alkylthio, optionally substituted C3-C6 cycloalkyloxy, optionally substituted C3-C6 cycloalkylthio, optionally substituted aryloxy, or optionally substituted arylthio is preferable, (Ip) optionally substituted C1-C6 alkyloxy or optionally substituted C1-C6 alkylthio is further preferable, and (Iq) C2-C4 alkyloxy is most preferable.

In $R^7$, (Ir) a halogen atom, optionally substituted alkyl, optionally substituted alkyloxy, cyano, nitro, optionally substituted aryl or optionally substituted heteroaryl is preferable, (Is) a halogen atom, optionally substituted alkyl, optionally substituted aryl or optionally substituted heteroaryl is further preferable, and (It) a halogen atom or optionally substituted alkyl is most preferable.

In $R^8$, (Iu) optionally substituted alkyl or oxo is preferable, and (Iv) optionally substituted alkyl is further preferable.

In $R^9$, (Iw) carboxy or a carboxy-equivalent is preferable, and (Ix) carboxy is further preferable.

In M, (Iy) sulfonyl is preferable, and (Iz) sulfonyl is further preferable.

In Y, (IIa) a single bond or optionally substituted alkylene optionally containing one or two heteroatom(s) is preferable, and (IIb) a single bond is further preferable.

In $L^1$, (IIc) a single bond is preferable.

In $L^2$, (IId) a single bond is preferable.

In $L^3$, (IIe) optionally substituted alkylene optionally containing one or two heteroatom(s) is preferable, (IIf) optionally substituted alkylene is further preferable, and (IIg) methylene is most preferable.

In n, (IIh) 0 or 1 is preferable, and (IIi) 0 is further preferable.

In q, (IIj) 0, 1 or 2 is preferable, and (IIk) 0 or 1 is further preferable.

Preferable substituent groups of the ring C, the formula of —$X^1$=$X^2$—$X^3$=$X^4$—, $R^1$ to $R^5$, $R^{12}$ to $R^{14}$, Y, Z, $L^4$, n and q of the general formula (II) are shown below with (Id) above to (Iv) above, (Iy) above to (IIb) above, (IIh) above to (IIk) above and (Ill) to (IIm). The compounds with the possible combination thereof are preferable. The substituent of the general formula (II) is applicable for each corresponding substituent of the general formula (II-a) or (II-b).

In the ring C, (Id) above is preferable, (Ie) above is further preferable and (If) above is most preferable.

In the formula of —$X^1$=$X^2$—$X^3$=$X^4$—, (Ig) above is preferable and (Ih) above is further preferable.

In $R^1$, $R^2$, $R^4$ and $R^5$ each substituent is independent, and (Ii) above is preferable, (Ij) above is further preferable and (Ik) above is most preferable.

In $R^3$, (Il) above is preferable, (Im) above is further preferable and (In) above is most preferable.

In $R^{12}$, (Io) above is preferable, (Ip) above is further preferable and (Iq) above is most preferable.

In $R^{13}$, (Ir) above is preferable, (Is) above is further preferable and (It) above is most preferable.

In $R^{14}$, (Iu) above is preferable and (Iv) above is further preferable.

In M, (Iy) above is preferable and (Iz) above is further preferable.

In Y, (IIa) above is preferable and (IIb) above is further preferable.

In Z, (Ill) CH, C($R^{14}$) or N is preferable and (IIm) CH is further preferable.

In n, (IIh) above is preferable and (IIi) above is further preferable.

In q, (IIj) above is preferable and (IIk) above is further preferable.

Preferable substituent groups of the ring D, $R^{15}$ to $R^{21}$, M, Z, n and q of the general formula (III) are shown below with (Ie) above to (If) above, (Ii) above to (It) above, (Iy) above to (Iz) above and (IIh) above to (IIm) above. The compounds with the possible combination thereof are preferable. The substituent of the general formula (III) is applicable for each corresponding substituent of the general formula (III-b).

In the ring D, (Ie) above is preferable, (If) is further preferable.

In $R^{15}$, $R^{16}$, and $R^{18}$ each substituent is independent, and (Ii) above is preferable, (Ij) above is further preferable and (Ik) above is most preferable.

In $R^{17}$, (Il) above is preferable, (Im) above is further preferable and (In) above is most preferable.

In $R^{19}$, (Io) above is preferable, (Ip) above is further preferable and (Iq) above is most preferable.

In $R^{20}$, (Ir) above is preferable, (Is) above is further preferable and (It) above is most preferable.

In M, (Iy) CH, C($R^{14}$) or N is preferable and (Iz) CH is further preferable.

In Z, (Ill) CH, C($R^{14}$) or N is preferable and (IIm) CH is further preferable.

In n, (IIh) above is preferable and (IIi) above is further preferable.

In q, (IIj) above is preferable and (IIk) above is further preferable.

EFFECT OF INVENTION

The compounds of the present invention are useful as a therapeutic agent, especially for treating allergic diseases, since they have an excellent DP receptor antagonistic activity and high safety.

BEST MODE FOR CARRYING OUT THE INVENTION

The compounds of the present invention can be prepared by the method A, B, C and D set forth below according to methods of Bioorg. Med. Chem. Lett., 1992, 2, 1053; Journal of Medicinal Chemistry (1963), 6(5), 480-3; J. Org. Chem., 1991, 56, 4481; and Protective Groups in Organic Synthesis, Theodora W Green (John Wiley & Sons). In addition, a racemate or an optical isomer is included in chemical structures shown by the general formulae (I) to (XXII), (IV-I), (I-a), (II-a), (I-b), (II-b) and (III-b).

Method A is set forth below,

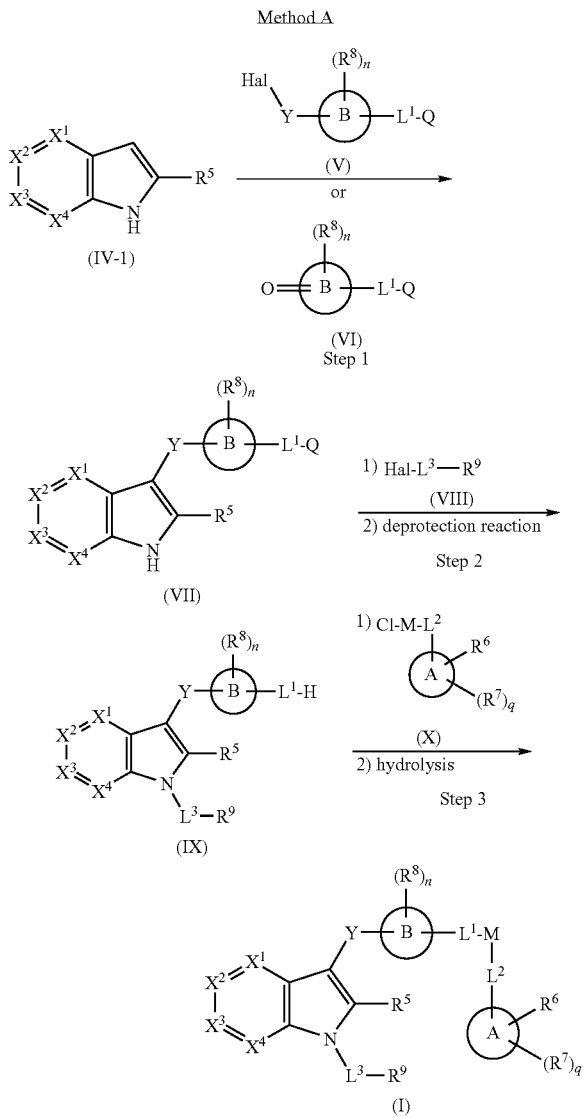

wherein the ring A and B, $X^1$, $X^2$, $X^3$, $X^4$, $R^5$, $R^6$, $R^7$, $R^8$, $R^9$, Y, M, $L^1$, $L^2$, $L^3$, n and q are the same as 1) above; Hal is a halogen atom, alkylsulfonyloxy or arylsulfonyloxy; and Q is a protecting group.

Step 1 is a process in which the compound of the formula (IV) is condensed with the compound of the formula (V) or (VI) to give the compound of the formula (VII).

The reaction can be carried out in a solvent by reacting 0.5-5.0 equivalents of the compound (V) or (VI) compared to the compound (IV) at 25° C. to a reflux temperature of the solvent for 5 minutes to 48 hours under the presence of a base.

Examples of the preferable base include sodium methoxide, sodium ethoxide, potassium carbonate, sodium carbonate and the like. 0.5-5.0 equivalents of the base can be used compared to the compound (IV).

Examples of the preferable solvent include methanol, ethanol, tetrahydrofuran, N,N-dimethylformamide and the like, which can be used alone or as a mixed solvent.

If necessary, reduction can be performed by hydrogenation under the presence of a catalyst such as 10% palladium carbon, for example.

Step 2 is a process in which the compound of the formula (VII) is condensed with the compound of the formula (VIII), and then the product is deprotected to give the compound of the formula (IX).

The condensation reaction can be carried out in a solvent by reacting 0.5-5.0 equivalents of the compound (VIII) compared to the compound (VII) at 0° C. to 100° C. for 5 minutes to 48 hours under the presence of a base.

Examples of the preferable base include sodium hydride, potassium hydride, potassium t-butoxide, potassium carbonate, cesium carbonate and the like. 0.5-5.0 equivalents of the base can be used compared to the compound (VII).

In addition, 0.1 to 1.0 equivalent of a phase transfer catalyst such as tetrabutylammonium chloride, tetrabutylammonium bromide, tetrabutylammonium iodide, benzyltriethylammonium chloride and benzyltributylammonium chloride etc., may be used.

Examples of the preferable solvent include pyridine, acetonitrile, methylene chloride, tetrahydrofuran, N,N-dimethylformamide, dimethylsulfoxide, acetone, methylethylketone, methylisobutylketone and the like, which can be used alone or as a mixed solvent containing water.

In the deprotecting reaction, Q of the protecting group is removed under usual deprotecting condition.

Step 3 is a process in which the compound of the formula (IX) is condensed with the compound of the formula (X), and then the product is hydrolyzed to give the compound of the formula (I).

The condensation reaction can be carried out in a solvent by reacting 0.5-5.0 equivalents of the compound (X) compared to the compound (IX) at 0° C. to 80° C. for 5 minutes to 48 hours.

The reaction may be carried out under the presence of one to five equivalent(s) of a base. Examples of the preferable base include triethylamine, pyridine, potassium carbonate, sodium carbonate, potassium bicarbonate, sodium bicarbonate, potassium hydroxide, sodium hydroxide and the like.

Examples of the preferable solvent include pyridine, acetonitrile, methylenechloride, tetrahydrofuran and the like, which can be used alone or as a mixed solvent containing water.

The hydrolysis reaction can be carried out by using 0.5-5.0 equivalents of the base compared to the compound (IX) in a solvent at 0° C. to 100° C. for 5 minutes to 48 hours.

Examples of the preferable base include sodium hydroxide, potassium hydroxide, and the like.

Examples of the preferable solvent include methanol, tetrahydrofuran and the like, which can be used alone or as a mixed solvent containing water.

Method B is set forth below,

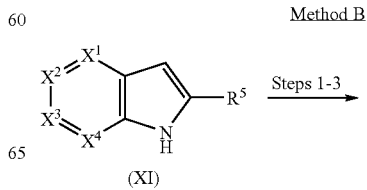

-continued

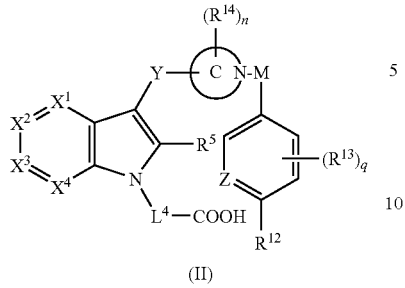

(II)

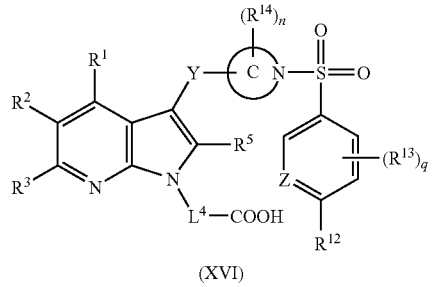

(XVI)

wherein the ring C, $X^1$, $X^2$, $X^3$, $X^4$, $R^{12}$, $R^{13}$, $R^{14}$, n and q are the same as 13) above.

The compound of the formula (II) can be prepared from the compound of the formula (XI) in the manner similar to the steps 1-3 of the method A Method C is set forth below, wherein the ring C, $R^1$, $R^2$, $R^3$, $R^5$, $R^{12}$, $R^{13}$, $R^{14}$, Y, n and Z are the same as 13) above; $R^{22}$ is C1-C6 alkyl; and Hal is a halogen atom, alkylsulfonyloxy or arylsulfonyloxy.

The compound of the formula (XII) prepared from the compound of the formula (XI) through a process similar to the step 1 of the method A can be used as a starting compound.

Step 1 is a process in which the compound of the formula (XII) is oxidized to give the compound of the formula (XIII).

The reaction can be carried out in a solvent by reacting 0.5-5.0 equivalents of a oxidizing agent compared to the compound (XII) at −20° C. to a reflux temperature of the solvent for 5 minutes to 48 hours.

Examples of the preferable oxidizing agent include m-chloroperbenzoic acid and the like.

Examples of the preferable solvent include methylenechloride, chloroform, toluene and the like, which can be used alone or as a mixed solvent.

Step 2 is a process in which the compound of the formula (XIII) is reacted with benzoyl bromide to give the compound of the formula (XIV).

The reaction can be carried out in a solvent by reacting 0.5-5.0 equivalents of benzoyl bromide compared to the compound (XIII) at 0° C. to a reflux temperature of the solvent for 5 minutes to 48 hours.

Examples of the preferable solvent include methylene chloride, chloroform, toluene, tetrahydrofuran, N,N-dimethylformamide and the like, which can be used alone or as a mixed solvent.

Step 3 is a process in which the compound of the formula (XIV) is hydrolyzed, and then condensed with the compound of the formula (VIII) to give the compound of the formula (XV).

The hydrolysis reaction can be carried out by using 0.5-5.0 equivalents of the base compared to the compound (XIV) in a solvent at 0° C. to 100° C. for 5 minutes to 48 hours.

Examples of the preferable base include lithium hydroxide, sodium hydroxide, potassium hydroxide and the like.

Examples of the preferable solvent include methanol, tetrahydrofuran and the like, which can be used alone or as a mixed solvent containing water.

The condensation reaction can be carried out in a solvent by reacting 0.5-5.0 equivalents of the compound (VIII) at 0° C. to 100° C. for 5 minutes to 48 hours under the presence of a base.

Examples of the preferable base include sodium hydride, potassium hydride, potassium t-butoxide, potassium carbonate, cesium carbonate and the like. 0.5-5.0 equivalents of the base can be used compared to the compound (VII).

In addition, 0.1 to 1.0 equivalent of a phase transfer catalyst such as tetrabutylammonium chloride, tetrabutylammonium

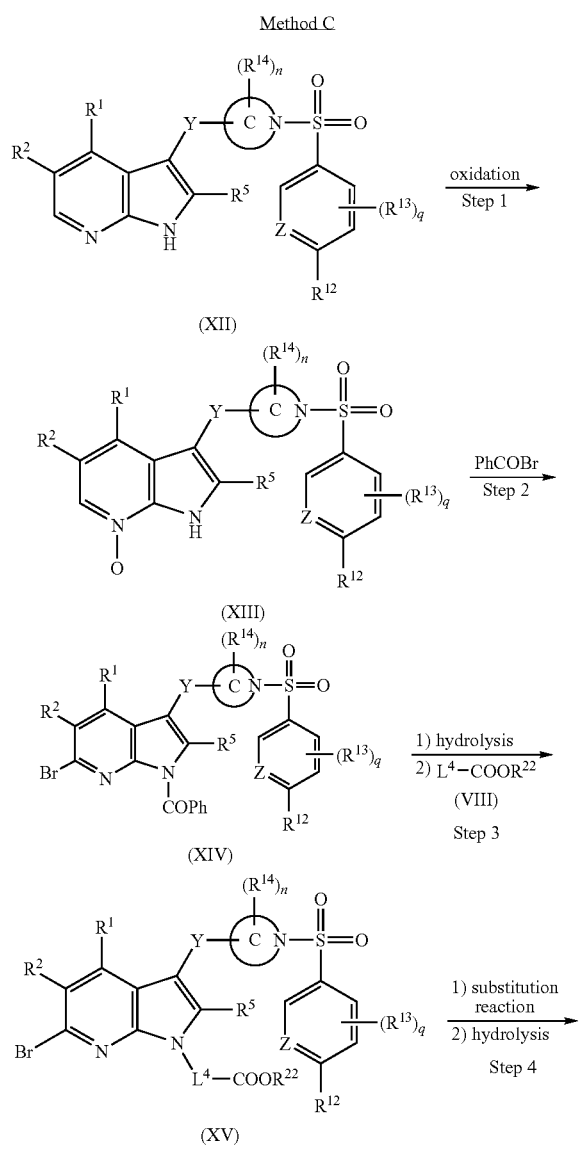

bromide, tetrabutylammonium iodide, benzyltriethylammonium chloride and benzyltributylammonium chloride etc., may be used.

Examples of the preferable solvent include pyridine, acetonitrile, methylene chloride, tetrahydrofuran, N,N-dimethylformamide, dimethylsulfoxide, acetone, methylethylketone, methylisobutylketone and the like, which can be used alone or as a mixed solvent containing water.

Step 4 is a process in which Br of the compound of the formula (XV) is substituted with $R^3$, and then the product is hydrolyzed to give the compound of the formula (XVI).

In the substitution reaction in which $R^3$ is aryl or heteroaryl, usual condition of Suzuki coupling reaction is applicable for the reaction.

In the substitution reaction in which $R^3$ is a electron-donating group such as alkyloxy or optionally substituted amino, the substitution reaction can be carried out in a solvent by using a metal salt of alcohol (e.g., methanol or ethanol), optionally substituted amino or a metal salt thereof as a nucleophile at 0° C. to 200° C. for 5 minutes to 48 hours.

Examples of the preferable solvent include alcohol such as methanol or ethanol, N,N-dimethylformamide, dioxane, toluene and the like, which can be used alone or as a mixed solvent containing water. If necessary, a sealed tube or a microwave is applicable for the reaction.

If $R^3$ is alkyl or alkoxycarbonyl etc., which is not available as a nucleophile in the substitution reaction, Br can be substituted by reacting with alkyl halide or dialkyl oxalate after the compound (XV) is lithiated by using n-BuLi for example.

The hydrolysis reaction can be carried out by using 0.5-5.0 equivalents of the base compared to the compound (XIV) in a solvent at 0° C. to 100° C. for 5 minutes to 48 hours.

Examples of the preferable base include lithium hydroxide, sodium hydroxide, potassium hydroxide, and the like.

Examples of the preferable solvent include methanol, tetrahydrofuran and the like, which can be used alone or as a mixed solvent containing water.

Method D is set forth below,

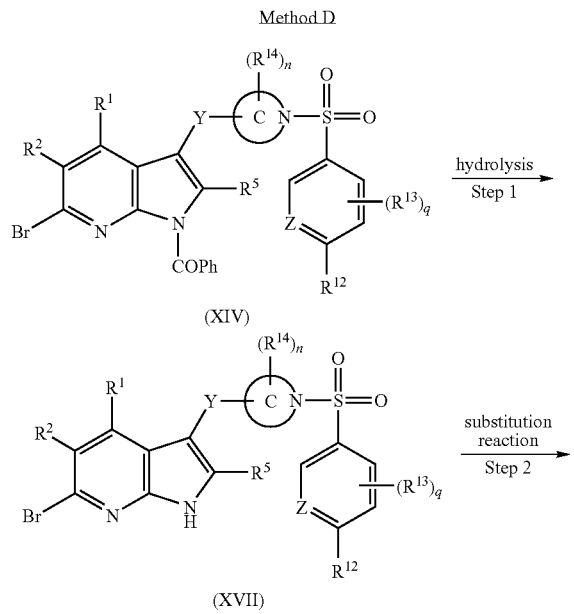

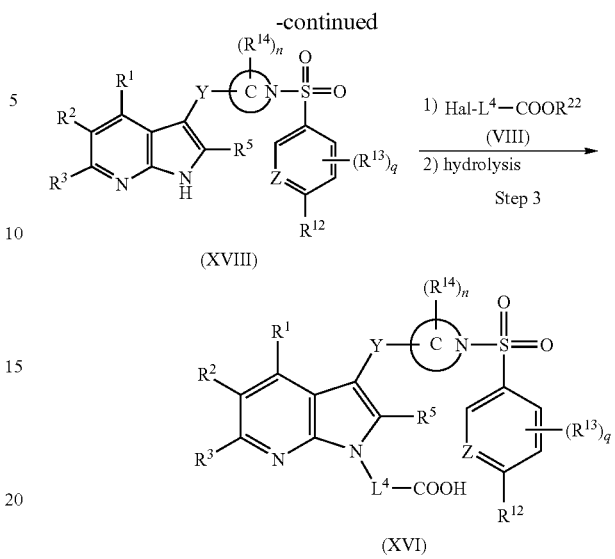

wherein the ring C, $R^1$, $R^2$, $R^3$, $R^5$, $R^{12}R^{13}R^{14}$, Y, Z, $L^4$, n and q are the same as 13) above; $R^{22}$ is C1-C6 alkyl; and Hal is a halogen atom, alkylsulfonyloxy or arylsulfonyloxy.

Step 1 is a process in which the compound of the formula (XIV) is hydrolyzed to give the compound of the formula (XVII).

The hydrolysis reaction can be carried out by using 0.5-5.0 equivalents of the base compared to the compound (XIV) in a solvent at 0° C. to 100° C. for 5 minutes to 48 hours.

Examples of the preferable base include lithium hydroxide, sodium hydroxide, potassium hydroxide, and the like.

Examples of the preferable solvent include methanol, tetrahydrofuran and the like, which can be used alone or as a mixed solvent containing water.

Step 2 is a process in which Br of the compound of the formula (XVII) is substituted with $R^3$ to give the compound of the formula (XVIII).

In the substitution reaction in which $R^3$ is aryl or heteroaryl, usual condition of Suzuki coupling reaction is applicable for the reaction.

In the substitution reaction in which $R^3$ is a electron-donating group such as alkyloxy or optionally substituted amino, the substitution reaction can be carried out in a solvent by using a metal salt of alcohol (e.g., methanol or ethanol), optionally substituted amino or a metal salt thereof as a nucleophile at 0° C. to 200° C. for 5 minutes to 48 hours.

Examples of the preferable solvent include alcohol such as methanol or ethanol, N,N-dimethylformamide, dioxane, toluene and the like, which can be used alone or as a mixed solvent containing water. If necessary, a sealed tube or a microwave is applicable for the reaction.

If $R^3$ is alkyl or alkoxycarbonyl etc., which is not available as a nucleophile in the substitution reaction, Br can be substituted by reacting with alkyl halide or dialkyl oxalate after the compound (XVII) is lithiated by using n-BuLi for example.

Step 3 is a process in which the compound of the formula (XVIII) is condensed with the compound of the formula (VIII), and then hydrolyzed to give the compound of the formula (XVI).

The condensation reaction can be carried out in a solvent by reacting 0.5-5.0 equivalents of the compound (VIII) compared to the compound (XVIII) at 0° C. to 100° C. for 5 minutes to 48 hours under the presence of a base.

Examples of the preferable base include sodium hydride, potassium hydride, potassium t-butoxide, potassium carbonate, cesium carbonate and the like. 0.5-5.0 equivalents of the base can be used compared to the compound (XVIII).

In addition, 0.1 to 1.0 equivalent of a phase transfer catalyst such as tetrabutylammonium chloride, tetrabutylammonium bromide, tetrabutylammonium iodide, benzyltriethylammonium chloride and benzyltributylammonium chloride etc., may be used.

Examples of the preferable solvent include pyridine, acetonitrile, methylene chloride, tetrahydrofuran, N,N-dimethylformamide, dimethylsulfoxide, acetone, methylethylketone, methylisobutylketone and the like, which can be used alone or as a mixed solvent containing water.

The hydrolysis reaction can be carried out by using 0.5-5.0 equivalents of the base compared to the compound (XVIII) in a solvent at 0° C. to 100° C. for 5 minutes to 48 hours.

Examples of the preferable base include lithium hydroxide, sodium hydroxide, potassium hydroxide, and the like.

Examples of the preferable solvent include methanol, tetrahydrofuran and the like, which can be used alone or as a mixed solvent containing water.

6-Substituted-7-azaindole is a known compound or available as set forth below,

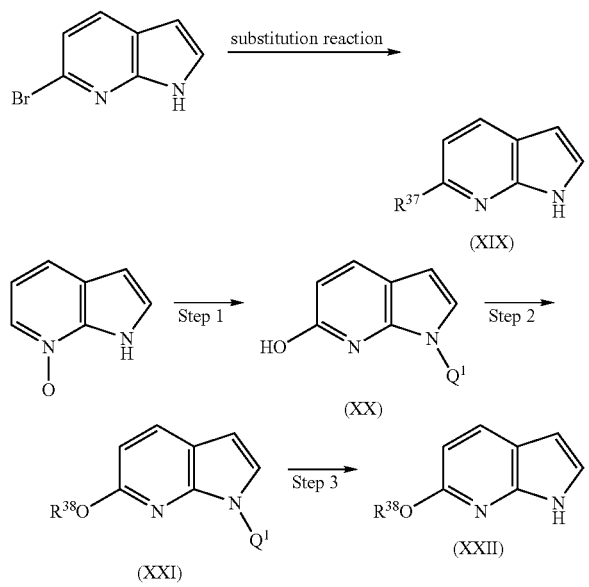

wherein $R^{37}$ is optionally substituted alkyl, optionally substituted alkyloxy, optionally substituted amino, acyl, optionally substituted carbamoyl, cyano, nitro, optionally substituted aryl, optionally substituted heteroaryl or optionally substituted non-aromatic heterocyclic group; $R^{38}$ is optionally substituted alkyl; and $Q^1$ is acyl.

The compound of the formula (XIX) can be prepared by substituting Br of 6-bromo-7-azaindole with $R^{37}$.

In the substitution reaction in which $R^{37}$ is aryl or heteroaryl, usual condition of Suzuki coupling reaction is applicable for the reaction.

In the substitution reaction in which $R^{37}$ is a electron-donating group such as alkyloxy or optionally substituted amino, the substitution reaction can be carried out in a solvent by using a metal salt of alcohol (e.g., methanol or ethanol), optionally substituted amino or a metal salt thereof as a nucleophile at 0° C. to 200° C. for 5 minutes to 48 hours.

Examples of the preferable solvent include alcohol such as methanol or ethanol, N,N-dimethylformamide, dioxane, toluene and the like, which can be used alone or as a mixed solvent containing water. If necessary, a catalysis (e.g., palladium catalysis, cupper catalysis etc.) and/or a base may be added and a sealed tube or a microwave may be used for the reaction.

If $R^{37}$ is alkyl or alkoxycarbonyl etc., which is not available as a nucleophile in the substitution reaction, Br can be substituted by reacting with alkyl halide or dialkyl oxalate after 6-bromo-7-azaindole is lithiated by using n-BuLi for example.

Step 1 is a process in which the compound of the formula (XX) is prepared by a rearrangement reaction of 7-azaindole-7-oxide.

The rearrangement reaction can be carried out in a solvent at 0° C. to 250° C. for 5 minutes to 48 hours.

Examples of the preferable solvent include acetic anhydride, propionic anhydride, benzoic anhydride and the like.

If necessary, the acylated hydroxy group may be deacylated using trifluoroacetic acid.

Step 2 is a process in which the compound of the formula (XXI) is prepared by alkylation reaction of the compound of the formula (XX).

The alkylation reaction can be carried out in a solvent at 0° C. to 250° C. for 5 minutes to 48 hours under the presence of a base.

Examples of the preferable solvent include N,N-dimethylformamide, dimethylsulfoxide, tetrahydrofuran and the like.

Examples of the preferable base include cesium carbonate, sodium carbonate, potassium carbonate, sodium hydroxide and the like, and one to three equivalent(s) compared to the compound of the formula (XX) can be used.

Examples of the preferable alkylation agent include methyl bromide, methyl iodide, methyl tosylate, methyl mesylate, methyl triflate, dimethyl sulfate, ethyl iodide, 1-iodopropane, 2-iodopropane, 1-iodobutane, 2-iodobutane, 2-methyl-1-iodopropane, benzyl bromide, 2-methyloxy-1-bromoethane and the like, and 0.8-2 equivalents of the agent compared to the compound (XX) can be used.

Step 3 is a process in which the compound of the formula (XXII) is prepared by deacylation reaction of the compound of the formula (XXI).

The deacylation reaction can be carried out in a solvent at 0° C. to 250° C. for 5 minutes to 48 hours under the presence of a base.

Examples of the preferable solvent include methanol, ethanol, tetrahydrofuran and the like, which can be used alone or as a mixed solvent containing water.

Examples of the preferable base include lithium hydroxide, sodium hydroxide, potassium hydroxide and the like, and one to three equivalent(s) of the base compared to the compound of the formula (XX) can be used.

In this specification, a term of "solvate" includes, for example, a solvate with an organic solvent, a hydrate and the like. In a case of forming the solvate with an organic solvent, any number of molecules of the organic solvent may coordinated. In a case of forming the hydrate, any number of water molecules may be coordinated. A hydrate is usually preferred.

A term of "compound of the present invention" includes a pharmaceutically acceptable salt and a solvate thereof. Examples of the salt include salts with alkaline metal (lithium, sodium and potassium etc.), alkaline earth metal (magnesium and calcium etc.), ammonium, organic bases and amino acids and salts with inorganic acids (hydrochloric acid, hydrobromic acid, phosphoric acid and sulfuric acid, etc.) and organic acids (acetic acid, citric acid, maleic acid, fumaric acid, benzenesulfonic acid and p-toluenesulfonic acid etc.). These salts can be formed by the usual method A compound of the present invention is not limited to the specified isomer but includes all possible isomers and racemates.

A compound of the present invention shows an excellent DP receptor antagonistic activity as described in the following examples. Accordingly, a pharmaceutical composition of the present invention can be used as a therapeutic agent for preventing and/or treating allergic diseases such as asthma, allergic rhinitis, allergic dermatitis, allergic conjunctivitis, food allergy and the like; systemic mastocytosis; systemic disorder of mastcell-activation; lung emphysema; chronic bronchitis; chronic obstructive lung disease; skin disorder characterized by pruritus such as atopic dermatitis and hives; diseases occurring secondarily due to behavior accompanied by pruritus such as cataract and retinal detachment; brain damages such as cerebrovascular disorder, degenerative brain disorder and demyelinating disease; sleep-waking disorder; Churg-Strauss syndrome; papular dermatitis such as filariasis; vasculitis; polyarteritis; cutaneous eosoiophilic granuloma; autoimmune diseases such as multiple sclerosis and transplant rejection; eosoiophilic pneumonopathy; histiocytosis; pneumonia; aspergillosis; pleurisy; sarcoidosis; pulmonary fibrosis; eosinophilia; skin flush such as face flush by nicotinic acid; filariasis; schistosomiasis; trichinelliasis; coccidioidomycosis; tuberculosis; bronchial cancer; lymphoma; Hodgkin's disease and the like.

When a compound of the present invention is administered to a human in order to treat the diseases above, oral administration through a powder, granule, tablet, capsule, pill, liquid formulation and the like, or parenteral administration through an injection, suppository, transdermal formulation, inhalant and the like is possible.

A pharmaceutical composition can be obtained by mixing a therapeutically effective amount of a compound of the present invention with a pharmaceutical additives such as an excipient, binder, wetting agent, disintegrating agent, lubricant and the like, which is suitable to the selected formulation. An injection can be formulated by sterilization together with a suitable carrier.

In the treatment of the diseases related to PGD2 receptor above, it is possible to use the compound of the present invention combined with or in a coupled formulation with the other therapeutic agent. In the case of treating inflammatory diseases including allergy, the compound can be used combined with or in a coupled formulation with leukotriene receptor antagonist (e.g., montelukast sodium, zafirlukast, pranlukast hydrate, leukotriene B4 receptor antagonist); leukotriene synthesis inhibitor such as zileuton, PDE IV inhibitor (e.g., theophylline, cilomilast, roflumilast), corticosteroid (e.g., prednisolone, fluticasone, budesonide, ciclesonide), β2-agonist (e.g., salbutamol, salmeterol, formoterol), anti IgE antibody (e.g., omalizumab), histamine H1 receptor antagonist (e.g., chlorpheniramine, loratadine, cetirizine), immunosuppressant (tacrolimus, cyclosporin), thromboxane A2 receptor antagonist (e.g., ramatroban), chemokine receptor (especially CCR-1, CCR-2, CCR-3) antagonist, other prostanoid receptor antagonist (e.g., CRTH2 antagonist), adhesive molecule (e.g., VLA-4 antagonist), cytokine antagonist (e.g., anti-IL-4 antibody, anti-IL-3 antibody), Non-steroidal anti-inflammatory agent (e.g., propionic acid derivative such as ibuprofen, ketoprofen, and naproxen etc.; acetic acid derivative such as indomethacin, and diclofenac etc.; salicylic acid such as acetyl salicylic acid; cyclooxigenase-2 inhibitor such as celecoxib and etoricoxib).

Further, uses combined with or in a coupled formulation with antitussive agent (e.g., codein, hydrocodein), cholesterol lowering agent (lovastatin, simvastatin, fluvastatin, rosuvastatin), anticholinergic drug (e.g., tiotropium, ipratropium, flutropium, oxitropium) are also possible.

Dose of the compounds of the present invention depends on condition of diseases, route of administration, age and body weight of a patient. In the case of oral administration to an adult, the dose range is usually 0.1 to 100 mg/kg/day, preferably 1 to 20 mg/kg/day.

EXAMPLES

The present invention is illustrated more in detail below by examples and test examples, but not limited to these examples.

In examples, the following abbreviations are used;

| | |
|---|---|
| Me: | methyl |
| Et: | ethyl |
| n-Pr: | n-propyl |
| i-Pr: | isopropyl |
| n-Bu: | n-butyl |
| i-Bu: | i-butyl |
| s-Bu: | sec-butyl |
| Ph: | phenyl |
| Ac: | acetyl |
| Boc: | t-butoxycarbonyl |
| SEM: | 2-(trimethylsilyl)ethoxymethyl |
| DMF: | N,N-dimethylformamide |
| THF: | tetrahydrofuran |

Example 1

Preparation of the Compound E4

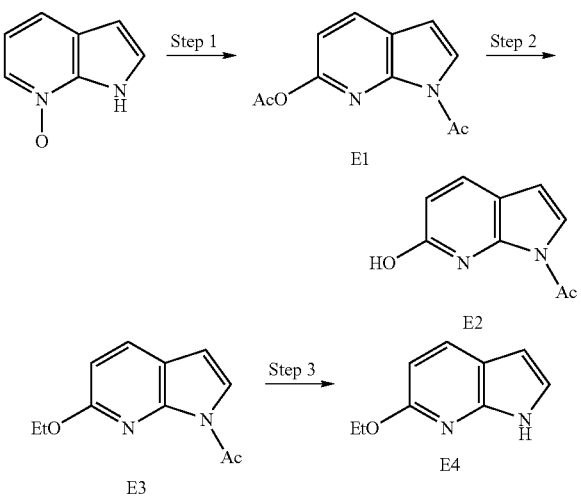

Step 1

A solution of 7-azaindole-7-oxide (1.00 g, 7.45 mmol) in acetic anhydride (20 ml) was heated under reflux for 4 hours and acetic anhydride was evaporated in vacuo. The resulting residue was purified with a silica gel column chromatography. The obtained crystalline was washed with isopropyl ether to give the compound E1 (609 mg, 37% yield).

$^1$H-NMR (CDCl$_3$) δ ppm: 2.38 (3H, s), 3.00 (3H, s), 6.62 (1H, d, J=4.1 Hz), 6.96 (1H, d, J=8.2 Hz), 7.96 (1H, d, J=8.2 Hz), 7.97 (1H, d, J=4.1 Hz).

Step 2

To a solution of the compound E1 (437 mg, 2.00 mmol) in methylene chloride (5 mL) under ice-cooling was added trifluoroacetic acid (3 mL) and the mixture was stirred at room temperature for 1 hour. Trifluoroacetic acid (2 mL) was further added and the mixture was stirred at room temperature for additional 1 hour. pH of the solution was adjusted to 9 by adding an aqueous solution of sodium bicarbonate and the mixture was extracted with ethyl acetate. The organic layer was washed with an aqueous solution of sodium bicarbonate, dried over sodium sulfate and concentrated in vacuo. The resulting residue was purified with a silica gel column chromatography to give the compound E2 (156 mg, 44% yield) and the unreacted compound E1 (164 mg, 38%).

$^1$H-NMR (CDCl$_3$) δ ppm: 2.69 (3H, s), 6.47 (1H, d, J=3.8 Hz), 6.53 (1H, d, J=9.2 Hz), 7.12 (1H, br s), 7.67 (1H, d, J=9.2 Hz).

Step 3

To a solution of the compound E2 (281 mg, 1.6 mmol) in DMF (3 mL) were added ethyl iodide (300 mg, 1.6 mmol) and cesium carbonate (780 mg, 1.92 mmol) and the mixture was stirred at room temperature for 30 minutes. pH of the reaction solution was adjusted to 4 by adding a 1M aqueous solution of citric acid (4 mL, 4 mmol). Water (30 mL) was added to the reaction solution and the precipitated crystalline was filtered, washed with water and dried to give the compound E3 (277 mg, 91% yield).

$^1$H-NMR (CDCl$_3$) δ ppm: 1.44 (3H, t, J=7.2 Hz), 3.00 (3H, s), 4.39 (2H, q, J=7.2 Hz), 6.51 (1H, d, J=4.2 Hz), 6.67 (1H, d, J=8.4 Hz), 7.75 (1H, d, J=8.4 Hz), 7.77 (1H, d, J=3.9 Hz).

Step 4

To a solution of the compound E3 (190 mg, 1 mmol) in MeOH (2 mL) and THF (2 mL), a 1M aqueous solution of LiOH (1.5 mL, 1.5 mmol) and the mixture was stirred at room temperature for 15 minutes. pH of the solution was adjusted to 4 by adding a 1M aqueous solution of citric acid (2 mL). The reaction solution was concentrated in vacuo and water (20 mL) was added to the residue. The precipitated crystalline was filtered, washed with water and dried to give the compound E4 (146 mg, 87% yield).

$^1$H-NMR (CDCl$_3$) δ ppm: 1.44 (3H, t, J=7.2 Hz), 4.38 (2H, q, J=7.2 Hz), 6.41-6.43 (1H, m), 6.58 (1H, d, J=8.7 Hz), 7.06-7.08 (1H, m), 7.82 (1H, d, J=8.4 Hz), 8.95 (1H, br).

The following compound E5-E12 can be prepared in the same manner described above.

TABLE 1

| No. compound | Structure |
|---|---|
| E5 | MeO-[7-azaindole] |
| E6 | n-PrO-[7-azaindole] |
| E7 | i-PrO-[7-azaindole] |
| E8 | n-BuO-[7-azaindole] |
| E9 | i-BuO-[7-azaindole] |
| E10 | s-BuO-[7-azaindole] |
| E11 | BnO-[7-azaindole] |
| E12 | MeOCH$_2$CH$_2$O-[7-azaindole] |

Example 2

Preparation of the Compound I-4

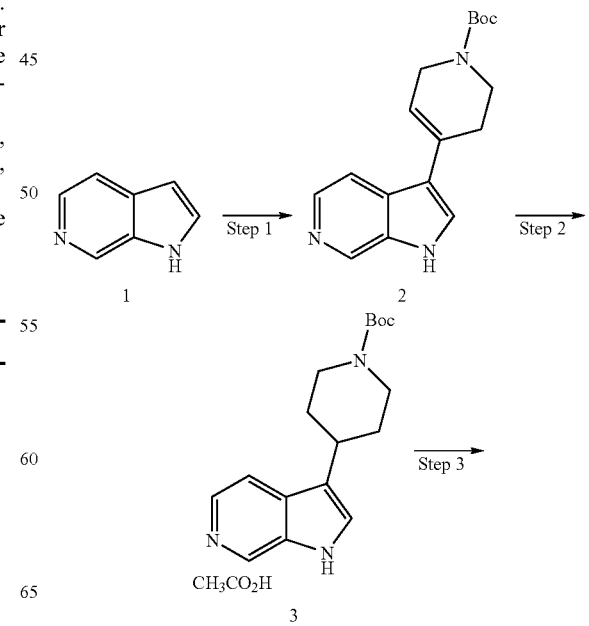

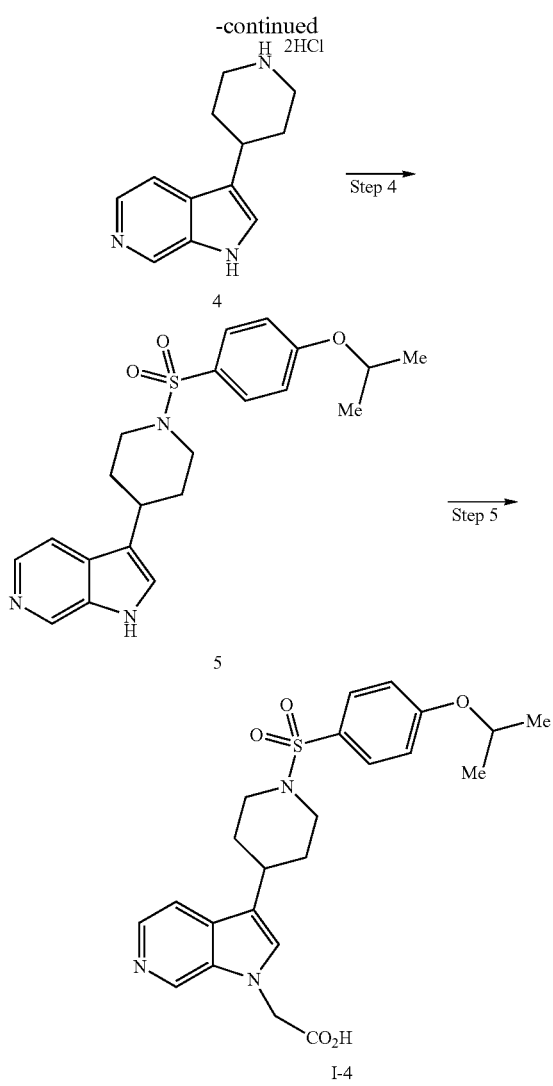

Step 1

To a solution of the compound (1) (2.0 g, 16.9 mmol) in methanol (20 mL), were added 1-(t-butoxycarbonyl)-4-piperidone (6.73 g, 33.8 mmol) and a 28% methanol solution of sodium methoxide (20 mL, 0.1 mmol) and the solution was heated under reflux for 7 hours. The reaction mixture was poured into 100 mL of ice-water, extracted with ethyl acetate and the organic layer was washed with water, dried and concentrated. The resulting residue was crystallized from hexane-ethyl acetate to give the compound (2) (2.47 g, 49% yield).

$^1$H-NMR (CDCl$_3$) δ ppm: 1.51 (s, 9H), 2.58 (m, 2H), 3.69 (t, 2H, J=5.7 Hz), 4.15 (d, 2H, J=2.7 Hz), 6.16 (s, 1H), 7.42 (s, 1H), 7.79 (d, 1H, J=5.7 Hz), 8.27 (d, 1H, J=5.7 Hz), 8.86 (s, 1H).

Step 2

The compound (2) (1.05 g, 3.5 mmol) was dissolved in methanol (20 mL) and acetic acid (1 mL), and stirred under hydrogen atmosphere in the presence of 10% palladium carbon for 3 hours. The reaction mixture was filtered through Celite and the filtrate was condensed. The obtained crystalline was filtered and dried to give the compound (3) (1.18 g, 93% yield).

$^1$H-NMR (CDCl$_3$) δ ppm: 1.49 (s, 9H), 1.61-2.02 (m, 4H), 2.16 (s, 3H), 2.85-3.04 (m, 3H), 4.26 (m, 2H), 7.49 (s, 1H), 7.69 (d, 1H, J=5.7 Hz), 8.08 (d, 1H, J=5.7 Hz), 9.20 (s, 1H).

Step 3

5N Hydrochloric acid (3.2 mL) was added to a solution of the compound (3) (1.16 g, 3.22 mmol) and the mixture was stirred for an hour. A 2N aqueous solution of sodium hydroxide (10 mL) was added to the reaction mixture under ice cooling and the oily product was obtained. Ethyl acetate was added to the oily product and the resulting crystalline was filtered and dried to give the compound (4) (0.7 g, 80% yield).

$^1$H-NMR (DMSO-d$_6$) δ ppm: 1.53-1.88 (m, 4H), 2.61-3.11 (m, 5H), 7.32 (s, 1H), 7.53 (d, 1H, J=5.4 Hz), 8.02 (d, 1H, J=5.4 Hz), 8.68 (s, 1H), 11.54 (brs, 1H).

Step 4

To a solution of the compound (4) (564 mg, 2.0 mmol) in pyridine (3 mL), was added 4-isopropoxybenzenesulfonyl chloride (326 mg, 1.39 mmol) and the mixture was stirred at room temperature for 1.5 hours. The reaction mixture was diluted with water, extracted with ethyl acetate and the organic layer was washed with diluted hydrochloric acid and water successively, dried and concentrated. The resulting crystalline was filtered and dried to give the compound (5) (256 mg, 32% yields).

$^1$H-NMR (CDCl$_3$) δ ppm: 1.39 (d, 6H, J=6.3 Hz), 1.81-1.96 (m, 2H), 2.08 (brd, 2H), 2.48 (brt, 2H), 2.78 (m, 1H), 3.92 (brd, 2H), 4.65 (m, 1H), 6.97 (d, 2H, J=8.7 Hz), 7.24 (s, 1H), 7.48 (d, 1H, J=5.4 Hz), 7.77 (d, 2H, J=8.7 Hz), 8.17 (d, 1H, J=5.7 Hz), 8.87 (s, 1H).

Step 5

To a solution of the compound (5) (251 mg, 0.62 mmol) in N,N-dimethylformamide (3 mL), were added cesium carbonate (0.41 g, 1.26 mmol) and methyl bromoacetate (119 μL, 1.26 mmol) and the mixture was stirred for an hour. The reaction solution was diluted with water, extracted with ethyl acetate and the extract was washed with water, dried and concentrated. The resulting residue was purified with a silica gel column chromatography (hexane:ethyl acetate=2:1). The product was dissolved in methanol (1.0 mL) and tetrahydrofuran (0.5 mL). A 1M aqueous solution of sodium hydroxide (0.49 mL, 0.49 mmol) was added to the solution and stirred at room temperature for 2 hours. The reaction solution was diluted with water and acidified by adding diluted hydrochloric acid. The product was extracted with ethyl acetate and the extract was washed with water, dried and concentrated. The residue was crystallized from hexane-ethyl acetate to give the compound I-4 (57 mg, 21% yield).

mp. 262-266° C., $^1$H-NMR (DMSO-d$_6$) δ ppm: 1.32 (d, 6H, J=6.0 Hz), 1.58-1.74 (m, 2H), 2.00 (brd, 2H), 2.37 (brt, 2H), 2.78 (m, 1H), 3.76 (brd, 2H), 4.76 (m, 1H), 5.06 (s, 2H), 7.15 (d, 2H, J=8.7 Hz), 7.35 (s, 1H), 7.51 (d, 1H, J=5.7 Hz), 7.68 (d, 2H, J=8.7 Hz), 8.07 (d, 1H, J=5.7 Hz), 8.72 (s, 1H).

Example 3

Preparation of the Compound I-13

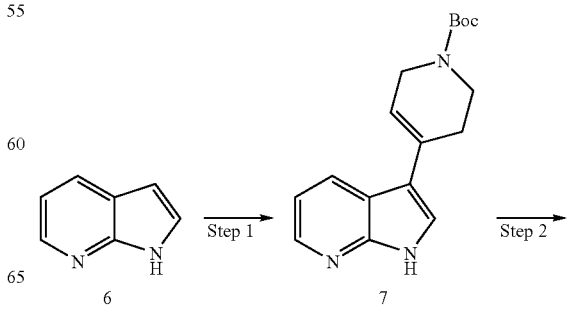

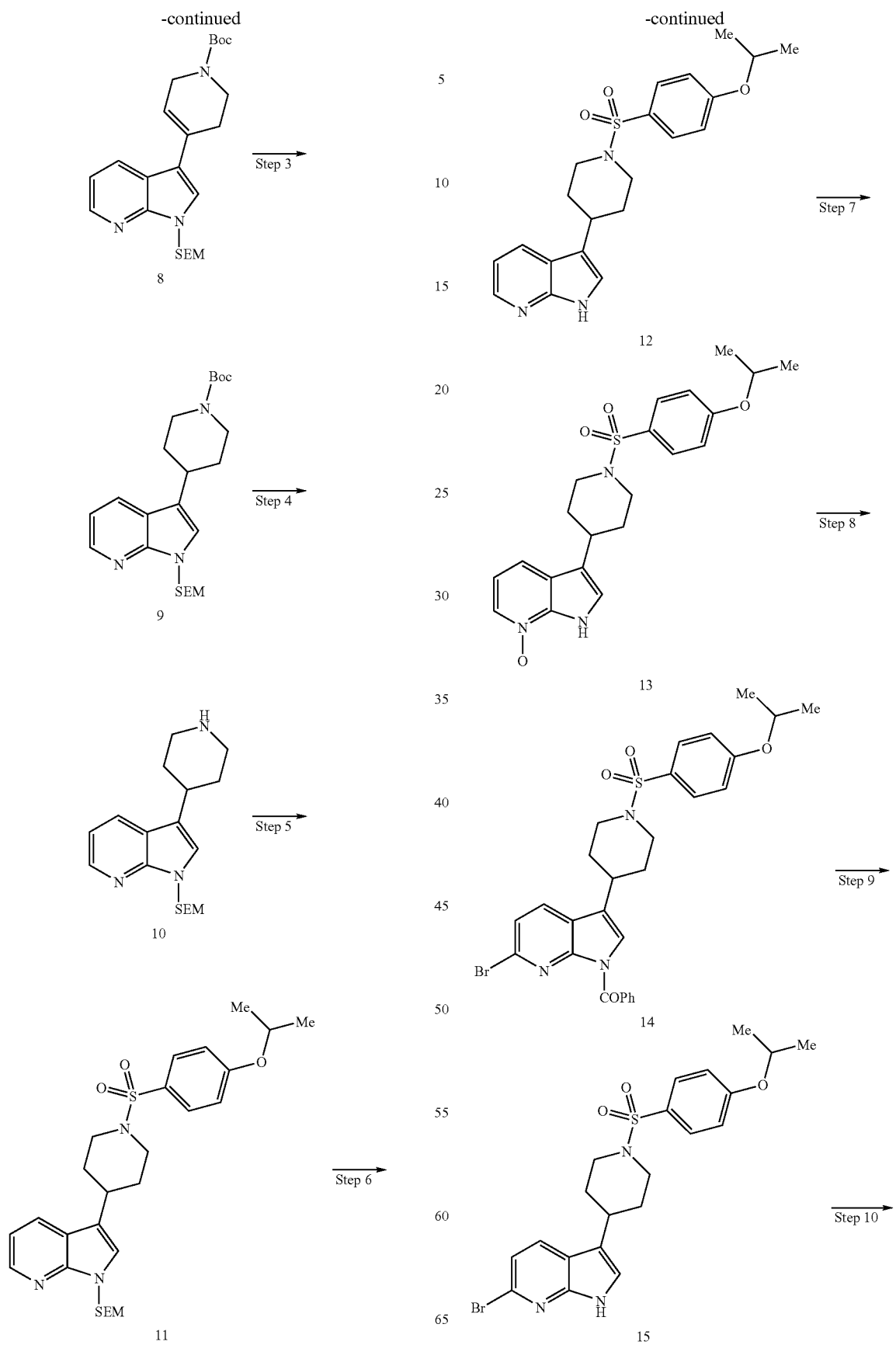

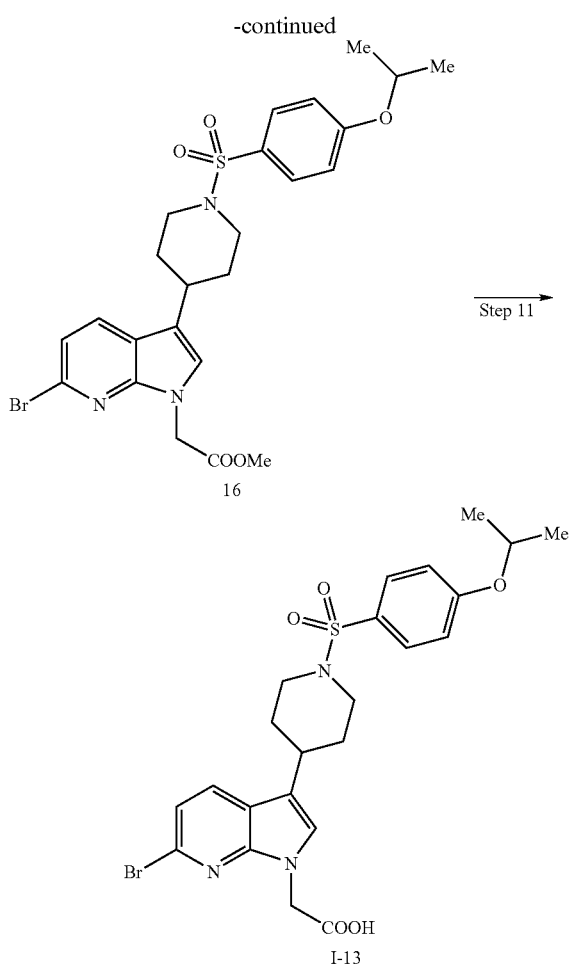

Step 1

To a solution of the compound (6) (5.0 g, 42.3 mmol) in methanol (50 mL) were added 1-(t-butoxycarbonyl)-4-piperidone (16.9 g, 84.6 mmol) and a 28% methanol solution of sodium methoxide (50 mL, 0.25 mmol) and the solution was heated under reflux for 2.5 hours. The reaction solution was poured into 100 mL of ice water, extracted with ethyl acetate and the organic layer was washed with water, dried and concentrated. The resulting residue was crystallized from hexane-ethyl acetate to give the compound (7) (9.23 g, 73% yield).

$^1$H-NMR (CDCl$_3$) δ ppm: 1.51 (s, 9H), 2.57 (s, 2H), 3.61-3.71 (m, 2H), 4.14-4.24 (m, 2H), 6.15 (s, 1H), 7.13-7.18 (m, 1H), 7.40 (s, 1H), 8.22 (d, 1H, J=9.3 Hz), 8.32-8.34 (m, 1H), 10.2 (br, 1H).

Step 2

The compound (7) (10.5 g, 35.1 mmol) was added to a solution of 60% sodium hydride (1.7 g, 42.5 mmol) in N,N-dimethylformamide (60 mL) at 0° C. and stirred under nitrogen atmosphere for 0.5 hours. To the reaction solution was added 2-(trimethylsilyl)ethoxymethyl chloride (6.43 g, 38.5 mmol) at −10° C. and the mixture was stirred at room temperature for 45 minutes. The reaction mixture was poured into 100 mL of water, extracted with ethyl acetate and the organic layer was washed with water, dried and concentrated to give the compound (8) (15.05 g, 99.9% yield).

$^1$H-NMR (CDCl$_3$) δ ppm: 0.96-1.01 (m, 2H), 1.57 (s, 9H), 2.62 (br, 2H), 3.58-3.63 (m, 2H), 3.75 (t, 2H, J=6 Hz), 5.74 (s, 2H), 6.20 (br, 2H), 7.17-7.22 (m, 1H), 1.38 (s, 1H), 8.22 (d, 1H, J=8.1 Hz), 8.40 (d, 1H, J=4.8 Hz).

Step 3

The compound (8) (20.08 g, 46.8 mmol) was dissolved in methanol (250 mL) and stirred under hydrogen atmosphere in the presence of 10% palladium carbon (2.5 g) for 18 hours. The reaction mixture was filtered through Celite and the filtrate was concentrated to give the compound (9) (20.18 g, 99.9% yield).

$^1$H-NMR (CDCl$_3$) δ ppm: 0.95-1.00 (m, 2H), 1.56 (s, 9H), 1.65-1.80 (m, 4H), 2.07-2.12 (m, 2H), 3.61 (t, 2H, J=8.4 Hz), 4.35-4.80 (br, 2H), 5.71 (s, 2H), 7.12-7.17 (m, 3H), 7.98 (d, 1H, J=7.8 Hz), 8.38 (d, 1H, J=4.5 Hz).

Step 4

100 mL of 4N hydrochloric acid/1,4-dioxane was added to the compound (9) (37.47 g, 86.9 mmol) and stirred at room temperature for 18 hours. After the reaction solution was condensed, ethyl acetate and a saturated aqueous solution of sodium bicarbonate were added and the mixture was extracted. The organic layer was washed with water, dried and concentrated. The oily product was crystallized by adding diethylether and filtered, dried to give the compound (10) (15 g, 50% yield).

$^1$H-NMR (CDCl$_3$) δ ppm: 0.97 (t, 2H, J=7.2 Hz), 3.18-3.21 (m, 2H), 3.59-3.66 (m, 4H), 5.76 (s, 2H), 7.28-7.31 (m, 2H), 8.28 (d, 1H, J=7.8 Hz), 8.40 (d, 1H, J=7.5 Hz).

Step 5

4-Propoxybenzenesulfonyl chloride (2.46 g, 10.5 mmol) was added to a solution of the compound (10) (3.45 g, 10.0 mmol) and triethylamine (2.02 g, 20.0 mmol) in N,N-dimethylformamide (20 mL) and stirred at room temperature for 0.5 hours. Ethyl acetate and a saturated sodium bicarbonate aqueous solution were added to the reaction solution and the mixture was extracted. The organic layer was washed with brine, dried and concentrated. The resulting residue was purified by a silica gel column chromatography (hexane:ethyl acetate=2:1) and the crystalline obtained after concentration was filtered and dried to give the compound (11) (3.2 g, 59% yield).

$^1$H-NMR (CDCl$_3$) δ ppm: 0.97 (t, 2H, J=8.4 Hz), 1.47 (d, 6H, J=6 Hz), 1.90-2.05 (m, 2H), 2.12-2.15 (m, 2H), 2.47-2.53 (m, 2H), 4.70-4.76 (m, 1H), 5.70 (s, 2H), 7.05-7.16 (m, 4H), 7.79-7.82 (m, 2H), 7.88 (d, 1H, J=7.8 Hz), 8.38 (d, 1H, J=4.8 Hz).

Step 6

A 1M solution of tetra-n-butylammonium fluoride (270 mL) was added to a solution of the compound (11) (20.0 g, 36.8 mmol) in tetrahydrofuran (200 mL) and heated with stirring for 8 hours. The reaction solution was concentrated, ethyl acetate and a saturated ammonium chloride aqueous solution was added and the mixture was extracted. The organic layer was washed with brine, dried and concentrated. Ethyl acetate was added to the oily residue and the obtained crystalline was filtered, dried to give the compound (12) (11.9 g, 81% yield).

$^1$H-NMR (CDCl$_3$) δ ppm: 1.31 (d, 6H, J=5.7 Hz), 1.65-1.75 (m, 2H), 1.98-2.01 (m, 2H), 2.33-2.38 (m, 2H), 2.65-2.70 (m, 1H), 3.72 (d, 2H, J=11.4 Hz), 4.73-4.78 (m, 1H), 6.65-6.99 (m, 1H), 7.14-7.21 (m, 3H), 7.67-7.70 (m, 2H), 7.90 (d, 1H, J=8.1 Hz), 8.16 (d, 1H, J=1.8 Hz), 11.34 (s, 1H).

Step 7 m-Chloroperbenzoic acid (0.43 g, 2.51 mmol) was added to a solution of the compound (12) (665 mg, 1.67 mmol) in dichloromethane (30 mL) at −5° C. and stirring was continued for an hour. A saturated sodium bicarbonate aqueous solution was added to the reaction mixture and extracted with chloroform. The organic layer was washed with water, dried and concentrated. The resulting residue was purified by a silica gel column chromatography (ethyl acetate:methanol=9:1) and the concentrated residue was crystallized by adding ethyl acetate to give the compound (13) (520 mg, 74% yield).

$^1$H-NMR (CDCl$_3$) δ ppm: 1.38 (d, 6H, J=6.3 Hz), 1.83-2.05 (m, 6H), 2.38-2.46 (m, 2H), 2.62-2.72 (m, 1H), 3.80 (d, 2H, J=12.3 Hz), 4.60-4.67 (m, 1H), 6.96-7.05 (m, 3H), 7.26 (s, 1H), 7.60 (d, 1H, J=9.9 Hz), 7.69-7.72 (m, 2H), 8.18 (d, 1H, J=6.3 Hz), 12.40 (br, 1H).

Step 8

Benzoyl bromide (8.5 g, 44.55 mmol) was added to a solution of the compound (13) (6.2 g, 14.85 mmol) in N,N-dimethylformamide (50 mL) and stirred at 80° C. for 45 minutes. A saturated sodium bicarbonate aqueous solution was added to the reaction mixture and extracted with ethyl acetate. The organic layer was washed with brine and water successively, dried and concentrated. The resulting residue was purified by a silica gel column chromatography (hexane:ethyl acetate=2:1) and the crystalline obtained after concentration was filtered and dried to give the compound (14) (3.0 g, 34% yield).

$^1$H-NMR (CDCl$_3$) δ ppm: 1.38 (d, 6H, J=6 Hz), 1.80-2.00 (m, 2H), 2.10-2.15 (m, 2H), 2.40-2.50 (m, 2H), 2.70-2.78 (m, 1H), 3.90-4.00 (m, 2H), 4.60-4.70 (m, 1H), 6.96-7.06 (m, 2H), 7.30-7.35 (m, 1H), 7.40-7.60 (m, 3H), 7.65-7.80 (m, 5H).

Step 9

A 1M aqueous solution of sodium hydroxide (15.45 mL, 15.45 mmol) was added to a solution of the compound (14) (3.0 g, 5.15 mmol) in a mixed solvent of tetrahydrofuran (60 mL) and methanol (20 mL) and stirred at room temperature for 15 minutes. After being concentrated, a citric acid aqueous solution and ethyl acetate were added and the mixture was extracted. The organic layer was washed with a saturated sodium bicarbonate aqueous solution, dried and concentrated. The residue was crystallized from ethyl acetate to give the compound (19) (2.5 g, 99.9% yield).

$^1$H-NMR (CDCl$_3$) δ ppm: 1.09 (d, 6H, J=6 Hz), 1.43-1.54 (m, 2H), 1.72-1.77 (m, 2H), 2.09-2.18 (m, 2H), 2.50-2.55 (m, 1H), 3.50 (d, 2H, J=12 Hz), 4.50-4.56 (m, 1H), 6.91-6.94 (m, 3H), 7.03 (s, 1H), 7.45 (d, 2H, J=8.7 Hz), 7.67 (d, 1H, J=7.2 Hz), 11.41 (br, 1H).

Step 10

Methyl bromoacetate (96 mg, 0.84 mmol) and cesium carbonate (136 mg, 0.42 mmol) were added to a solution of the compound (15) (200 mg, 0.42 mmol) in N,N-dimethylformamide (10 mL) and stirred at room temperature for 18 hours. Water (200 mL) was added to the reaction solution and the mixture was extracted with ethyl acetate (20 mL). The organic layer was washed with brine, dried and concentrated. The crystalline obtained after concentration was filtered and dried to give the compound (16) (190 mg, 82% yield).

$^1$H-NMR (CDCl$_3$) δ ppm: 1.39 (d, 6H, J=6 Hz), 1.83-1.92 (m, 2H), 2.36-2.42 (m, 2H), 2.65-2.75 (m, 2H), 3.77 (s, 3H), 3.81 (d, 2H, J=11.7 Hz), 4.60-4.70 (m, 1H), 5.00 (s, 2H), 6.92 (s, 1H), 6.96-7.00 (m, 2H), 7.18 (d, 1H, J=8.1 Hz), 7.67 (d, 1H, J=8.4 Hz), 7.69-7.73 (m, 2H).

Step 11

A 2M aqueous solution of lithium hydroxide (0.4 mL, 0.8 mmol) was added to a solution of the compound (16) (70 mg, 0.127 mmol) in methanol (1.0 mL) and tetrahydrofuran (4.0 mL) and stirred at room temperature for 35 minutes. The reaction solution was diluted with water, acidified by adding diluted hydrochloric acid and extracted with ethyl acetate. The extract was washed with water, dried and concentrated. The residue was crystallized from ethyl acetate to give the compound I-13 (154 mg, 79% yield).

$^1$H-NMR (CDCl$_3$) δ ppm: 1.31 (d, 6H, J=6 Hz), 1.80-1.90 (m, 2H), 1.99-2.31 (m, 2H), 2.35 (t, 2H, J=11.1 Hz), 2.70-2.80 (m, 1H), 3.73 (d, 2H, J=12 Hz), 4.70-4.80 (m, 1H), 4.89 (s, 2H), 7.14 (d, 2H, J=8.7 Hz), 7.21 (d, 1H, J=8.1 Hz), 7.30 (s, 1H), 7.67 (d, 2H, J=9 Hz), 7.94 (d, 1H, J=8.1 Hz).

The compounds (F-1) to (F-) in the Tables 2-5 can be synthesized in the same manner as Example 2 and 3.

TABLE 2

| Compound No. | Structure |
| --- | --- |
| F1 | 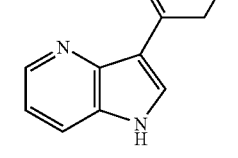 |
| F2 | 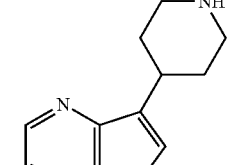 |
| F3 | 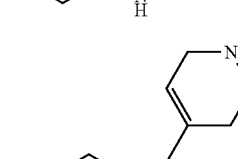 |
| F4 | 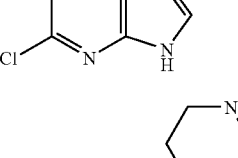 |
| F5 | 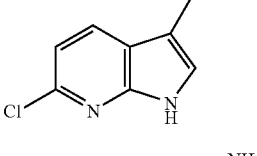 |

TABLE 2-continued
| Compound No. | Structure |
|---|---|
| F6 | 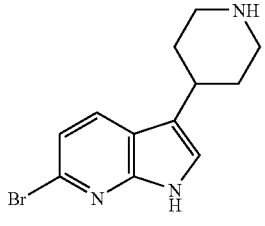 |
| F7 | 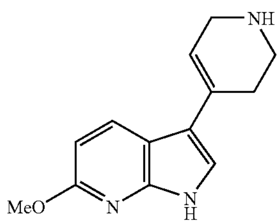 |
| F8 | 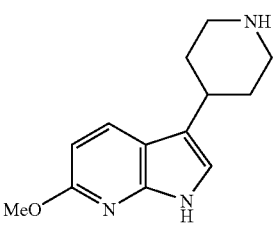 |
| F9 | 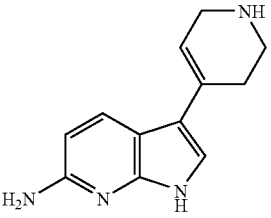 |
| F10 | 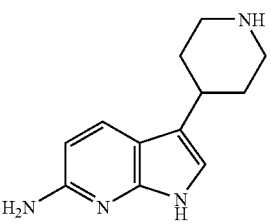 |
TABLE 3
| Compound No. | Structure |
|---|---|
| F11 | 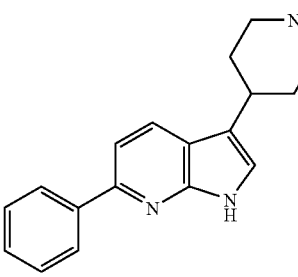 |
TABLE 3-continued
| Compound No. | Structure |
|---|---|
| F12 | 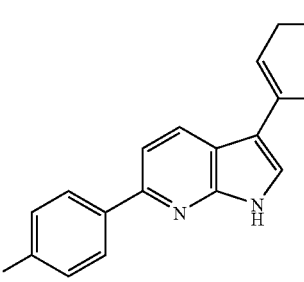 |
| F13 | 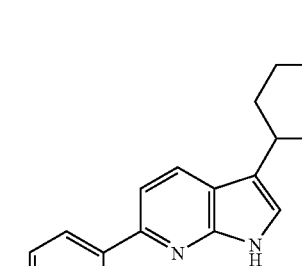 |
| F14 | 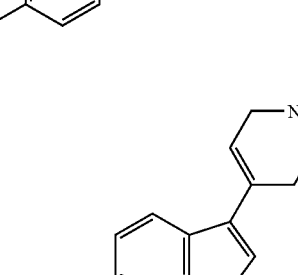 |
| F15 | 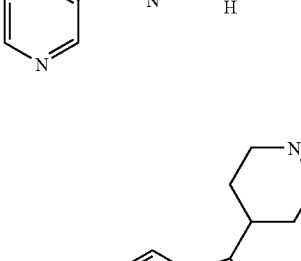 |
| F16 | 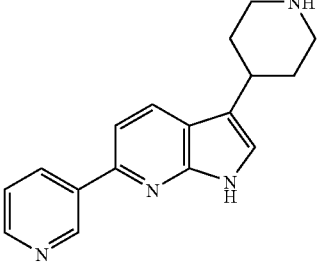 |

TABLE 3-continued
| Compound No. | Structure |
|---|---|
| F17 | 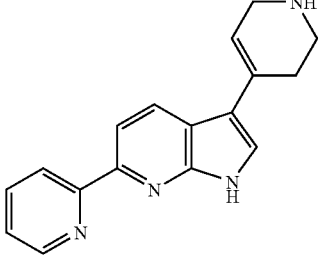 |
| F18 | 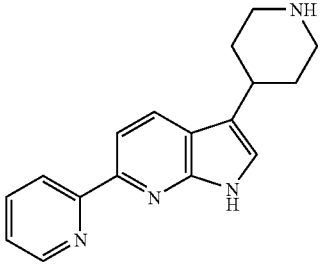 |
| F19 | 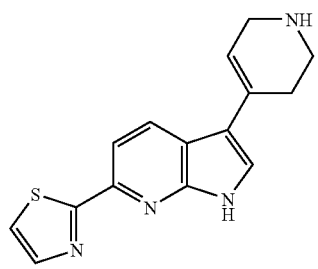 |
| F20 | 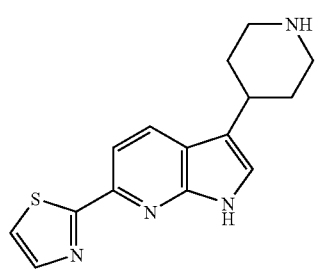 |
| F21 | 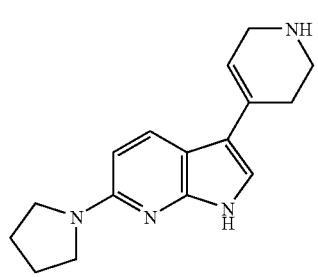 |
TABLE 3-continued
| Compound No. | Structure |
|---|---|
| F22 | 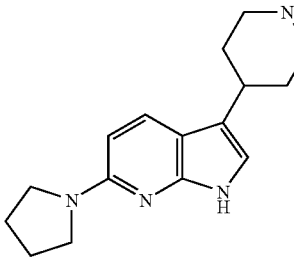 |
TABLE 4
| Compound No. | Structure |
|---|---|
| F23 | 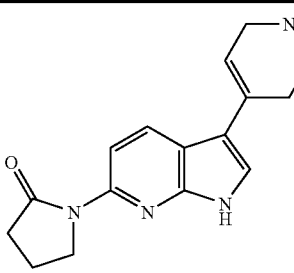 |
| F24 | 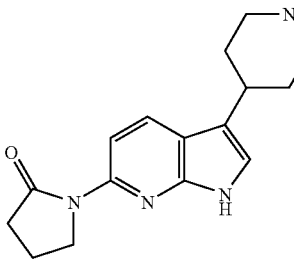 |
| F25 | 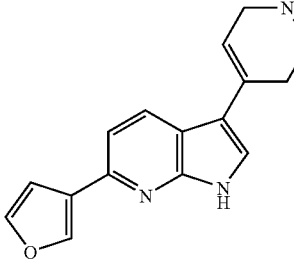 |
| F26 | 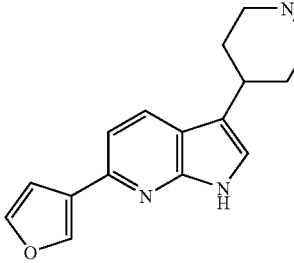 |

TABLE 4-continued
| Compound No. | Structure |
|---|---|
| F27 | 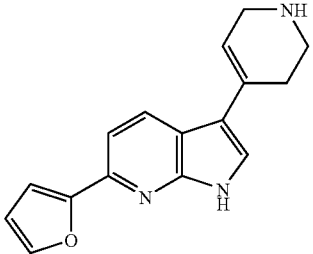 |
| F28 | 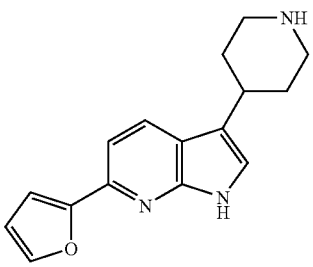 |
| F29 | 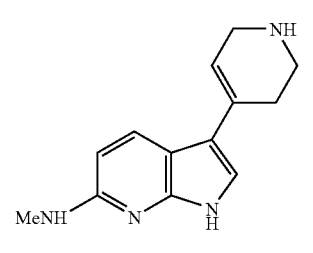 |
| F30 | 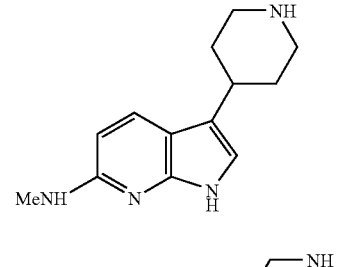 |
| F31 | 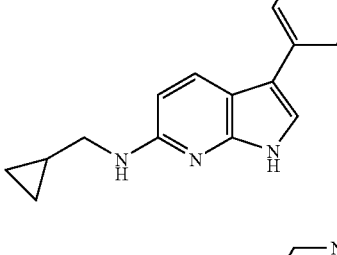 |
| F32 | 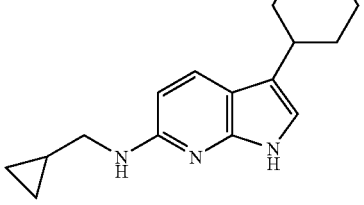 |
TABLE 4-continued
| Compound No. | Structure |
|---|---|
| F33 | 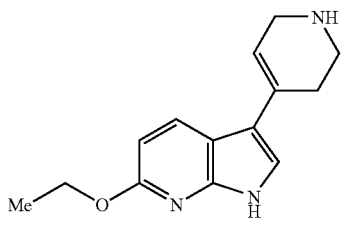 |
| F34 | 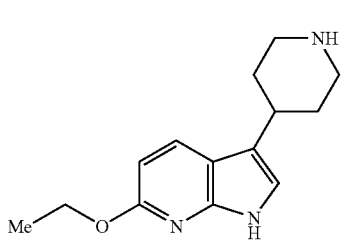 |
TABLE 5
| Compound No. | Structure |
|---|---|
| F35 | 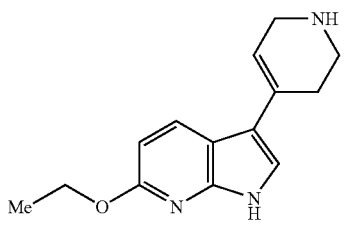 |
| F36 | 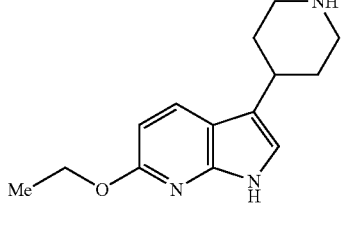 |
| F37 | 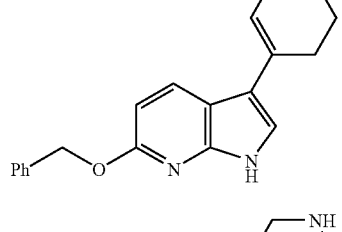 |
| F38 | 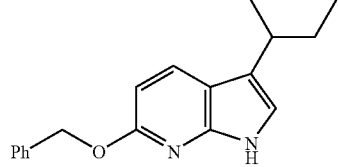 |

TABLE 5-continued

| Compound No. | Structure |
|---|---|
| F39 | 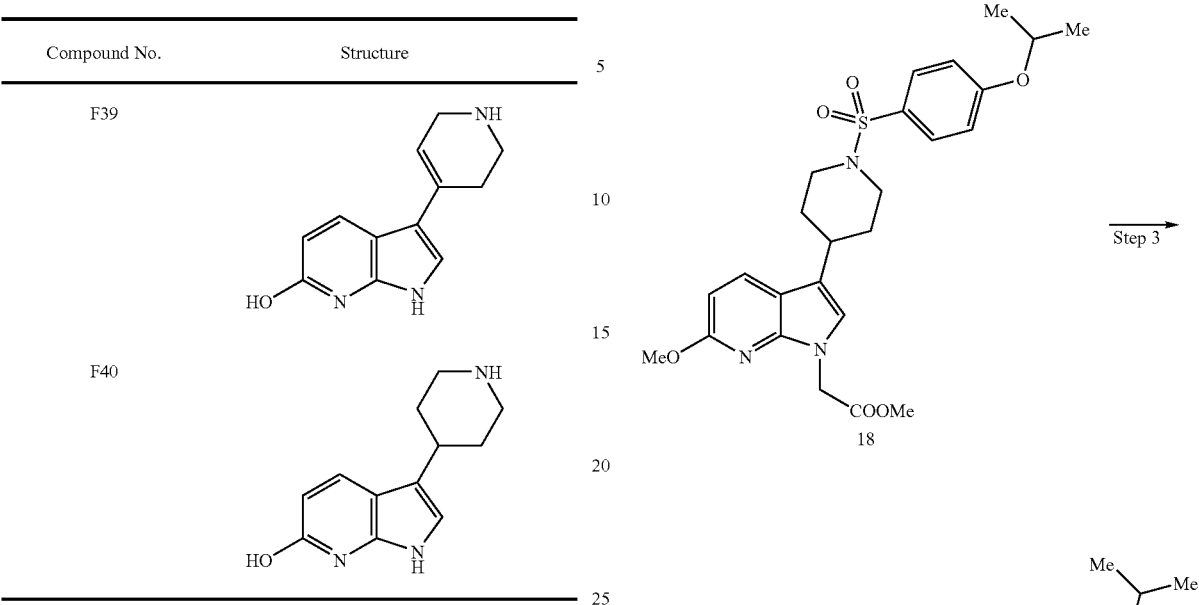 |
| F40 | 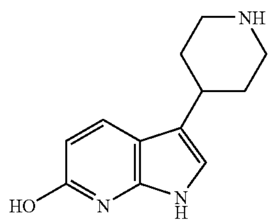 |

Example 4

Preparation of the Compound I-14

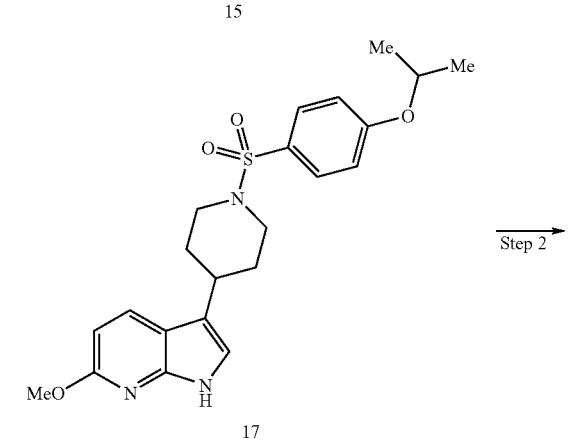

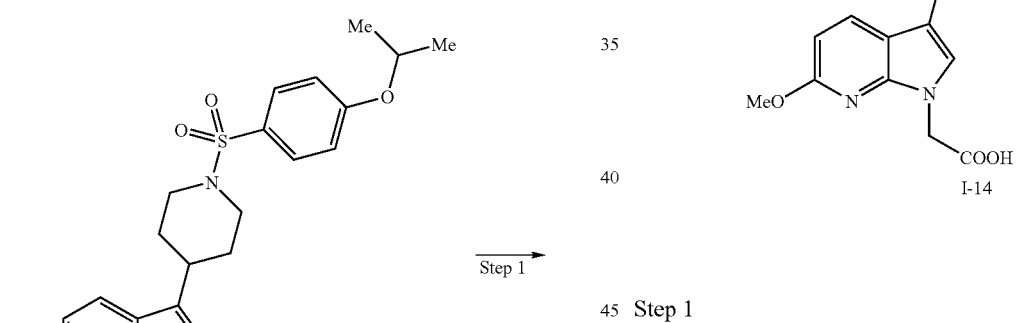

Step 1

To the compound (15) (60 mg, 0.125 mmol) and a 28% methanol solution of sodium methoxide (3 mL) was added cuprous bromide (6 mg, 0.04 mmol) and the mixture was heated with stirring at 140° C. with microwave for 10 minutes. The reaction solution was added to an aqueous solution of citric acid (citric acid 4 g, water 25 mL) and the solution was neutralized with sodium bicarbonate. The product was extracted with ethyl acetate (30 mL) and the organic layer was washed with brine, dried and condensed. The resulting residue was crystallized from chloroform and dried to give the compound (17) (31 mg, 57% yield).

$^1$H-NMR (CDCl$_3$) δ ppm: 1.31 (d, 6H, J=6 Hz), 1.65-1.70 (m, 2H), 1.94-1.99 (m, 2H), 2.30-2.40 (m, 2H), 2.65-2.75 (m, 1H), 3.70 (d, 2H, J=11.7 Hz), 4.73-4.79 (m, 1H), 6.43 (d, 1H, J=8.7 Hz), 6.92 (s, 1H), 7.12-7.18 (m, 2H), 7.65-7.70 (m, 2H), 7.79 (d, 1H, J=8.4 Hz), 11.17 (s, 1H).

Step 2

To a solution of the compound (17) (150 mg, 0.35 mmol) in N,N-dimethylformamide (3 mL) were added methyl bromoacetate (97 mg, 0.63 mmol) and cesium carbonate (228 mg, 0.70 mmol) and the mixture was stirred at room temperature for an hour. Water (200 mL) was added to the reaction solution, extracted with ethyl acetate (20 mL) and the organic layer was washed with brine, dried and condensed. The resulting residue was purified by silica gel column chromatography (chloroform:EtOH 9:1) and the crystalline obtained after condensation was filtered and dried to give the compound (8) (115 mg, 65% yield).

$^{1}$H-NMR (CDCl$_{3}$) δ ppm: 1.38 (d, 6H, J=6 Hz), 1.80-1.95 (m, 2H), 2.03-2.07 (br, 2H), 2.36-2.46 (m, 2H), 2.60-2.70 (m, 1H), 3.76 (s, 3H), 3.93 (s, 3H), 4.62-4.67 (m, 1H), 4.94 (s, 1H), 6.51 (d, 1H, J=8.7 Hz), 6.73 (s, 1H), 6.96-6.99 (m, 2H), 7.67-7.74 (m, 3H).

Step 3

A 2M aqueous solution of lithium hydroxide (0.48 mL, 0.96 mmol) was added to a solution of the compound (18) (161 mg, 0.32 mmol) in methanol (3.0 mL) and tetrahydrofuran (5.0 mL) and the mixture was stirred at room temperature for 20 minutes. The reaction solution was diluted with water and acidified by adding diluted Hydrochloric acid and then the product was extracted with ethyl acetate, and the extract was washed with water, dried and condensed. The residue was crystallized from ethyl acetate to give the compound I-14 (136 mg, 87% yield).

$^{1}$H-NMR (CDCl$_{3}$) δ ppm: 1.31 (d, 6H, J=6 Hz), 1.55-1.70 (m, 2H), 1.97-2.01 (m, 2H), 2.36 (t, 2H, J=11.4 Hz), 2.65-2.75 (m, 1H), 3.72 (d, 2H, J=11.4 Hz), 3.83 (s, 3H), 4.73-4.80 (m, 1H), 4.85 (s, 2H), 6.47 (d, 1H, J=8.4 Hz), 7.14 (s, 1H), 7.15 (d, 2H, J=8.7 Hz), 7.68 (d, 2H, J=8.7 Hz), 7.84 (d, 1H, J=9.6 Hz).

Example 5

Preparation of the Compound I-26

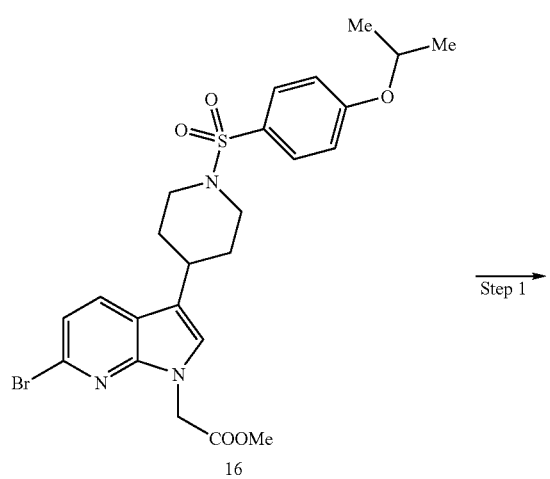

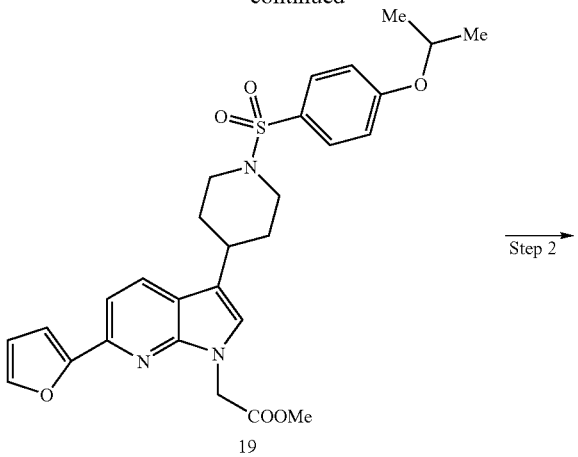

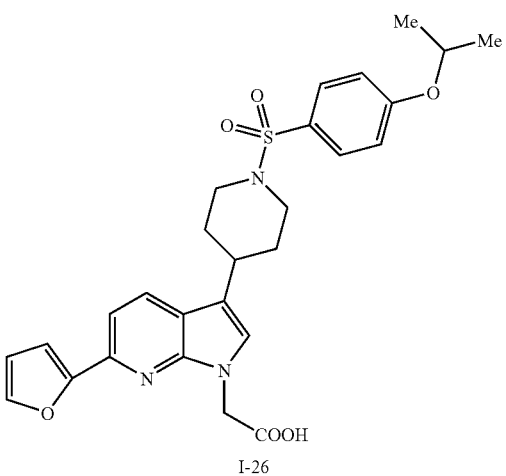

Step 1

A 2M aqueous solution of potassium carbonate (0.2 mL) was added to a solution of the compound (16) (55 mg, 0.100 mmol), 2-furanboronic acid (2.2 mg, 0.01 mmol), palladium acetate (2.2 mg, 0.01 mmol) and triphenylphosphine (5.2 mg, 0.02 mmol) in N,N-dimethylformamide (1.0 mL) and the mixture was stirred under nitrogen atmosphere for 2.5 hours. Water was added to the reaction solution and extracted with ethyl acetate. The organic layer was washed with brine and water successively, dried and condensed. The resulting residue was purified by silica gel column chromatography (hexane:ethyl acetate=1:2) and the crystalline obtained after condensation was filtered and dried to give the compound (19) (32 mg, 77% yield).

$^{1}$H-NMR (CDCl$_{3}$) δ ppm: 1.39 (1H, d, J=5.9 Hz), 1.82-1.99 (2H, m), 2.02-2.15 (2H, m), 2.35-2.50 (2H, m), 2.64-2.80 (1H, m), 3.77 (3H, s), 3.87-3.97 (2H, m), 4.66 (1H, m), 5.12 (2H, s), 6.52 (1H, dd, J=3.3, 1.9 Hz), 6.93-7.03 (3H, m), 7.11 (1H, d, J=3.1 Hz), 7.47-7.53 (2H, m), 7.72 (2H, d, J=8.8 Hz), 7.82 (1H, d, J=8.1 Hz).

Step 2

A 2M aqueous solution of lithium hydroxide (0.06 mL, 0.120 mmol) was added to a suspension of the compound (19) (32 mg, 0.060 mmol) in a mixture of methanol (1.0 mL) and tetrahydrofuran (1.0 mL) and stirred at room temperature for 4 hours, and then a 2M aqueous solution of lithium hydroxide (0.06 mL, 0.120 mmol) was further added and stirred at room temperature for 2.5 hours. The reaction solution was diluted with water and acidified by adding a 0.5M aqueous solution of citric acid. The product was extracted with ethyl acetate, and the extract was washed with water, dried and concentrated. The residue was crystallized from ethyl acetate to give the compound I-26 (23 mg, 74% yield).

$^1$H-NMR (CDCl$_3$) δ ppm: 1.39 (1H, d, J=6.1 Hz), 1.79-1.95 (2H, m), 1.96-2.10 (2H, m), 2.35-2.49 (2H, m), 2.62-2.76 (1H, m), 3.87-3.96 (2H, m), 4.65 (1H, m), 5.08 (2H, s), 6.55 (1H, dd, J=3.5, 1.8 Hz), 6.90 (1H, s), 6.98 (2H, d, J=8.9 Hz), 7.14 (1H, d, J=3.8 Hz), 7.50-7.56 (2H, m), 7.71 (2H, d, J=8.9 Hz), 7.89 (1H, d, J=8.2 Hz).

The compounds of (I-1) to (I-3), (I-5) to (I-12), (I-15) to (I-25), (I-27) to (I-32) were synthesized in the same manner as set forth above. The chemical structures and physical properties thereof are shown in Tables 6-16.

In addition, the compound of (II-1) to (II-59), (II-61) to (II-74), (II-76) to (II-80), (II-82) to (II-93), (II-95), (II-97) to (II-105), (II-110) to (II-149) can be synthesized in the same manner as set forth above. Their structures are shown in Tables 17-29.

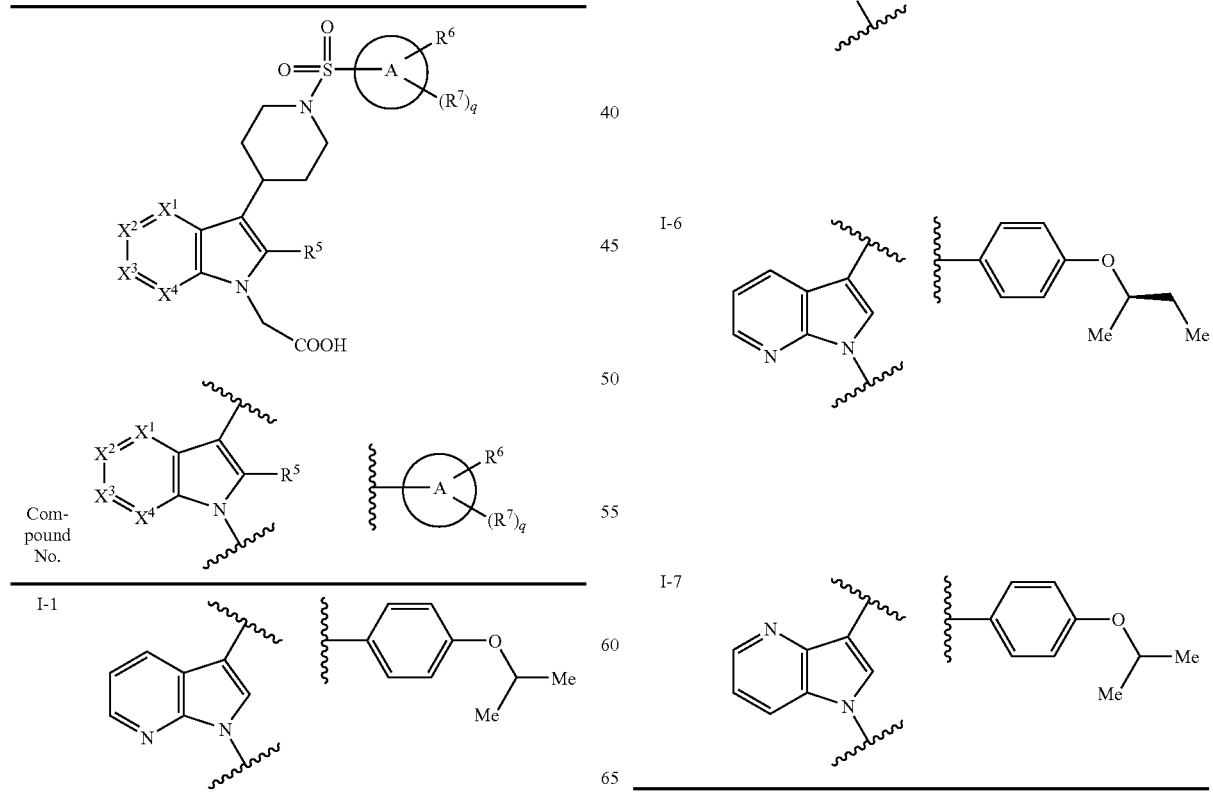

TABLE 7
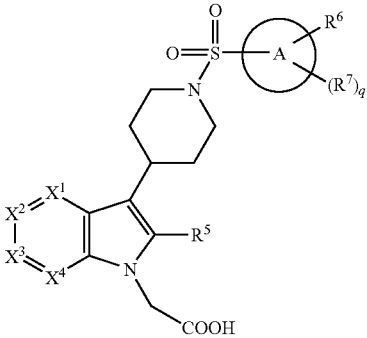
| Compound No. | 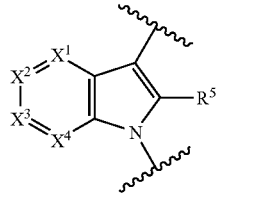 | 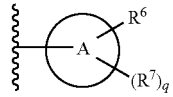 |
|---|---|---|
| I-8 | 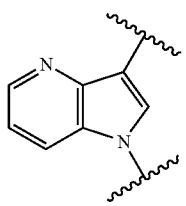 | 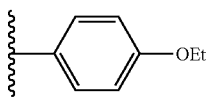 |
| I-11 | 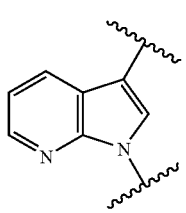 | 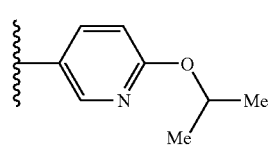 |
| I-12 | 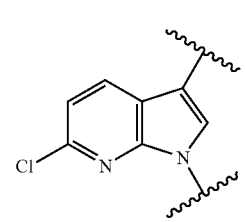 | 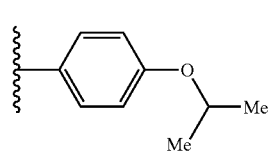 |
| I-13 | 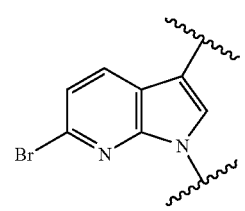 | 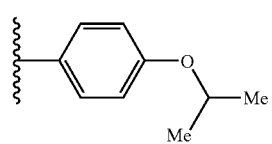 |
| I-14 | 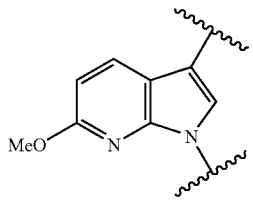 | 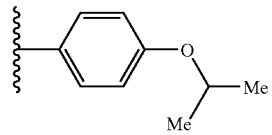 |

TABLE 7-continued
I-15  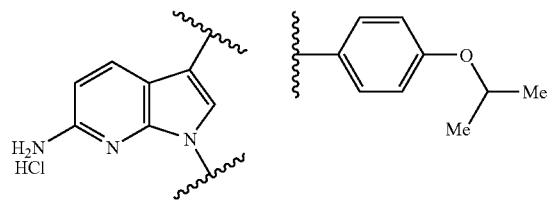
TABLE 8
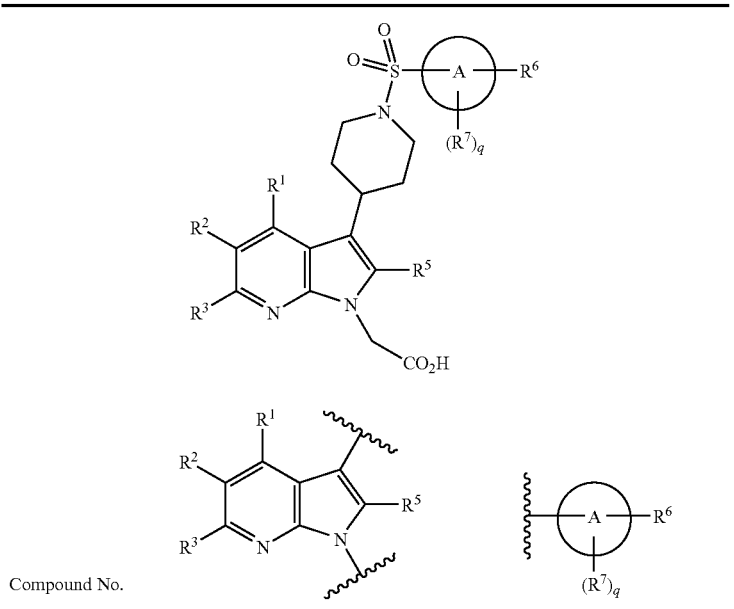
Compound No.
I-16  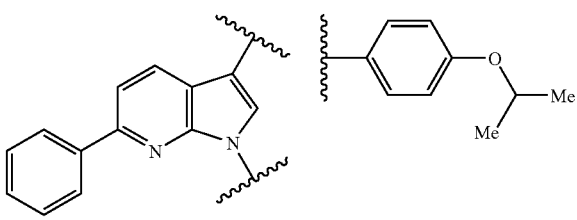
I-17  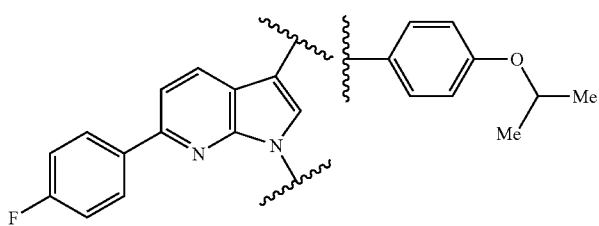
I-18  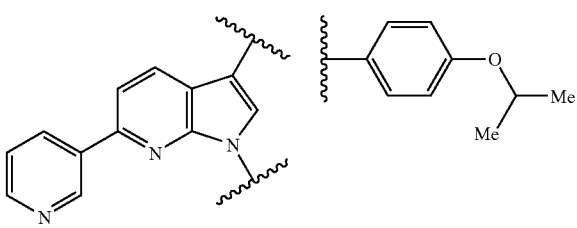

TABLE 8-continued
| | | |
|---|---|---|
| I-19 | 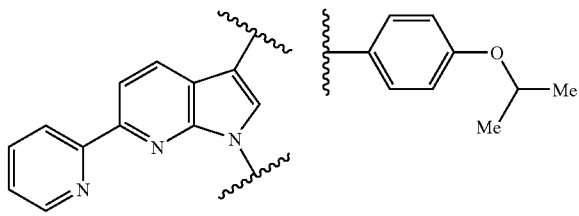 | |
| I-20 | 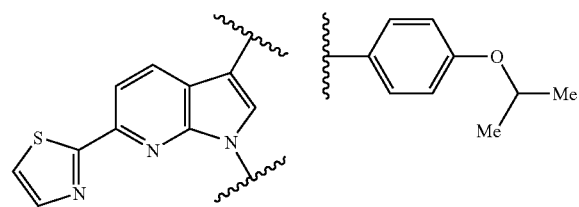 | |
| I-21 | 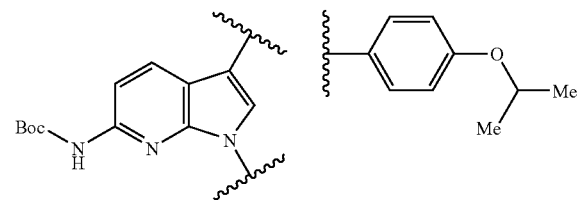 | |
TABLE 9
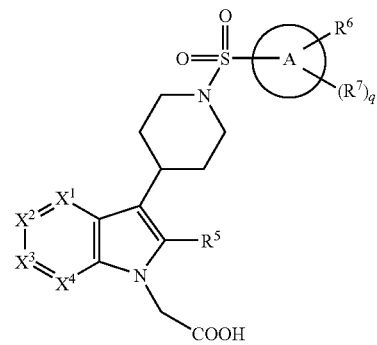
| Compound No. | 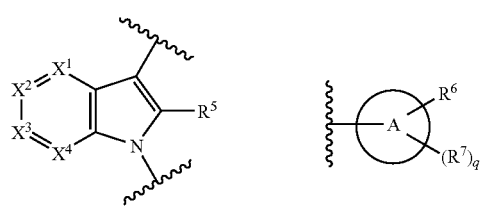 | |
|---|---|---|
| I-22 | 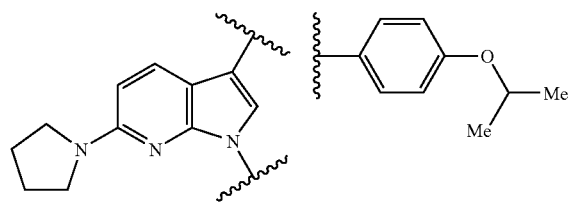 | |

TABLE 9-continued
| I-23 | 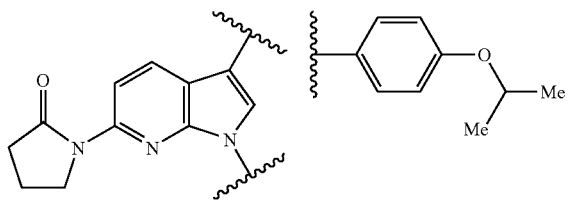 |
| I-24 | 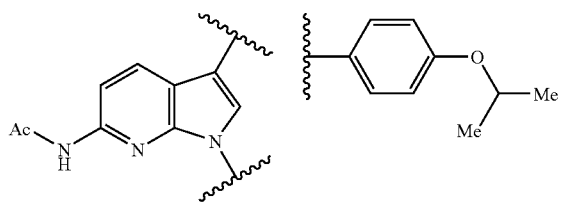 |
| I-25 | 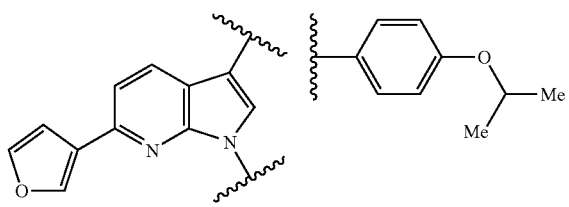 |
| I-26 | 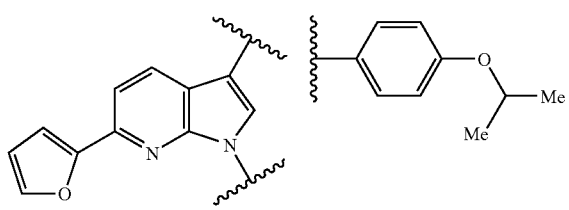 |
| I-27 | 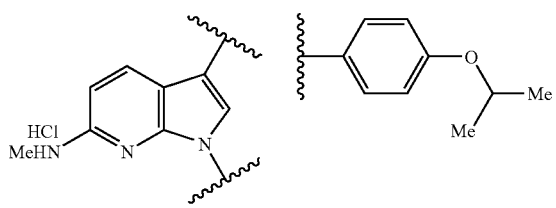 |
TABLE 10
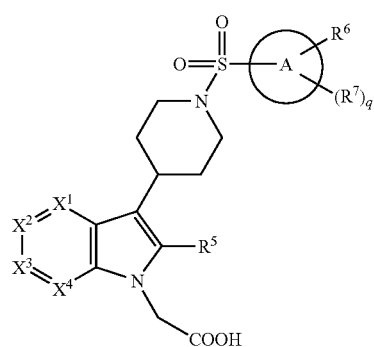

TABLE 10-continued

| Compound No. | [pyrrolopyridine core with X1, X2, X3, X4, R5] | [ring A with R6, (R7)q] |
|---|---|---|
| I-28 | 6-(cyclopropylmethylamino)-7-azaindole, HCl | 4-(isopropoxy)phenyl |
| I-29 | 6-ethoxy-7-azaindole | 4-(isopropoxy)phenyl |
| I-30 | 6-(2-methoxyethoxy)-7-azaindole | 4-(isopropoxy)phenyl |
| I-31 | 6-(benzyloxy)-7-azaindole | 4-(isopropoxy)phenyl |
| I-32 | 6-hydroxy-7-azaindole | 4-(isopropoxy)phenyl |

TABLE 11
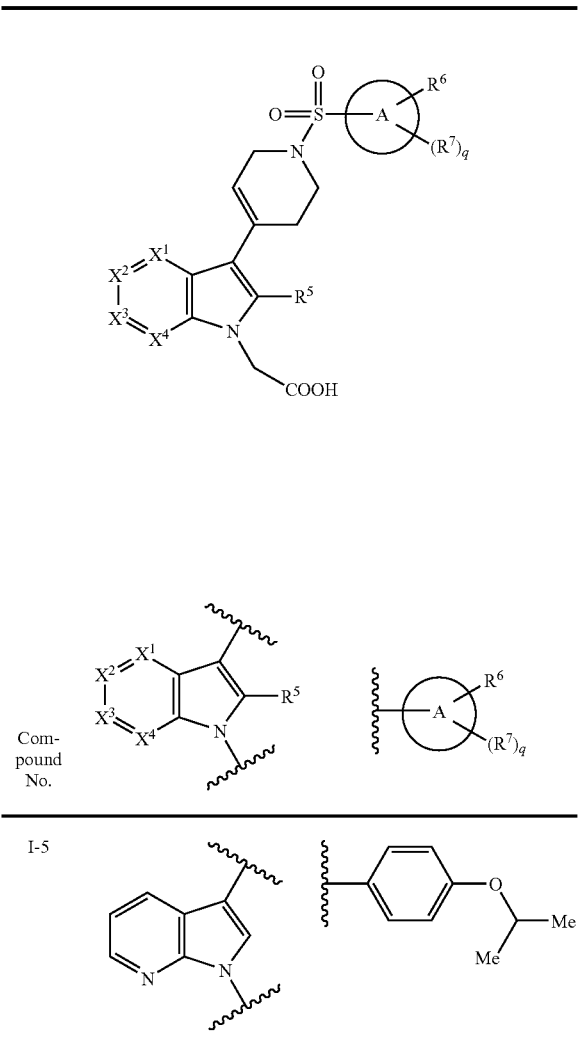
| Compound No. | | |
|---|---|---|
| I-5 | | |
| I-9 | | |
TABLE 12
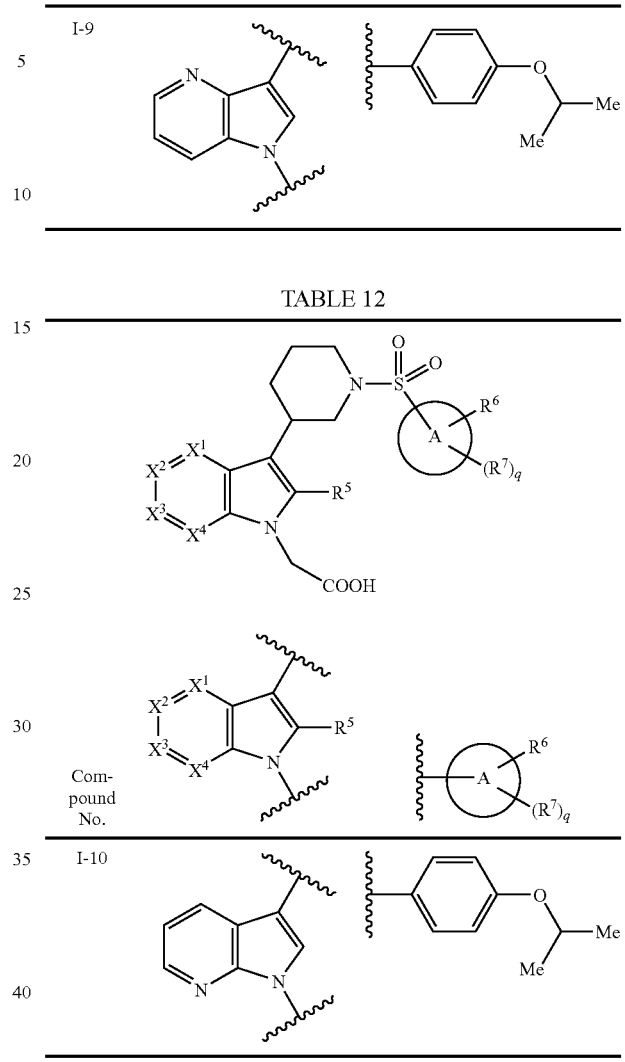
| Compound No. | | |
|---|---|---|
| I-10 | | |
TABLE 13
| Compound No. | 1H-NMR (DMSO-d6) δ ppm |
|---|---|
| I-1 | 1.32 (d, 6H, J = 6.0 Hz), 1.59-1.73 (m, 2H), 2.01 (brd, 2H), 2.37 (brt, 2H), 2.78 (m, 1H), 3.74 (brd, 2H), 4.76 (m, 1H), 4.94 (s, 2H), 7.04 (dd, 1H, J = 4.5, 7.8 Hz), 7.13-7.18 (m, 2H), 7.29 (s, 1H), 7.66-7.71 (m, 2H), 7.95 (dd, 1H, J = 1.8, 7.8 Hz), 8.18 (dd, 1H, J = 1.8, 4.5 Hz), 12.91 (brs, 1H) |
| I-2 | 1.59-1.78 (m, 2H), 2.02 (brd, 2H), 2.36 (brt, 2H), 2.77 (m, 1H), 3.75 (brd, 2H), 3.88 (s, 3H), 4.95 (s, 2H), 7.04 (dd, 1H, J = 4.5, 7.8 Hz), 7.17-7.22 (m, 2H), 7.29 (s, 1H), 7.70-7.75 (m, 2H), 7.95 (dd, 1H, J = 1.5, 7.8 Hz), 8.18 (dd, 1H, J = 1.5, 4.5 Hz), 12.94 (br, 1H) |
| I-3 | 1.73 (t, 3H, J = 6.9 Hz), 1.59-1.73 (m, 2H), 2.02 (brd, 2H), 2.36 (brt, 2H), 2.77 (m, 1H), 3.74 (brd, 2H), 4.15 (q, 2H, J = 6.9 Hz), 4.94 (s, 2H), 7.04 (dd, 1H, J = 4.5, 7.8 Hz), 7.14-7.19 (m, 2H), 7.29 (s, 1H), 7.68-7.73 (m, 2H), 7.95 (dd, 1H, J = 1.2, 7.8 Hz), 8.18 (dd, 1H, J = 1.2, 4.5 Hz), 12.94 (br, 1H) |
| I-4 | 1.32 (d, 6H, J = 6.0 Hz), 1.58-1.74 (m, 2H), 2.00 (brd, 2H), 2.37 (brt, 2H), 2.78 (m, 1H), 3.76 (brd, 2H), 4.76 (m, 1H), 5.06 (s, 2H), 7.15 (d, 2H, J = 8.7 Hz), 7.35 (s, 1H), 7.51 (d, 1H, J = 5.7 Hz), 7.68 (d, 2H, J = 8.7 Hz), 8.07 (d, 1H, J = 5.7 Hz), 8.72 (s, 1H) |

TABLE 13-continued

| Compound No. | 1H-NMR (DMSO-d6) δ ppm |
|---|---|
| I-5 | 1.27 (d, 6H, J = 6.0 Hz), 2.56 (brs, 2H), 3.22 (t-like, 2H), 3.69 (brs, 2H), 4.72 (m, 1H), 4.99 (s, 2H), 6.15 (brs, 1H), 7.09-7.16 (m, 3H), 7.59 (s, 1H), 7.70-7.75 (m, 2H), 8.20-8.25 (m, 2H), 13.00 (br, 1H) |
| I-6 | 0.94 (t, 3H, J = 7.7 Hz), 1.28 (d, 3H, J = 6.0 Hz), 1.55-1.78 (m, 4H), 2.02 (brd, 2H), 2.38 (brt, 2H), 2.78 (m, 1H), 3.74 (brd, 2H), 4.54 (m, 1H), 4.94 (s, 2H), 7.04 (dd, 1H, J = 4.8, 7.8 Hz), 7.14-7.18 (m, 2H), 7.28 (s, 1H), 7.66-7.71 (m, 2H), 7.96 (dd, 1H, J = 1.5, 7.8 Hz), 8.19 (dd, 1H, J = 1.5, 4.8 Hz), 12.91 (brs, 1H) |
| I-7 | 1.33 (d, 6H, J = 6.0 Hz), 1.79 (q, 2H, J = 12.3 Hz), 2.11 (d, 2H, J = 11.4 Hz), 2.36 (t, 2H, J = 11.4 Hz), 2.85 (t, 1H, J = 11.4 Hz), 3.73 (d, 2H, J = 11.7 Hz), 4.76 (m, 1H), 4.99 (s, 2H), 7.09-7.16 (m, 3H), 7.39 (s, 1H), 7.68 (d, 2H, J = 9.0 Hz), 7.79 (d, 1H, J = 8.4 Hz), 8.29 (d, 1H, J = 4.5 Hz) |
| I-8 | 1.37 (t, 3H, J = 6.9 Hz), 1.78 (q, 2H, J = 12.3 Hz), 2.10 (d, 2H, J = 10.8 Hz), 2.35 (t, 2H, J = 11.4 Hz), 2.84 (t, 1H, J = 11.4 Hz), 3.73 (d, 2H, J = 11.1 Hz), 4.14 (q, 2H, J = 6.9 Hz), 5.00 (s, 2H), 7.14-7.17 (m, 3H), 7.42 (brs, 1H), 7.69 (d, 2H, J = 8.4 Hz), 7.84 (d, 1H, J = 8.1 Hz), 8.31 (d, 1H, J = 3.9 Hz) |
| I-9 | 1.28 (d, 6H, J = 6.3 Hz), 2.58 (brs, 2H), 3.22 (t, 2H, J = 5.7 Hz), 3.71 (brs, 2H), 4.69-4.77 (m, 1H), 5.02 (s, 2H), 7.11-7.18 (m, 4H), 7.63 (s, 1H), 7.72 (d, 2H, J = 8.7 Hz), 7.84 (dd, 1H, J = 1.2, 8.4 Hz), 8.37 (dd, 1H, J = 1.5, 4.5 Hz) |
| I-10 | 1.29 (d, 6H, J = 6.0 Hz), 1.44-2.00 (m, 4H), 2.27-2.39 (m, 2H), 3.10 (m, 1H), 3.63 (brd, 1H), 3.76 (brd, 1H), 4.72 (m, 1H), 4.96 (s, 2H), 7.07-7.12 (m, 3H), 7.35 (s, 1H), 7.62-7.67 (m, 2H), 8.01 (dd, 1H, J = 1.5, 7.8 Hz), 8.22 (dd, 1H, J = 1.5, 4.8 Hz), 12.94 (br, 1H) |

TABLE 14

| Compound No. | 1H-NMR (DMSO-d6) δ ppm |
|---|---|
| I-11 | 1.35 (d, 6H, J = 6.0 Hz), 1.61-1.75 (m, 2H), 2.04 (brd, 2H), 2.43-2.50 (m, 2H), 2.83 (m, 1H), 3.77 (brd, 2H), 4.95 (s, 2H), 5.36 (m, 1H), 6.99 (dd, 1H, J = 0.6, 9.0 Hz), 7.05 (dd, 1H, J = 4.5, 7.8 Hz), 7.30 (s, 1H), 7.96 (dd, 1H, J = 1.5, 7.8 Hz), 8.02 (dd, 1H, J = 2.7, 9.0 Hz), 8.19 (dd, 1H, J = 1.5, 4.5 Hz), 8.56 (dd, 1H, J = 0.6, 2.7 Hz), 12.90 (br, 1H) |
| I-12 | 1.31 (6H, d, J = 6 Hz), 1.60-1.70 (2H, m), 2.07 (2H, d, J = 11.4 Hz), 2.31 (2H, t, J = 11.7 Hz), 3.0-3.5 (1H, m), 3.76 (2H, d, J = 10.8 Hz), 4.71 (2H, s), 4.71-4.77 (1H, m), 7.09 (1H, d, J = 5.1 Hz), 7.14 (2H, d, J = 8.7 Hz), 7.40 (1H, s), 7.67 (2H, d, J = 8.7 Hz), 8.08 (1H, d, J = 5.1 Hz) |
| I-13 | 1.31 (6H, d, J = 6 Hz), 1.80-1.90 (2H, m), 1.99-2.31 (2H, m), 2.35 (2H, t, J = 11.1 Hz), 2.70-2.80 (1H, m), 3.73 (2H, d, J = 12 Hz), 4.70-4.80 (1H, m), 4.89 (2H, s), 7.14 (2H, d, J = 8.7 Hz), 7.21 (1H, d, J = 8.1 Hz), 7.30 (1H, s), 7.67(2H, d, J = 9 Hz), 7.94 (1H, d, J = 8.1 Hz) |
| I-14 | 1.31 (6H, d, J = 6 Hz), 1.55-1.70 (2H, m), 1.95-2.05 (2H, m), 2.36 (2H, t, J = 11.4 Hz), 2.65-2.75 (2H, m), 3.73 (2H, d, J = 11.4 Hz), 3.83 (3H, s), 4.70-4.80 (1H, m), 4.85 (2H, s), 6.48 (1H, d, J = 8.4 Hz), 7.01 (1H, s), 7.14 (2H, d, J = 8.7 Hz) 7.68 (2H, d, J = 8.7 Hz), 7.84 (1H, d, J = 8.4 Hz) |
| I-15 | 1.31 (2H, d, J = 6 Hz), 1.55-1.65 (2H, m), 1.96 (2H, d, J = 14.4 Hz), 2.32 (2H, t, J = 11.4 Hz), 2.69 (1H, brs), 4.75 (1H, m), 4.98 (2H, s), 6.57 (1H, d, J = 9 Hz), 6.96 (1H, d, J = 9 Hz), 7.13 (2H, d, J = 8.7 Hz), 7.68 (2H, d, J = 8.7 Hz), 8.10-8.15 (1H, m) |
| I-16 | 1.32 (6H, d, J = 6.0 Hz), 1.69 (2H, m), 2.03 (2H, m), 2.39 (2H, m), 2.80 (1H, m), 3.75 (2H, m), 4.77(1H, tt, J = 6.0 Hz, 6.0 Hz), 5.02 (2H, s), 7.16 (2H, d, J = 8.7 Hz), 7.32 (1H, s), 7.44-7.49 (2H, m), 7.64 (1H, d, J = 8.1 Hz), 7.69 (2H, d, J = 8.7 Hz), 8.03 (1H, d, J = 8.1 Hz), 8.08-8.11 (2H, m). |
| I-17 | 1.30 (6H, d, J = 6.0 Hz), 1.68 (2H, m), 2.38 (2H, m), 2.80 (1H, m), 3.75 (2H, m), 4.77 (1H, tt, J = 6.0 Hz, 6.0 Hz), 5.02 (2H, s), 7.16 (2H, d, J = 9.0 Hz), 7.26-7.32 (2H, m), 7.64 (2H, d, J = 8.1 Hz), 7.69 (2H, d, J = 9.0 Hz), 8.04 (1H, d, J = 8.1 Hz), 8.14 (2H, m). |
| I-18 | 1.32 (6H, d, J = 6.0 Hz), 1.69 (2H, m), 2.39 (2H, m), 2.83 (1H, m), 3.76 (2H, m), 4.77 (1H, tt, J = 6.0 Hz, 6.0 Hz), 5.07 (2H, s), 7.16 (2H, d, J = 9.0 Hz), 7.41 (1H, s), 7.67-7.75 (3H, m), 7.80 (1H, d, J = 8.1 Hz), 8.14 (1H, d, J = 8.1 Hz), 8.69 (1H, m), 8.72 (1H, m), 9.38 (1H, m). |

TABLE 14-continued

| Compound No. | 1H-NMR (DMSO-d6) δ ppm |
|---|---|
| I-19 | 1.33 (6H, d, J = 6.0 Hz), 1.72 (2H, m), 2.05 (2H, m), 2.39 (2H, m), 2.83 (1H, m), 3.77 (2H, m), 4.77 (1H, tt, J = 6.0 Hz, 6.0 Hz), 5.10 (2H, s), 7.17 (2H, d, J = 9.0 Hz), 7.44 (1H, s), 7.70 (2H, d, J = 9.0 Hz), 8.05 (1H, m), 8.11 (1H, d, J = 8.1 Hz), 8.17 (1H, d, J = 8.1 Hz), 8.50 (1H, m), 8.69 (1H, m), 13.10 (1H, br). |

TABLE 15

| Compound No. | 1H-NMR (DMSO-d6) δ ppm |
|---|---|
| I-20 | 1.33 (6H, d, J = 6.0 Hz), 1.70 (2H, m), 2.04 (2H, m), 2.39 (2H, m), 2.82 (1H, m), 3.76 (2H, m), 4.77 (1H, tt, J = 6.0 Hz, 6.0 Hz), 5.00 (2H, s), 7.16 (2H, d, J = 9.0 Hz), 7.43 (1H, s), 7.70 (2H, d, J = 9.0 Hz), 7.77 (1H, d, J = 3.3 Hz), 7.88 (1H, d, J = 8.1 Hz), 7.92 (1H ,d, J = 3.3 Hz), 8.10 (1H, d, J = 8.1 Hz), 13.00 (1H, br). |
| I-21 | 1.39 (d, J = 6.3 Hz, 6H), 1.50 (s, 3H), 1.80-1.85 (m, 2H), 2.00-2.10 (m, 2H), 2.38-2.42 (m, 2H), 2.60-2.65 (m, 1H), 3.90 (d, J = 11.7 Hz, 2H), 4.60-4.65 (m, 1H), 4.90 (s, 2H), 6.77 (s, 1H), 6.98 (d, J = 8.7 Hz, 2H), 7.69-7.82 (m, 4H). |
| I-22 | 1.39 (d, J = 6.1 Hz, 6H), 1.76-2.12 (m, 7H), 2.34-2.45 (m, 2H), 2.52-2.67 (m, 1H), 3.40-3.60 (m, 4H), 3.89 (brd, J = 11.7 Hz, 2H), 4.65 (tt, J = 6.1, 6.1 Hz, 1H), 4.90 (brs, 2H), 6.27 (d, J = 8.8 Hz, 1H), 6.50 (s, 1H), 6.98 (d, J = 8.8 Hz, 2H), 7.65-7.31 (m, 1H), 7.71 (d, J = 7.7 Hz, 2H) |
| I-23 | 1.39 (d, J = 5.9 Hz, 6H), 1.76-1.93 (m, 2H), 2.00-2.20 (m, 4H), 2.34-2.45 (m, 2H), 2.62-2.76 (m, 3H), 3.90 (d, J = 11.3 Hz, 2H), 4.13 (t, J = 7.2 Hz, 2H), 4.65 (tt, J = 5.9, 5.9 Hz, 1H), 4.94(s, 2H), 6.85 (s, 1H), 6.98 (d, J = 9.1 Hz, 2H), 7.71 (d, J = 9.1 Hz, 2H), 7.82 (d, J = 8.8 Hz, 1H), 8.15 (d, J = 8.8 Hz, 1H) |
| I-24 | 1.31 (d, J = 6.0 Hz, 6H), 1.53-1.74 (2H, m), 1.92-2.07 (m, 2H), 2.07 (s, 3H), 2.28-2.43 (m, 2H), 2.65-2.81 (m, 1H), 3.68-3.78 (m, 2H), 4.76 (tt, J = 6.0, 6.0 Hz, 1H), 4.87 (brs, 2H), 7.11-7.18 (m, 3H), 7.68 (d, J = 8.9 Hz, 2H), 7.82 (br-d, J = 8.5 Hz, 1H), 7.71 (dd, J = 8.5, 3.3 Hz, 2H) |
| I-25 | 1.39 (6H, d, J = 5.6 Hz), 1.55-1.75 (2H, m), 1.95-2.09 (2H, m), 2.27-2.45 (2H, m), 2.65-2.85 (1H, m), 3.65-3.80 (2H, m), 4.67-4.85 (1H, m), 4.97 (2H, s), 7.04 (1H, s), 7.16 (2H, J = 7.2 Hz), 7.25 (1H, s), 7.40 (1H, d, J = 8.0 Hz), 7.63-7.77 (3H, m), 7.96 (1H, d, J = 7.2 Hz), 8.28 (1H, s), 12.90 (1H, brs). |
| I-26 | 1.39 (1H, d, J = 6.1 Hz), 1.79-1.95 (2H, m), 1.96-2.10 (2H, m), 2.35-2.49 (2H, m), 2.62-2.76 (1H, m), 3.87-3.96 (2H, m), 4.65 (1H, tt, J = 6.1, 6.1 Hz), 5.08 (2H, s), 6.55 (1H, dd, J = 3.5, 1.8 Hz), 6.90 (1H, s), 6.98 (2H, d, J = 8.9 Hz), 7.14 (1H, d, J = 3.8 Hz), 7.50-7.56 (2H, m), 7.71 (2H, d, J = 8.9 Hz), 7.89 (1H, d, J = 8.2 Hz). |

TABLE 16

| Compound No. | 1H-NMR (DMSO-d6) δ ppm |
|---|---|
| I-27 | 1.31 (6H, d, J = 6.3 Hz), 1.50-1.70 (2H, m), 1.96 (2H, d, J = 12 HZ), 2.33 (2H, t, J = 11.7 Hz), 2.63-2.73 (1H, m), 3.67 (3H, s), 3.65-3.73 (2H, m), 4.71-4.80 (1H, m), 5.02 (2H, s), 6.41 (1H, d, J = 8.1 Hz), 6.85 (1H, s), 7.15 (2H, d, J = 9 Hz), 7.67 (2H, d, J = 9 Hz), 7.86 (1H, br). |
| I-28 | 0.26-0.28 (2H, m), 0.47-0.50 (2H, m), 1.06-1.10 (1H, m), 1.72 (6H, d, J = 6 Hz), 1.55-1.65 (2H m), 1.96-1.99(2H, m), 2.34 (2H, t, J = 12 Hz), 2.63-2.73 (1H, m), 3.20 (2H, d, J = 7.2 Hz), 3.73 (2H, d, J = 11.7 Hz), 4.73-4.78 (1H, m), 4.92 (2H, s), 6.54(1H, d, J = 8.4 Hz), 6.90 (1H, s), 7.14 (2H, d, J = 9 Hz), 7.70 (2H, d, J = 9 Hz), 7.90-7.95 (1H, m). |
| I-29 | 1.39 (d, J = 6.1 Hz, 6H), 1.40 (t, J = 7.0 Hz, 3H), 1.77-1.94 (m, 2H), 2.34-2.46 (m, 2H), 3.82-3.95 (m, 1H), 4.34 (q, J = 7.0 Hz, 2H), 4.65 (qq, J = 6.1 Hz, 1H), 4.92 (s, 2H), 6.53 (d, J = 8.6 Hz, 2H), 6.70 (s, 1H), 6.98 (d, J = 8.9 Hz, 2H), 7.10 (d, J = 8.9 Hz, 2H), 7.11 (d, J = 8.6 Hz, 1H) |

TABLE 16-continued
| Compound No. | 1H-NMR (DMSO-d6) δ ppm |
|---|---|
| I-30 | 1.41 (6H, d, J = 5.9 Hz), 1.78-1.94 (2H, m), 2.00-2.11 (2H, m), 2.42 (2H, t, J = 10.9 Hz), 2.61-2.74 (1H, m), 3.46 (3H, s), 3.78 (2H, t, J = 4.7 Hz), 3.92 (2H, d, J = 11.6 Hz), 4.49 (2H, t, J = 4.7 Hz), 4.67 (1H, tt, J = 12.1. 6.1 Hz), 4.94 (2H, s), 6.62 (1H, d, J = 8.4 Hz), 6.74 (1H, s), 7.00 (2H, d, J = 8.9 Hz), 7.70-7.77 (3H, m). |
| I-31 | 1.39 (6H, d, J = 6.0 Hz), 1.75-1.93 (2H, m), 1.98-2.08 (2H, m), 2.32-2.45 (2H, m), 2.59-2.71 (1H, m), 3.89 (2H, d, J = 12.1 Hz), 4.65 (1H, tt, J = 12.0, 6.0 Hz), 4.93 (2H, s), 5.37 (2H, s), 6.60 (1H, d, J = 8.5 Hz), 6.71 (1H, s), 6.98 (2H, d, J = 8.4 Hz), 7.27-7.38 (3H, m), 7.45 (2H, dd, J = 7.2, 1.5 Hz), 7.68-7.74 (3H, m). |
| I-32 | 1.34 (5H, d, J = 6.1 Hz), 1.55-1.71 (2H, m), 1.93-2.05 (2H, m), 2.37 (2H, t, J = 11.3 Hz), 2.62-2.78 (1H, m), 3.75 (2H, d, J = 11.4 Hz), 4.73-4.84 (3H, m), 6.33 (1H, d, J = 8.3 Hz), 6.92 (1H, s), 7.17 (2H, d, J = 8.9 Hz), 7.70 (2H, d, J = 8.9 Hz), 7.77 (1H, d, J = 8.3 Hz). |
TABLE 17
| Comd. No. | Structure |
|---|---|
| II-1 | 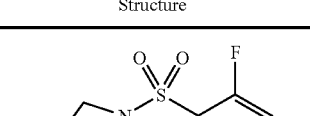 |
| II-2 | 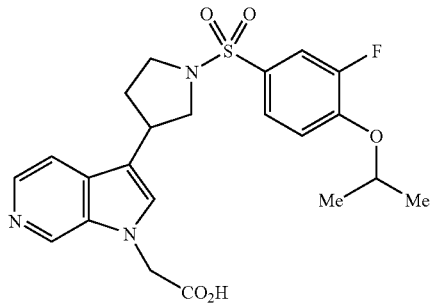 |
| II-3 | 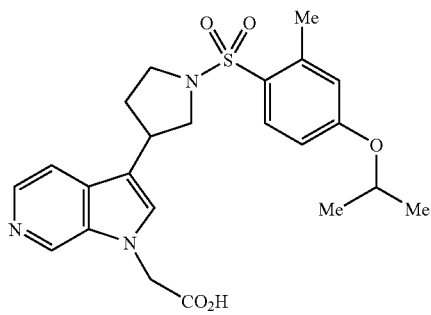 |
TABLE 17-continued
| Comd. No. | Structure |
|---|---|
| II-4 | 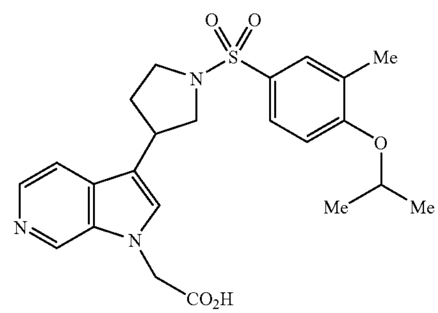 |
| II-5 | 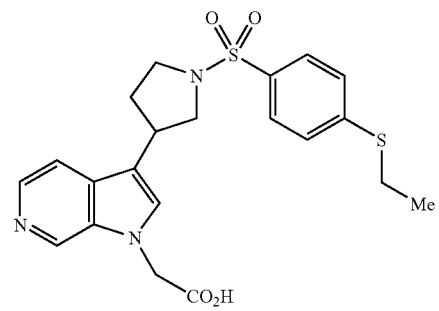 |
| II-6 | 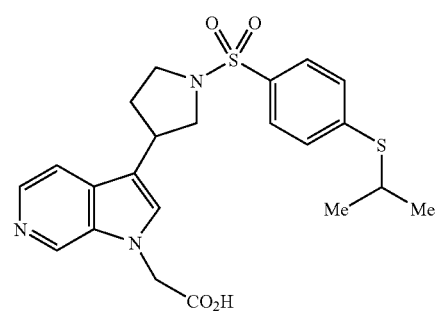 |

TABLE 17-continued

| Comd. No. | Structure |
|---|---|
| II-7 | (structure) |
| II-8 | (structure) |
| II-9 | (structure) |
| II-10 | (structure) |
| II-11 | (structure) |
| II-12 | (structure) |

TABLE 18

| Comd. No. | Structure |
|---|---|
| II-13 | (structure) |

TABLE 18-continued

| Cmpd. No. | Structure |
| --- | --- |
| II-14 | 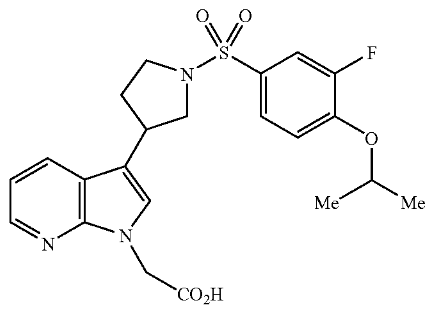 |
| II-15 | 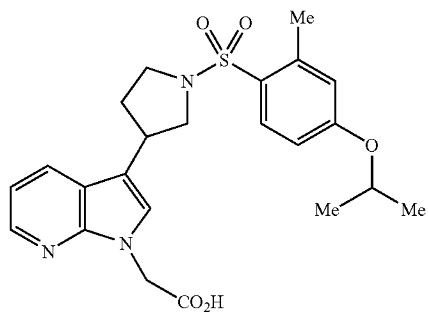 |
| II-16 | 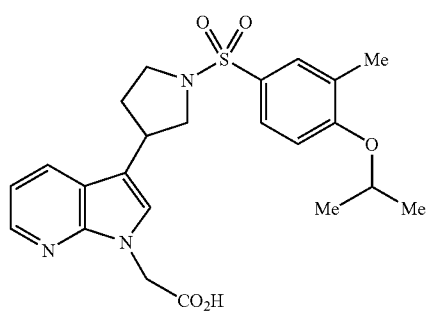 |
| II-17 | 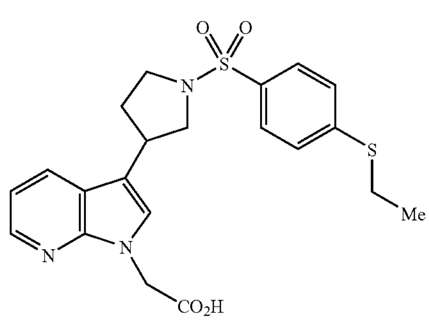 |

TABLE 18-continued
| Comd. No. | Structure |
|---|---|
| II-18 | 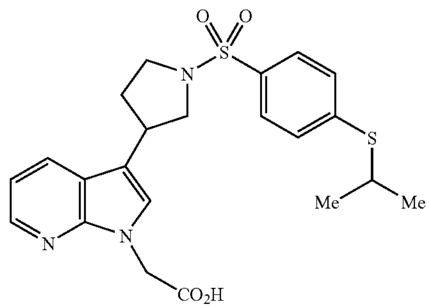 |
| II-19 | 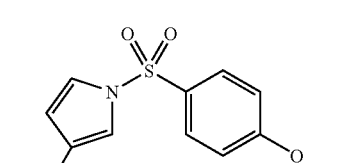 |
| II-20 | 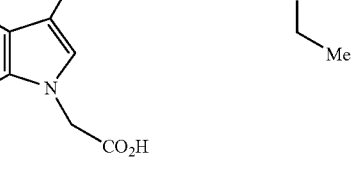 |
| II-21 | 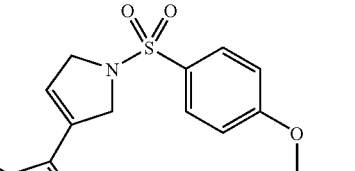 |
| II-22 | 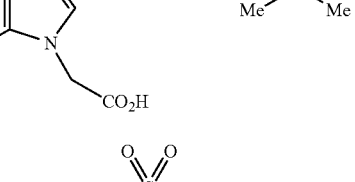 |

TABLE 18-continued

| Comd. No. | Structure |
|---|---|
| II-23 | (structure) |
| II-24 | (structure) |

TABLE 19

| Comd. No. | Structure |
|---|---|
| II-25 | (structure) |
| II-26 | (structure) |
| II-27 | (structure) |
| II-28 | (structure) |

TABLE 19-continued
| Comd. No. | Structure |
|---|---|
| II-29 | 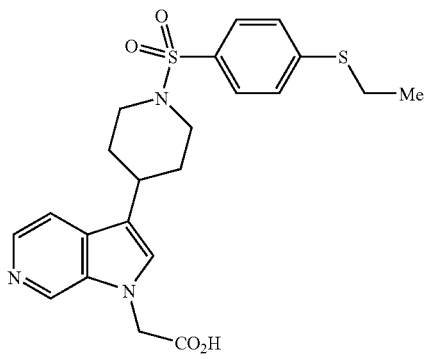 |
| II-30 | 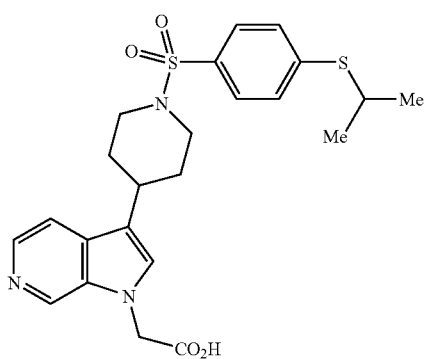 |
| II-31 | 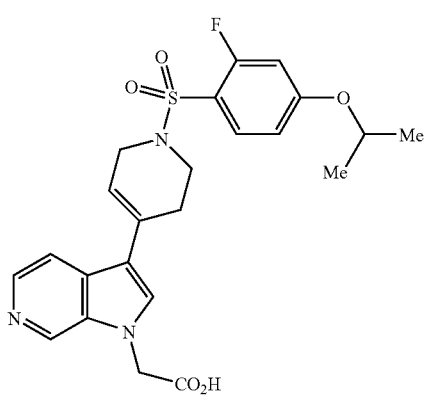 |
| II-32 | 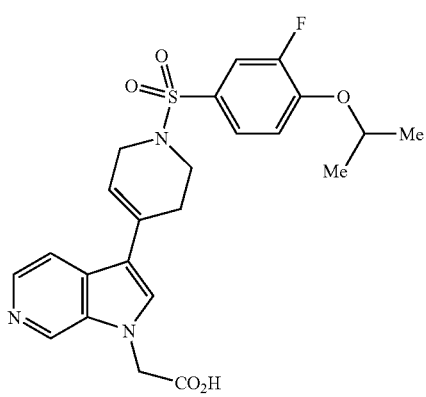 |
TABLE 19-continued
| Comd. No. | Structure |
|---|---|
| II-33 | 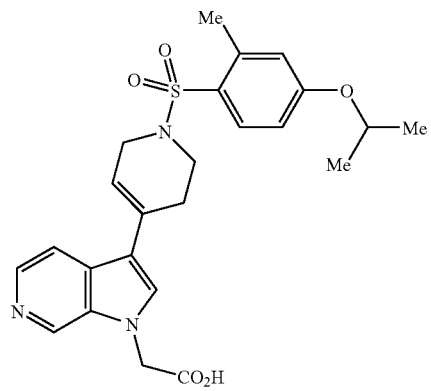 |
| II-34 | 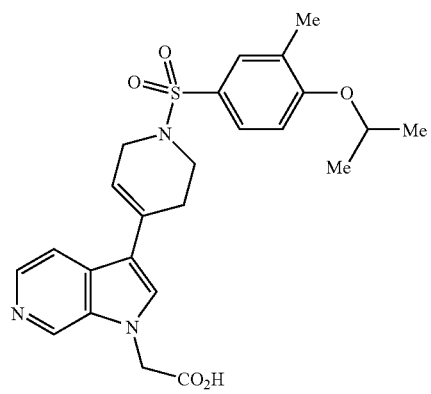 |
TABLE 20
| Comd. No. | Structure |
|---|---|
| II-35 | 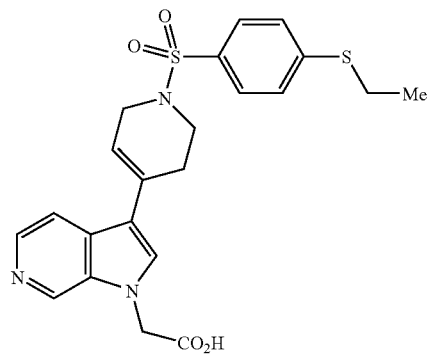 |

TABLE 20-continued

| Cmpd. No. | Structure |
|---|---|
| II-36 | (structure) |
| II-37 | (structure) |
| II-38 | (structure) |
| II-39 | (structure) |
| II-40 | (structure) |
| II-41 | (structure) |
| II-42 | (structure) |
| II-43 | (structure) |

TABLE 20-continued
| Comd. No. | Structure |
|---|---|
| II-44 | 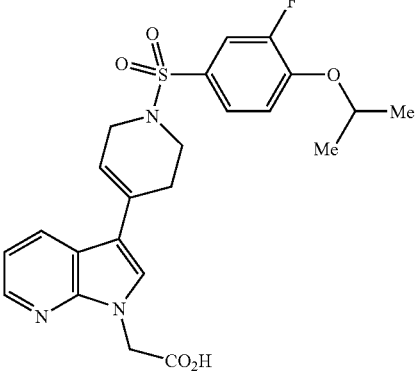 |
TABLE 21
| Comd. No. | Structure |
|---|---|
| II-45 | 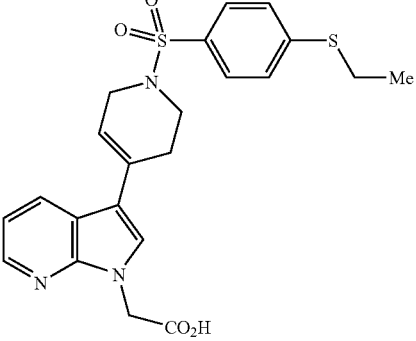 |
| II-46 | 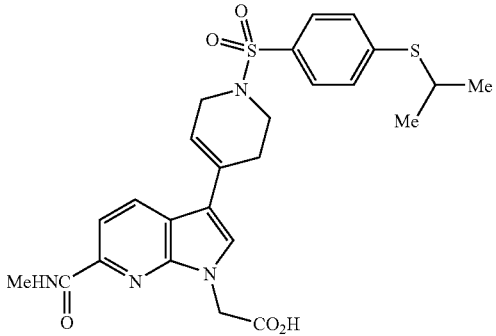 |
TABLE 21-continued
| Comd. No. | Structure |
|---|---|
| II-47 | 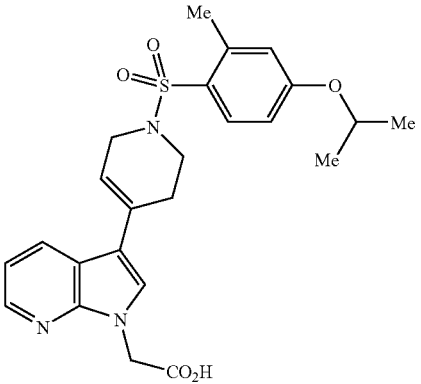 |
| II-48 | 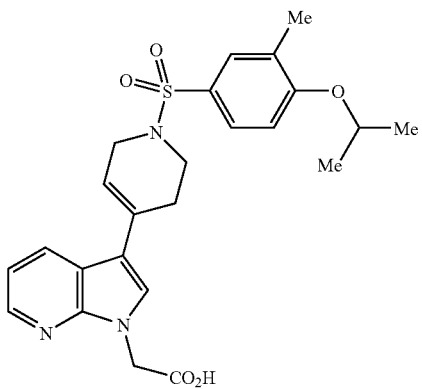 |
| II-49 | 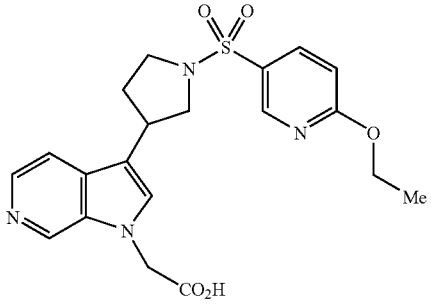 |
| II-50 | 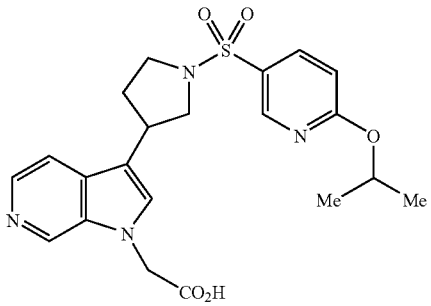 |

TABLE 21-continued
| Comd. No. | Structure |
|---|---|
| II-51 | 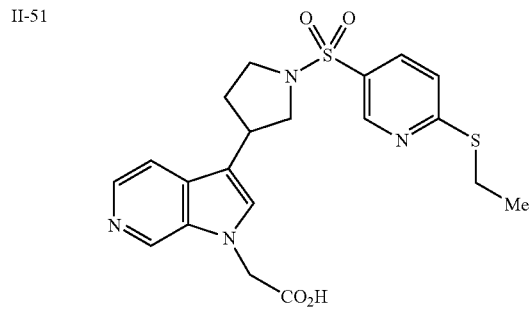 |
| II-52 | 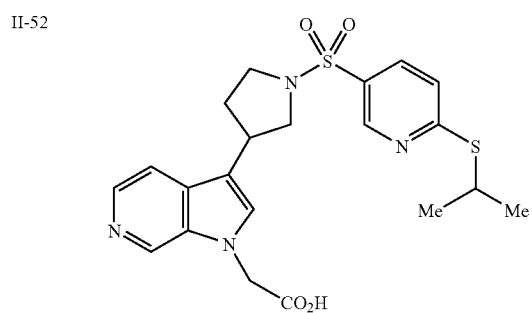 |
| II-53 | 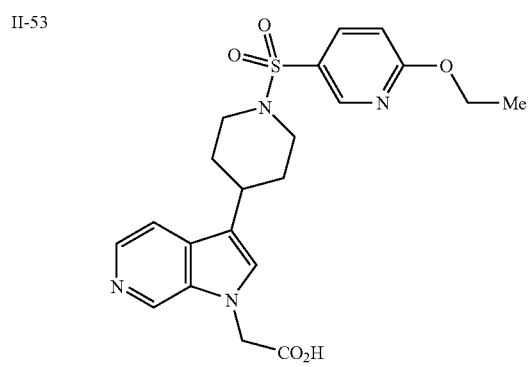 |
| II-54 | 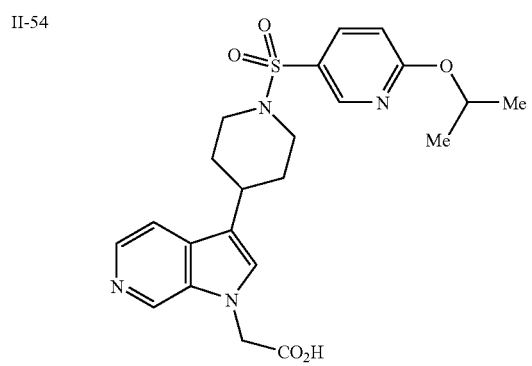 |
TABLE 21-continued
| Comd. No. | Structure |
|---|---|
| II-55 | 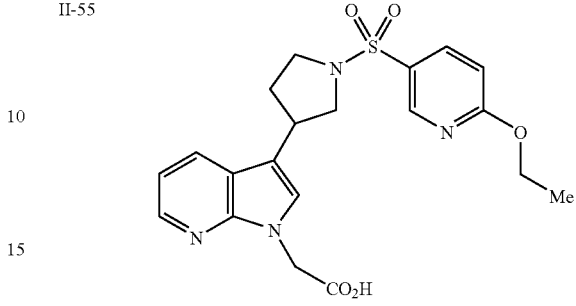 |
| II-56 | 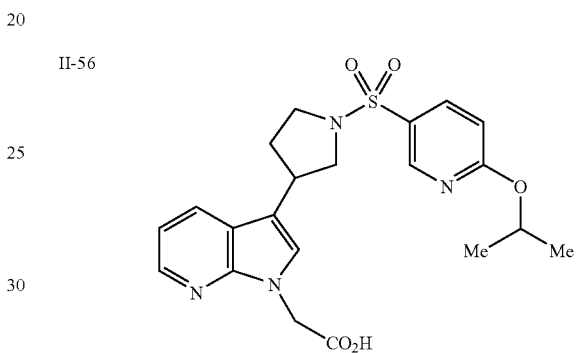 |
TABLE 22
| Comd. No. | Structure |
|---|---|
| II-57 | 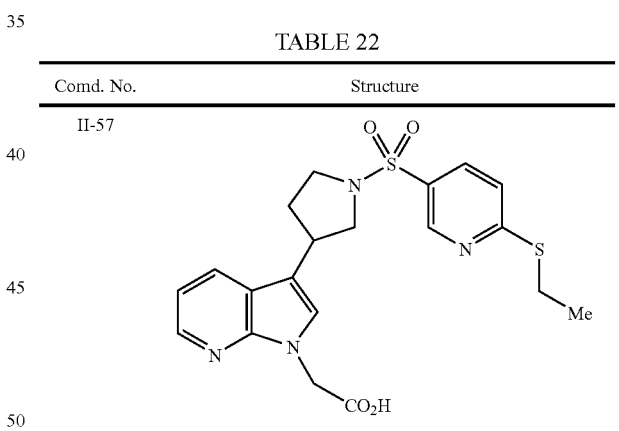 |
| II-58 | 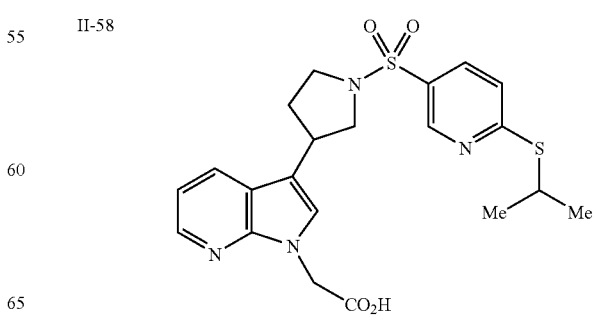 |

TABLE 22-continued
| Comd. No. | Structure |
|---|---|
| II-59 | 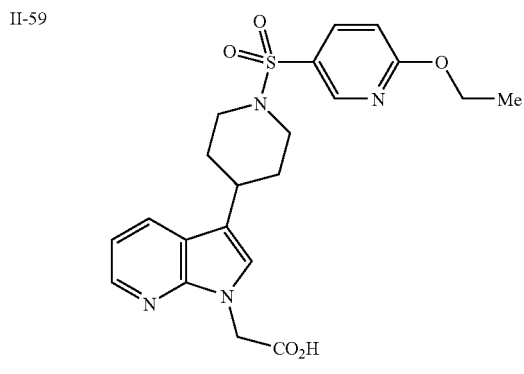 |
| II-61 | 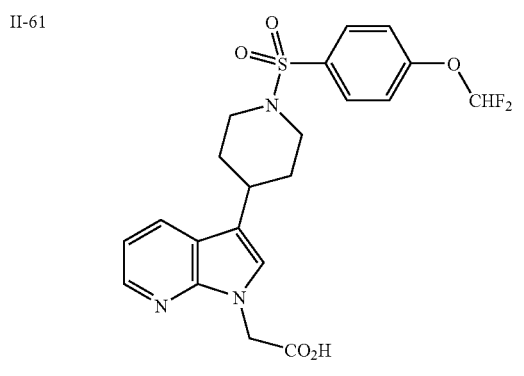 |
| II-62 | 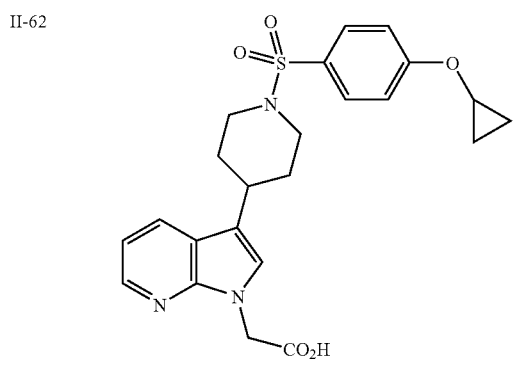 |
| II-63 | 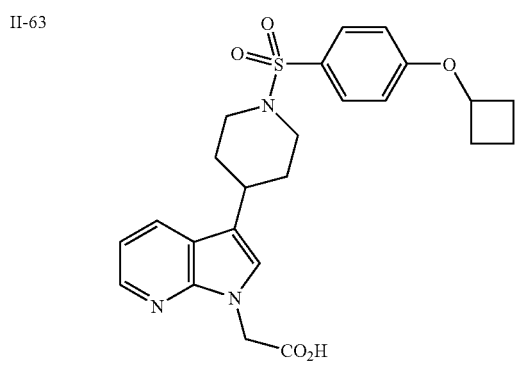 |
| II-64 | 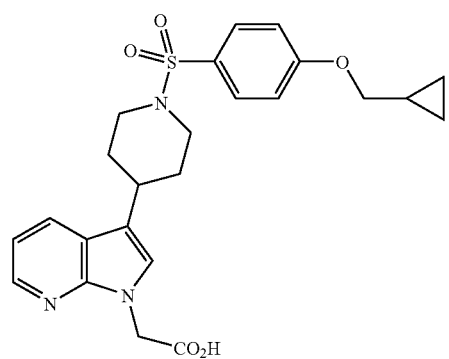 |
| II-65 | 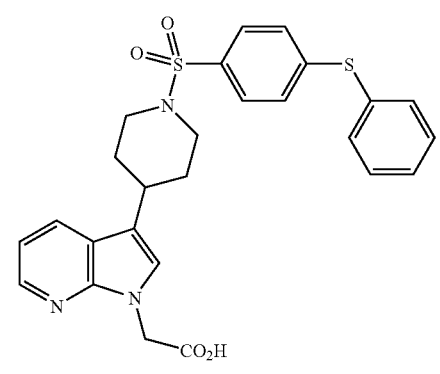 |
| II-66 | 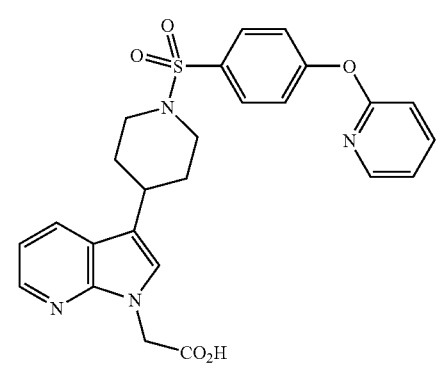 |
| II-67 | 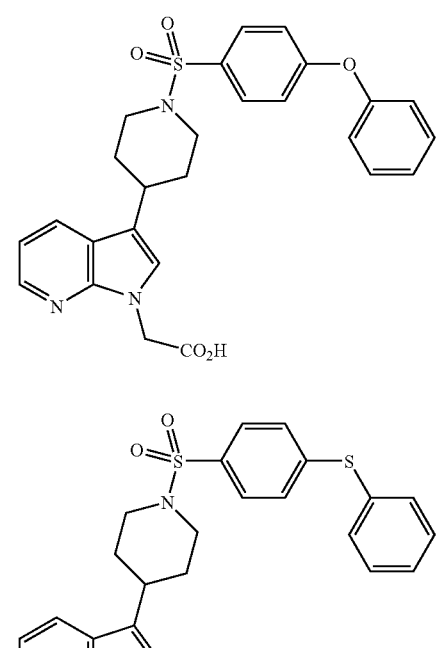 |

TABLE 22-continued
| Cmpd. No. | Structure |
|---|---|
| II-68 | 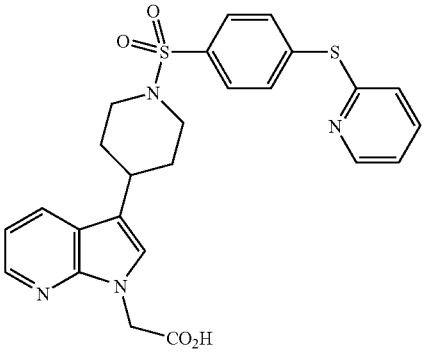 |
| II-69 | 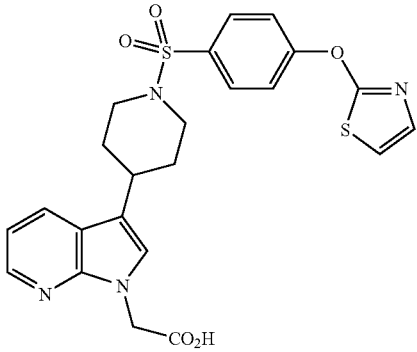 |
TABLE 23
| Cmpd. No. | Structure |
|---|---|
| II-70 | 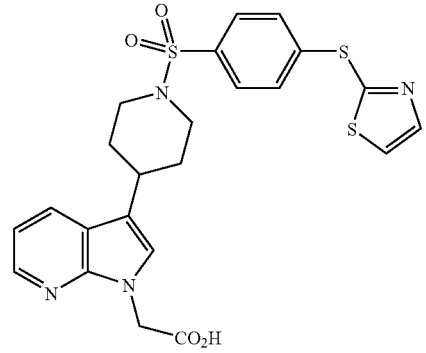 |
| II-71 | 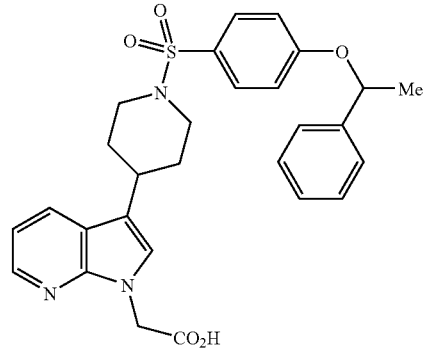 |
| II-72 | 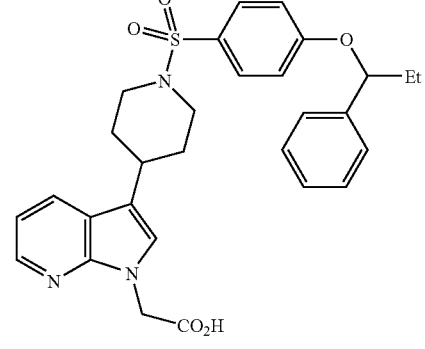 |

TABLE 23-continued
| Comd. No. | Structure |
|---|---|
| II-73 | 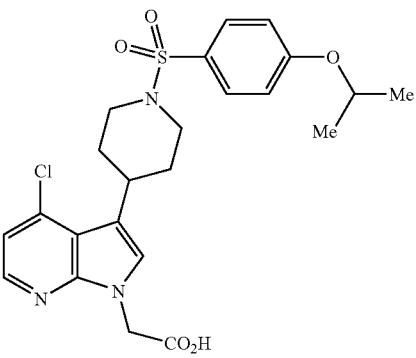 |
| II-74 | 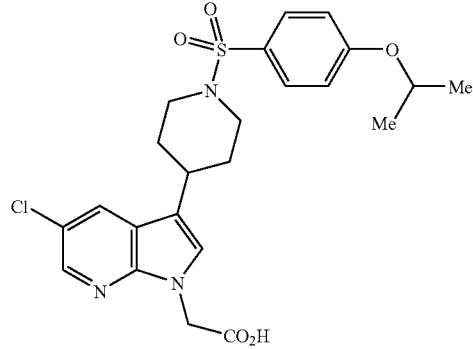 |
| II-76 | 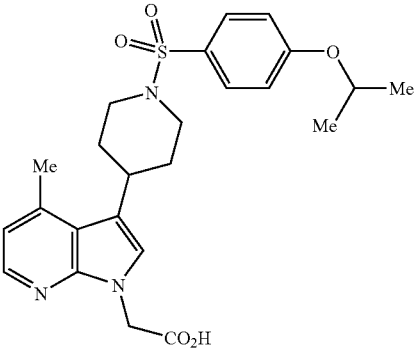 |
| II-77 | 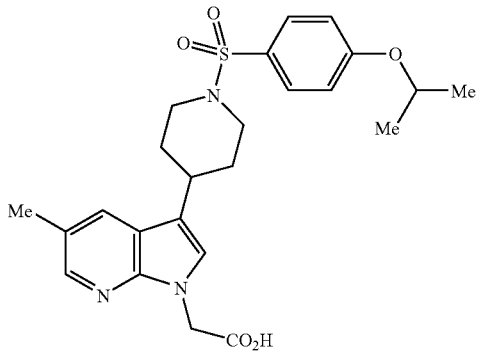 |

TABLE 23-continued
| Comd. No. | Structure |
|---|---|
| II-78 | 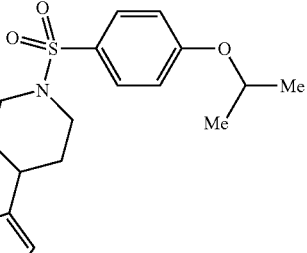 |
| II-79 | 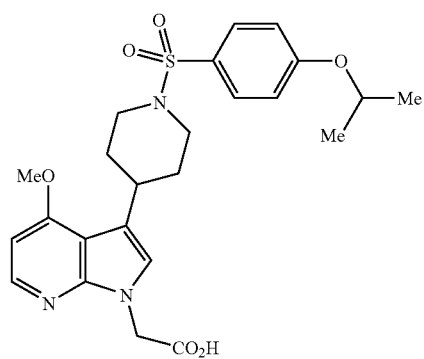 |
| II-80 | 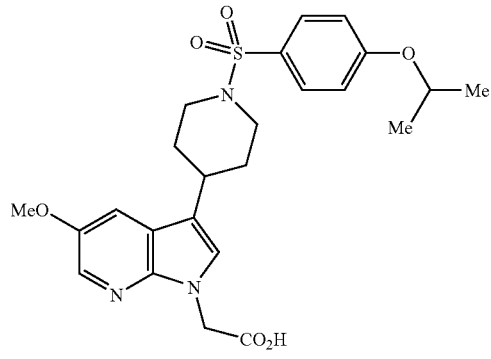 |
| II-82 | 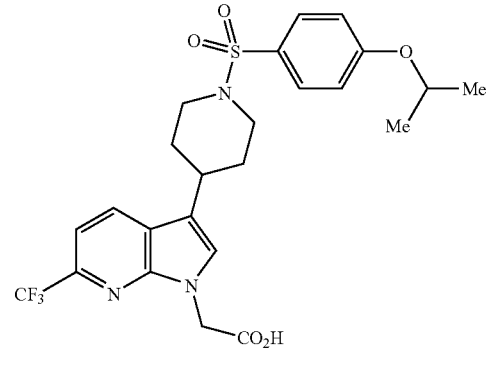 |

TABLE 23-continued
| Comd. No. | Structure |
|---|---|
| II-83 | 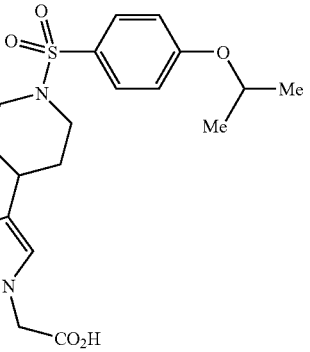 |
TABLE 24
| Comd. No. | Structure |
|---|---|
| II-84 | 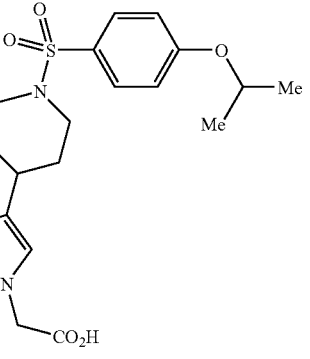 |
| II-85 | 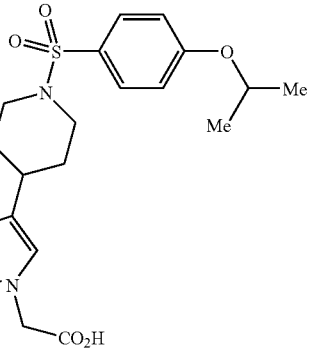 |
| II-86 | 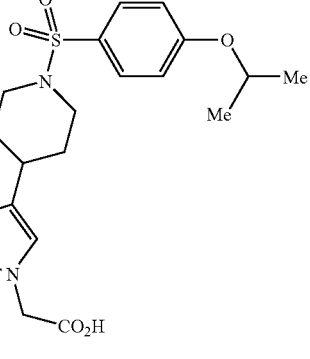 |

TABLE 24-continued
| Comd. No. | Structure |
|---|---|
| II-87 | 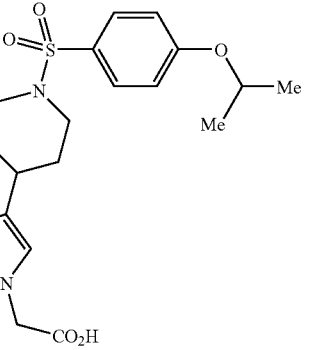 |
| II-88 | 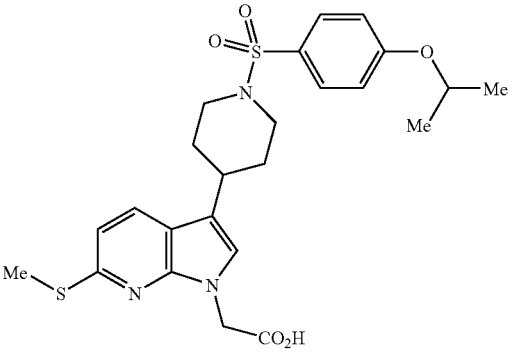 |
| II-89 | 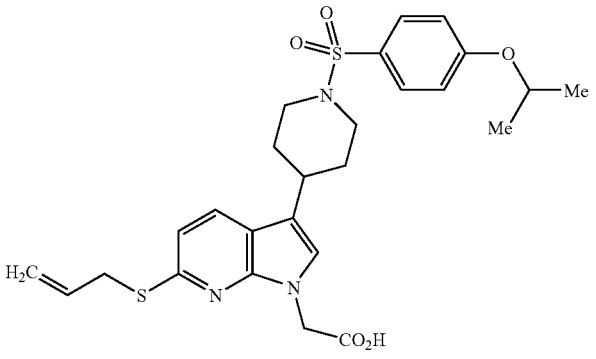 |
| II-90 | 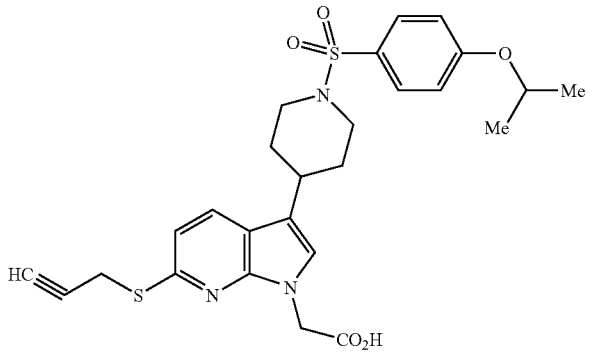 |

TABLE 24-continued

| Comd. No. | Structure |
|---|---|
| II-91 | 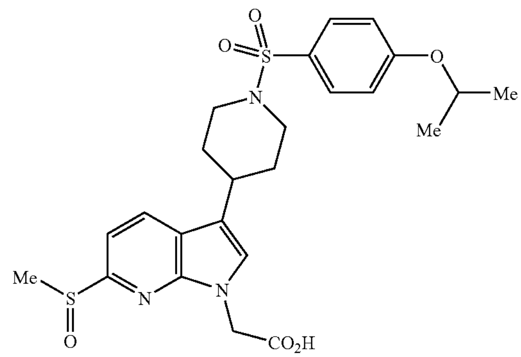 |
| II-92 | 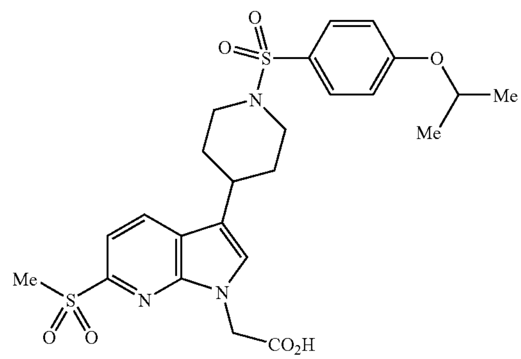 |
| II-93 | 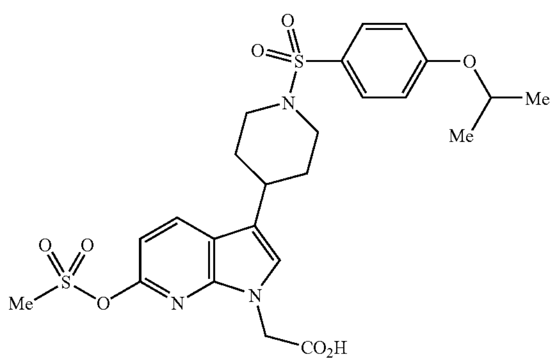 |

TABLE 25

| Comd. No. | Structure |
|---|---|
| II-95 | 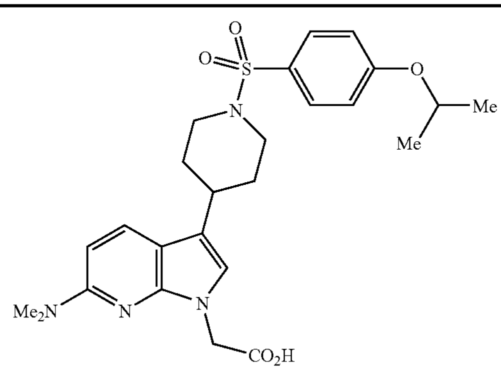 |

TABLE 25-continued
| Comd. No. | Structure |
|---|---|
| II-97 | 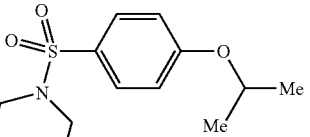 |
| II-98 | 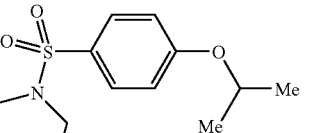 |
| II-99 | 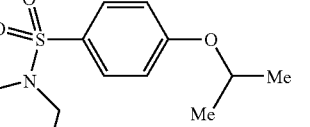 |
| II-100 | 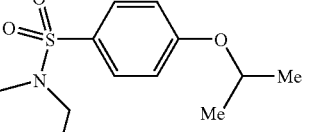 |

TABLE 25-continued

| Comd. No. | Structure |
|---|---|
| II-101 | (structure) |
| II-102 | (structure) |
| II-103 | (structure) |
| II-104 | (structure) |

TABLE 25-continued
| Cmpd. No. | Structure |
|---|---|
| II-105 | 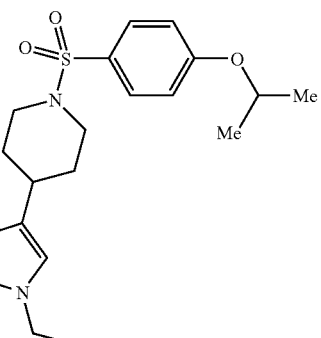 |
TABLE 26
| Cmpd. No. | Structure |
|---|---|
| II-110 | 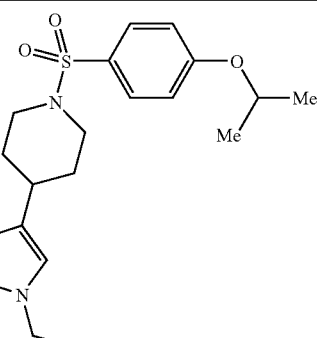 |
| II-111 | 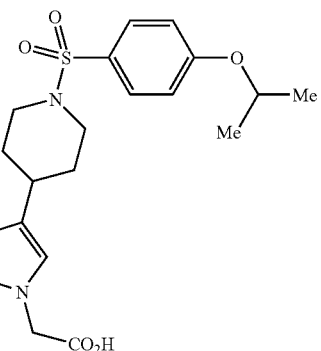 |
| II-112 | 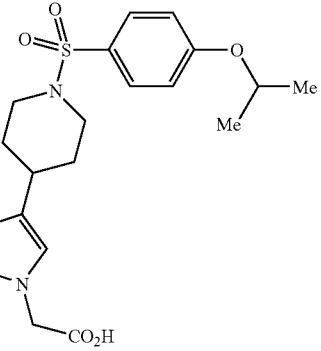 |

TABLE 26-continued
| Comd. No. | Structure |
|---|---|
| II-113 | 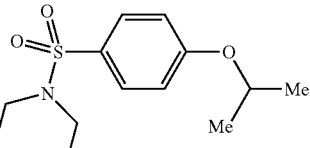 |
| II-114 | 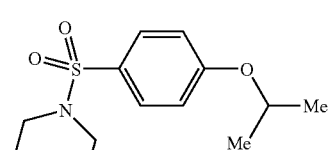 |
| II-115 | 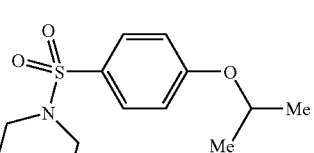 |
| II-116 | 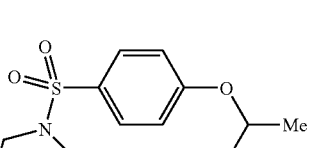 |

TABLE 26-continued

| Comd. No. | Structure |
|---|---|
| II-117 | 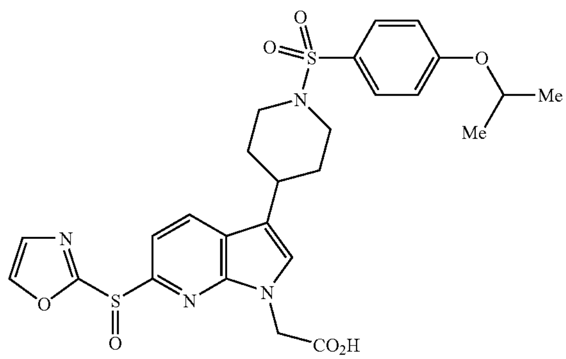 |
| II-118 | 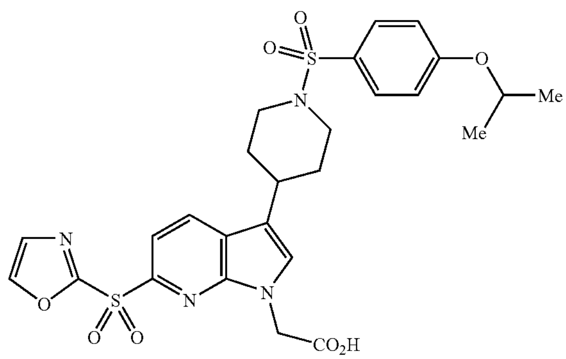 |
| II-119 | 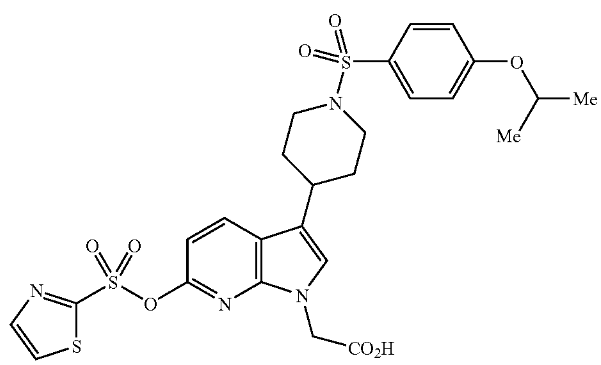 |

TABLE 27

| Comd. No. | Structure |
|---|---|
| II-120 | 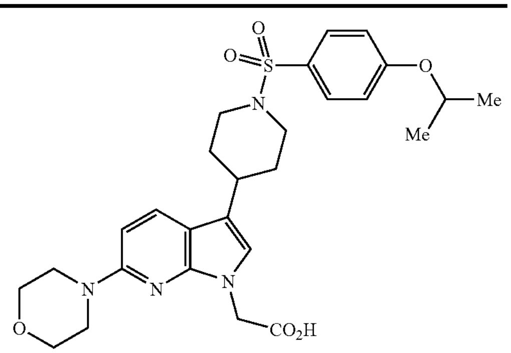 |

TABLE 27-continued

| Comd. No. | Structure |
|---|---|
| II-121 | 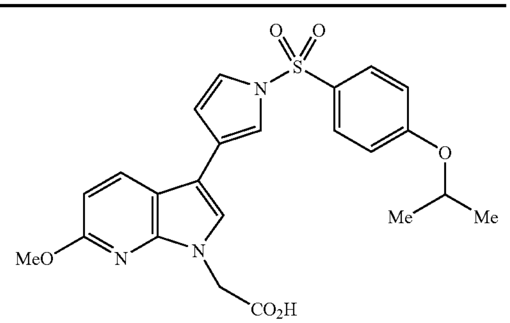 |

US 7,842,692 B2
TABLE 27-continued
| Comd. No. | Structure |
|---|---|
| II-121 | 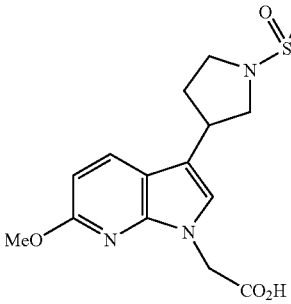 |
| II-123 | 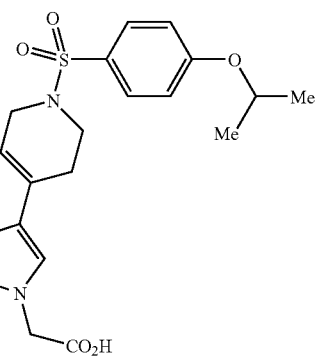 |
| II-124 | 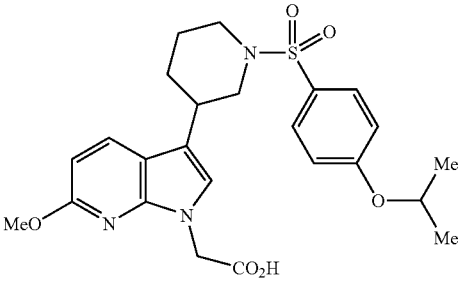 |
| II-125 | 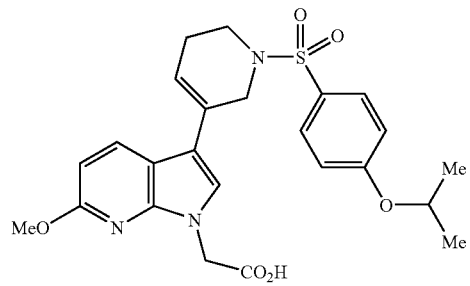 |
TABLE 27-continued
| Comd. No. | Structure |
|---|---|
| II-126 | 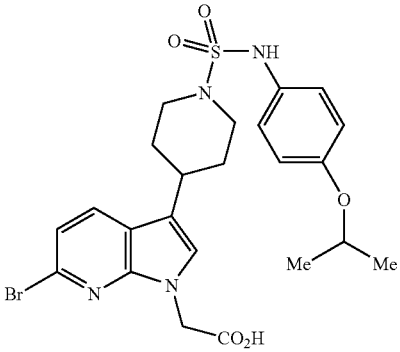 |
| II-127 | 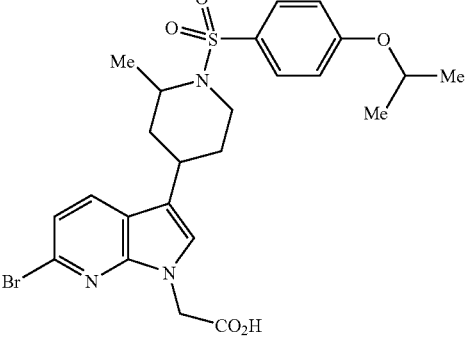 |
| II-128 | 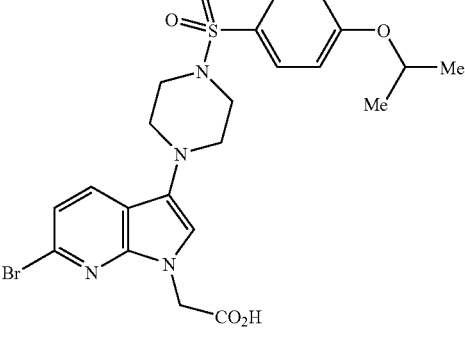 |
| II-129 | 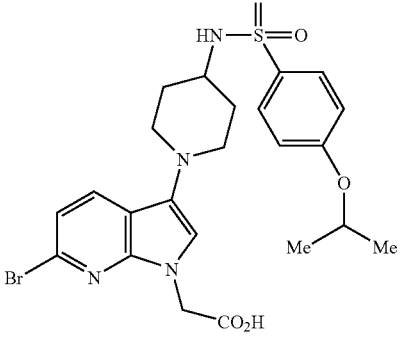 |

TABLE 27-continued
| Cmpd. No. | Structure |
|---|---|
| II-130 | 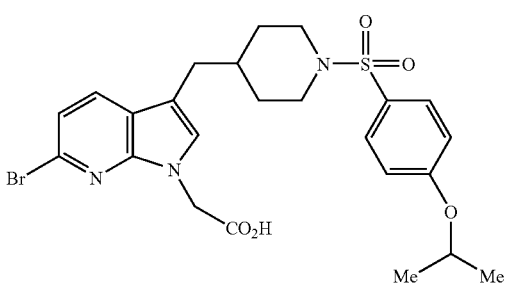 |
| II-131 | 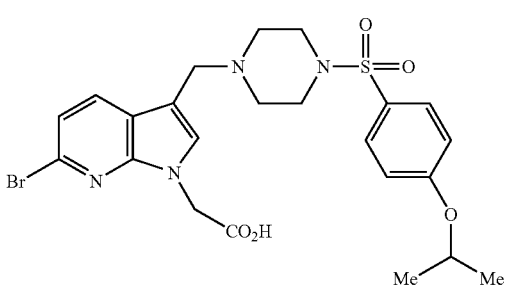 |
TABLE 28
| Cmpd. No. | Structure |
|---|---|
| II-132 | 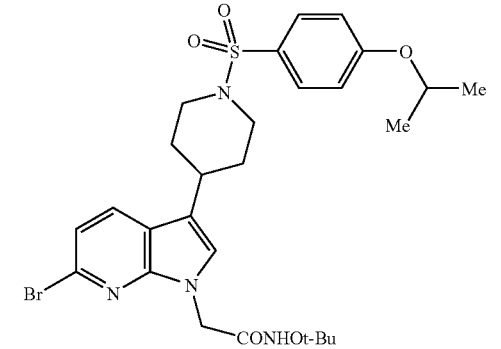 |
| II-133 | 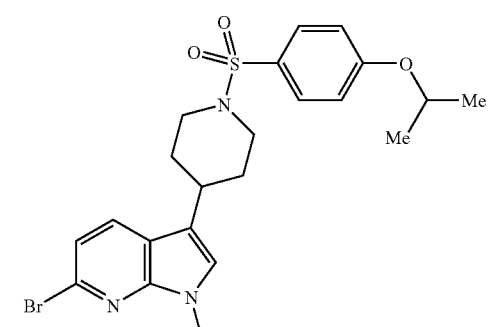 |
TABLE 28-continued
| Cmpd. No. | Structure |
|---|---|
| II-134 | 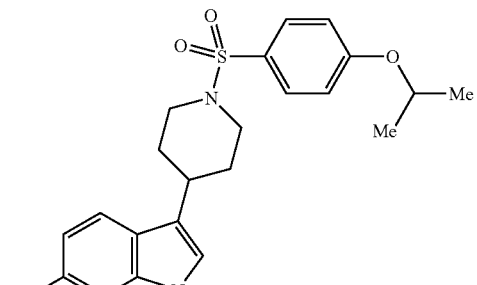 |
| II-135 | 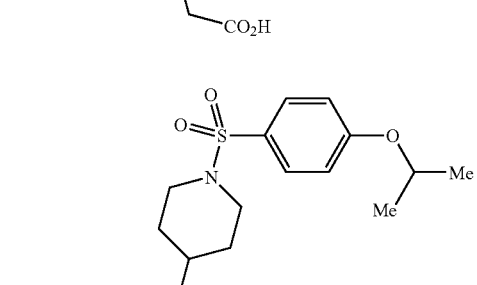 |
| II-136 | 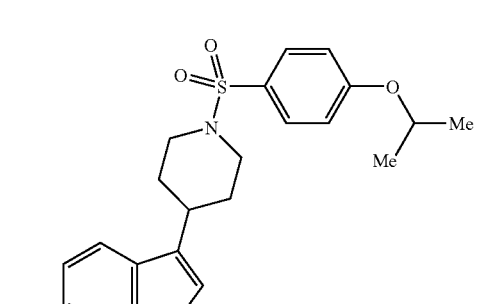 |
| II-137 | 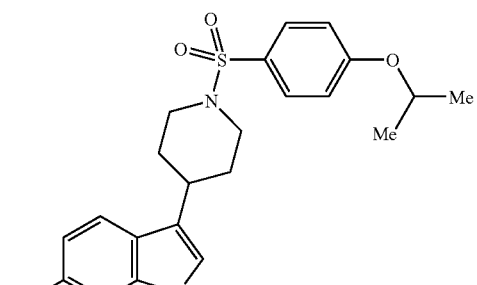 |

TABLE 28-continued

| Comd. No. | Structure |
|---|---|
| II-138 | (structure) |
| II-139 | (structure) |
| II-140 | (structure) |
| II-141 | (structure) |

TABLE 29

| Comd. No. | Structure |
|---|---|
| II-142 | (structure) |
| II-143 | (structure) |
| II-144 | (structure) |
| II-145 | (structure) |
| II-146 | (structure) |

TABLE 29-continued

| Comd. No. | Structure |
|---|---|
| II-147 | (structure with MeHNSO₂-azaindole, piperidine N-sulfonyl-4-(OiPr)phenyl, N-CH₂COOH) |
| II-148 | (structure with Me₂NSO₂-azaindole, piperidine N-sulfonyl-4-(OiPr)phenyl, N-CH₂COOH) |
| II-149 | (structure with PhHNSO₂-azaindole, piperidine N-sulfonyl-4-(OiPr)phenyl, N-CH₂COOH) |
| II-150 | (structure with Br-azaindole, piperidine N-C(O)-4-(OiPr)phenyl, N-CH₂COOH) |
| II-151 | (structure with Br-azaindole, piperidine N-C(O)-6-(OiPr)pyridin-3-yl, N-CH₂COOH) |
| II-152 | (structure with Br-azaindole, piperidine N-SO₂-CH₂-4-(OiPr)phenyl, N-CH₂COOH) |
| II-153 | (structure with Br-azaindole, piperidine N-C(O)-CH₂-4-(OiPr)phenyl, N-CH₂COOH) |

In addition, the compound of the next formula (IB):

(IB)

Structure with substituents $R^{1A}$, $R^{2A}$, $R^{3A}$, $R^{4A}$, $R^{5A}$, $R^{6A}$, $R^{7A}$, $R^{7B}$, $R^{7C}$, $R^{7D}$ on the azaindole-piperidine-sulfonylphenyl scaffold with N-CH₂COOH.

wherein $R^{1A}$ and $R^{2A}$ are independently a hydrogen atom, a fluorine atom, a chlorine atom, a bromine atom, methyl, ethyl, trifluoromethyl, methyloxy, ethyloxy, difluoromethyloxy, trifluoromethyloxy, methylthio, methylsulfinyl, methylsulfonyl, amino, methylamino, acetylamino, cyano, nitro, phenyl, 2-pyridyl, 2-furyl, 2-thienyl, 2-oxazolyl, 2-thiazolyl, pyrrolidino, piperidino, piperazino or morpholino;

$R^{3A}$ is a hydrogen atom, a chlorine atom, a bromine atom, methyl, methyloxy, ethyloxy, allyloxy, propargyloxy, methylthio, methylsulfinyl, methylsulfonyl, amino, methylamino, dimethylamino, acetylamino, acetyl, methyloxycarbonyl, N-methylcarbamoyl, N,N-dimethylcarbamoyl, phenyl, 4-fluorophenyl, 2-pyridyl, 3-pyridyl, 2-oxazolyl, 2-thiazolyl, pyrrolidino, piperidino, piperazino, morpholino, cyclopropylmethylamino, t-butoxycarbonylamino, 2-furyl, 3-furyl, 2-thienyl, 3-thienyl, 5-oxazolyl, a fluorine atom, phenoxy, cyano, nitro, carbamoyl, N-n-propylcarbamoyl, N-phenylcarbamoyl, methyloxycarbonylamino, i-propyloxycarbonylamino, 3-pyridylcarbonylamino, 2-furylcarbonylamino, 3-methyloxyphenyl, 4-methyloxyphenyl, 4-cyanophenyl, 4-oxazolyl, 5-methyl-2-oxazolyl, 3,4-oxadiazol-2-yl, 5-methyl-3,4-oxadiazol-2-yl, 3,4-thiadiazol-2-yl, 5-methyl-3,4-thiadiazol-2-yl, 4-pyridyl, 4-methyloxy-3-pyridyl, hydrazinocarbonyl, 1-pyrazolyl, 3,4-methylenedioxyphenyl, N-cyclopropylcarbamoyl, 4-isooxazolylcarbonylamino, 5-methylisooxazol-3-yl-carbonylamino, trifluoromethyl, or 3-methyloxypropargyl;

$R^{5A}$ is a hydrogen atom or methyl;

$R^{6A}$ is ethyloxy, isopropyloxy, 2,2-difluoromethyloxy or isopropylthio;

$R^{7A}$, $R^{7B}$, $R^{7C}$ and $R^{7D}$ are independently a hydrogen atom a fluorine atom or methyl, can be synthesized in the same manner as set forth above.

Combinations of $R^{1A}$, $R^{2A}$, $R^{3A}$ and $R^{5A}$ (part A) are shown in Tables 30-35. Combinations of $R^{6A}$, $R^{7A}$, $R^{7B}$, $R^{7C}$ and $R^{7D}$ (part B) are shown in Tables 36-37.

TABLE 30

| No. | $R^{1A}$ | $R^{2A}$ | $R^{3A}$ | $R^{5A}$ |
| --- | --- | --- | --- | --- |
| A-1 | H | H | H | H |
| A-2 | F | H | H | H |
| A-3 | Cl | H | H | H |
| A-4 | Br | H | H | H |
| A-5 | Me | H | H | H |
| A-6 | Et | H | H | H |
| A-7 | CF3 | H | H | H |
| A-8 | OMe | H | H | H |
| A-9 | OEt | H | H | H |
| A-10 | OCHF₂ | H | H | H |
| A-11 | SMe | H | H | H |
| A-12 | SOMe | H | H | H |
| A-13 | SO₂Me | H | H | H |
| A-14 | NH₂ | H | H | H |
| A-15 | NHMe | H | H | H |
| A-16 | NHAc | H | H | H |
| A-17 | CN | H | H | H |
| A-18 | NO₂ | H | H | H |
| A-19 | Ph | H | H | H |
| A-20 | 2-pyridyl | H | H | H |
| A-21 | 2-furyl | H | H | H |
| A-22 | 2-thienyl | H | H | H |
| A-23 | pyrrolidino | H | H | H |
| A-24 | piperidino | H | H | H |
| A-25 | piperazino | H | H | H |
| A-26 | morpholino | H | H | H |
| A-27 | H | F | H | H |
| A-28 | H | Cl | H | H |
| A-29 | H | Br | H | H |
| A-30 | H | Me | H | H |
| A-31 | H | Et | H | H |

TABLE 30-continued

| No. | $R^{1A}$ | $R^{2A}$ | $R^{3A}$ | $R^{5A}$ |
| --- | --- | --- | --- | --- |
| A-32 | H | CF3 | H | H |
| A-33 | H | OMe | H | H |
| A-34 | H | OEt | H | H |
| A-35 | H | OCHF₂ | H | H |
| A-36 | H | SMe | H | H |
| A-37 | H | SOMe | H | H |
| A-38 | H | SO₂Me | H | H |
| A-39 | H | NH₂ | H | H |
| A-40 | H | NHMe | H | H |
| A-41 | H | NHAc | H | H |
| A-42 | H | CN | H | H |
| A-43 | H | NO₂ | H | H |
| A-44 | H | Ph | H | H |
| A-45 | H | 2-pyridyl | H | H |
| A-46 | H | 2-furyl | H | H |
| A-47 | H | 2-thienyl | H | H |
| A-48 | H | pyrrolidino | H | H |

TABLE 31

| No. | $R^{1A}$ | $R^{2A}$ | $R^{3A}$ | $R^{5A}$ |
| --- | --- | --- | --- | --- |
| A-49 | H | piperidino | H | H |
| A-50 | H | piperazino | H | H |
| A-51 | H | morpholino | H | H |
| A-52 | H | H | H | Me |
| A-53 | F | H | H | Me |
| A-54 | Cl | H | H | Me |
| A-55 | Br | H | H | Me |
| A-56 | Me | H | H | Me |
| A-57 | Et | H | H | Me |
| A-58 | CF3 | H | H | Me |
| A-59 | OMe | H | H | Me |
| A-60 | OEt | H | H | Me |
| A-61 | OCHF₂ | H | H | Me |
| A-62 | SMe | H | H | Me |
| A-63 | SOMe | H | H | Me |
| A-64 | SO₂Me | H | H | Me |
| A-65 | NH₂ | H | H | Me |
| A-66 | NHMe | H | H | Me |
| A-67 | NHAc | H | H | Me |
| A-68 | CN | H | H | Me |
| A-69 | NO₂ | H | H | Me |
| A-70 | Ph | H | H | Me |
| A-71 | 2-pyridyl | H | H | Me |
| A-72 | 2-furyl | H | H | Me |
| A-73 | 2-thienyl | H | H | Me |
| A-74 | pyrrolidino | H | H | Me |
| A-75 | piperidino | H | H | Me |
| A-76 | piperazino | H | H | Me |
| A-77 | morpholino | H | H | Me |
| A-78 | H | F | H | Me |
| A-79 | H | Cl | H | Me |
| A-80 | H | Br | H | Me |
| A-81 | H | Me | H | Me |
| A-82 | H | Et | H | Me |
| A-83 | H | CF3 | H | Me |
| A-84 | H | OMe | H | Me |
| A-85 | H | OEt | H | Me |
| A-86 | H | OCHF₂ | H | Me |
| A-87 | H | SMe | H | Me |
| A-88 | H | SOMe | H | Me |
| A-89 | H | SO₂Me | H | Me |
| A-90 | H | NH₂ | H | Me |
| A-91 | H | NHMe | H | Me |
| A-92 | H | NHAc | H | Me |
| A-93 | H | CN | H | Me |
| A-94 | H | NO₂ | H | Me |
| A-95 | H | Ph | H | Me |
| A-96 | H | 2-pyridyl | H | Me |

TABLE 32

| No. | $R^{1A}$ | $R^{2A}$ | $R^{3A}$ | $R^{5A}$ |
|---|---|---|---|---|
| A-97 | H | 2-furyl | H | Me |
| A-98 | H | 2-thienyl | H | Me |
| A-99 | H | pyrrolidino | H | Me |
| A-100 | H | piperidino | H | Me |
| A-101 | H | piperazino | H | Me |
| A-102 | H | morpholino | H | Me |
| A-103 | F | H | Cl | H |
| A-104 | F | H | Br | H |
| A-105 | F | H | Me | H |
| A-106 | F | H | Et | H |
| A-107 | F | H | OMe | H |
| A-108 | F | H | OEt | H |
| A-109 | F | H | allyloxy | H |
| A-110 | F | H | propargyloxy | H |
| A-111 | F | H | SMe | H |
| A-112 | F | H | SOMe | H |
| A-113 | F | H | $SO_2Me$ | H |
| A-114 | F | H | $NH_2$ | H |
| A-115 | F | H | NHMe | H |
| A-116 | F | H | $NMe_2$ | H |
| A-117 | F | H | NHAc | H |
| A-118 | F | H | Ac | H |
| A-119 | F | H | COOMe | H |
| A-120 | F | H | CONHMe | H |
| A-121 | F | H | $CONMe_2$ | H |
| A-122 | F | H | Ph | H |
| A-123 | F | H | 4-F-phenyl | H |
| A-124 | F | H | 2-pyridyl | H |
| A-125 | F | H | 3-pyridyl | H |
| A-126 | F | H | 2-oxazolyl | H |
| A-127 | F | H | 2-thiazolyl | H |
| A-128 | F | H | pyrrolidino | H |
| A-129 | F | H | piperidino | H |
| A-130 | F | H | piperazino | H |
| A-131 | Cl | H | morpholino | H |
| A-132 | Cl | H | Cl | H |
| A-133 | Cl | H | Br | H |
| A-134 | Cl | H | Me | H |
| A-135 | Cl | H | Et | H |
| A-136 | Cl | H | OMe | H |
| A-137 | Cl | H | OEt | H |
| A-138 | Cl | H | allyloxy | H |
| A-139 | Cl | H | propargyloxy | H |
| A-140 | Cl | H | SMe | H |
| A-141 | Cl | H | SOMe | H |
| A-142 | Cl | H | $SO_2Me$ | H |
| A-143 | Cl | H | $NH_2$ | H |
| A-144 | Cl | H | NHMe | H |

TABLE 33

| No. | $R^{1A}$ | $R^{2A}$ | $R^{3A}$ | $R^{5A}$ |
|---|---|---|---|---|
| A-145 | Cl | H | $NMe_2$ | H |
| A-146 | Cl | H | NHAc | H |
| A-147 | Cl | H | Ac | H |
| A-148 | Cl | H | COOMe | H |
| A-149 | Cl | H | CONHMe | H |
| A-150 | Cl | H | $CONMe_2$ | H |
| A-151 | Cl | H | Ph | H |
| A-152 | Cl | H | 4-F-phenyl | H |
| A-153 | Cl | H | 2-pyridyl | H |
| A-154 | Cl | H | 3-pyridyl | H |
| A-155 | Cl | H | 2-oxazolyl | H |
| A-156 | Cl | H | 2-thiazolyl | H |
| A-157 | Cl | H | pyrrolidino | H |
| A-158 | Cl | H | piperidino | H |
| A-159 | Cl | H | piperazino | H |
| A-160 | Cl | H | morpholino | H |
| A-161 | H | Cl | OMe | H |
| A-162 | Br | H | Cl | H |
| A-163 | Br | H | Br | H |
| A-164 | Br | H | Me | H |
| A-165 | Br | H | Et | H |
| A-166 | Br | H | OMe | H |
| A-167 | Br | H | OEt | H |
| A-168 | Br | H | allyloxy | H |
| A-169 | Br | H | propargyloxy | H |
| A-170 | Br | H | SMe | H |
| A-171 | Br | H | SOMe | H |
| A-172 | Br | H | $SO_2Me$ | H |
| A-173 | Br | H | $NH_2$ | H |
| A-174 | Br | H | NHMe | H |
| A-175 | Br | H | $NMe_2$ | H |
| A-176 | Br | H | NHAc | H |
| A-177 | Br | H | Ac | H |
| A-178 | Br | H | COOMe | H |
| A-179 | Br | H | CONHMe | H |
| A-180 | Br | H | $CONMe_2$ | H |
| A-181 | Br | H | Ph | H |
| A-182 | Br | H | 4-F-phenyl | H |
| A-183 | Br | H | 2-pyridyl | H |
| A-184 | Br | H | 3-pyridyl | H |
| A-185 | Br | H | 2-oxazolyl | H |
| A-186 | Br | H | 2-thiazolyl | H |
| A-187 | Br | H | pyrrolidino | H |
| A-188 | Br | H | piperidino | H |
| A-189 | Br | H | piperazino | H |
| A-190 | Br | H | morpholino | H |
| A-191 | H | Br | OMe | H |
| A-192 | Me | H | Cl | H |
| A-193 | Me | H | Br | H |

TABLE 34

| No. | $R^{1A}$ | $R^{2A}$ | $R^{3A}$ | $R^{5A}$ |
|---|---|---|---|---|
| A-194 | Me | H | Me | H |
| A-195 | Me | H | Et | H |
| A-196 | Me | H | OMe | H |
| A-197 | Me | H | OEt | H |
| A-198 | Me | H | allyloxy | H |
| A-199 | Me | H | propargyloxy | H |
| A-200 | Me | H | SMe | H |
| A-201 | Me | H | SOMe | H |
| A-202 | Me | H | $SO_2Me$ | H |
| A-203 | Me | H | $NH_2$ | H |
| A-204 | Me | H | NHMe | H |
| A-205 | Me | H | $NMe_2$ | H |
| A-206 | Me | H | NHAc | H |
| A-207 | Me | H | Ac | H |
| A-208 | Me | H | COOMe | H |
| A-209 | Me | H | CONHMe | H |
| A-210 | Me | H | $CONMe_2$ | H |
| A-211 | Me | H | Ph | H |
| A-212 | Me | H | 4-F-phenyl | H |
| A-213 | Me | H | 2-pyridyl | H |
| A-214 | Me | H | 3-pyridyl | H |
| A-215 | Me | H | 2-oxazolyl | H |
| A-216 | Me | H | 2-thiazolyl | H |
| A-217 | Me | H | pyrrolidino | H |
| A-218 | Me | H | piperidino | H |
| A-219 | Me | H | piperazmo | H |
| A-220 | Me | H | morpholino | H |
| A-221 | H | H | Cl | H |
| A-222 | H | H | Br | H |
| A-223 | H | H | Me | H |
| A-224 | H | H | Et | H |
| A-225 | H | H | OMe | H |
| A-226 | H | H | OEt | H |
| A-227 | H | H | allyloxy | H |
| A-228 | H | H | propargyloxy | H |
| A-229 | H | H | SMe | H |
| A-230 | H | H | SOMe | H |
| A-231 | H | H | $SO_2Me$ | H |
| A-232 | H | H | $NH_2$ | H |
| A-233 | H | H | NHMe | H |
| A-234 | H | H | $NMe_2$ | H |

TABLE 34-continued

| No. | $R^{1A}$ | $R^{2A}$ | $R^{3A}$ | $R^{5A}$ |
|---|---|---|---|---|
| A-235 | H | H | NHAc | H |
| A-236 | H | H | Ac | H |
| A-237 | H | H | COOMe | H |
| A-238 | H | H | CONHMe | H |
| A-239 | H | H | CONMe$_2$ | H |
| A-240 | H | H | Ph | H |
| A-241 | H | H | 4-F-phenyl | H |

TABLE 35

| No. | $R^{1A}$ | $R^{2A}$ | $R^{3A}$ | $R^{5A}$ |
|---|---|---|---|---|
| A-242 | H | H | 2-pyridyl | H |
| A-243 | H | H | 3-pyridyl | H |
| A-244 | H | H | 2-oxazolyl | H |
| A-245 | H | H | 2-thiazolyl | H |
| A-246 | H | H | pyrrolidino | H |
| A-247 | H | H | piperidino | H |
| A-248 | H | H | piperazmo | H |
| A-249 | H | H | morpholino | H |
| A-250 | H | H | NH(cyclopropylmethyl) | H |
| A-251 | H | H | NHBoc | H |
| A-252 | H | H | 2-furyl | H |
| A-253 | H | H | 3-furyl | H |
| A-254 | H | H | 2-thienyl | H |
| A-255 | H | H | 3-thienyl | H |
| A-256 | H | H | 5-oxazolyl | H |
| A-257 | H | F | OMe | H |
| A-258 | H | Me | OMe | H |
| A-259 | H | H | F | H |
| A-260 | H | H | OPh | H |
| A-261 | H | H | CN | H |
| A-262 | H | H | NO$_2$ | H |
| A-263 | H | H | CONH$_2$ | H |
| A-264 | H | H | CONHn-Pr | H |
| A-265 | H | H | CONHPh | H |
| A-266 | H | H | NHCOOMe | H |
| A-267 | H | H | NHCOOi-Pr | H |
| A-268 | H | H | NHCO(3-pyridyl) | H |
| A-269 | H | H | NHCO(2-furyl) | H |
| A-270 | H | H | 3-methyloxyphenyl | H |
| A-271 | H | H | 4-methyloxyphenyl | H |
| A-272 | H | H | 4-cyanophenyl | H |
| A-273 | H | H | 4-oxazolyl | H |
| A-274 | H | H | 5-Me-2-oxazolyl | H |
| A-275 | H | H | 3,4-oxadiazol-2yl | H |
| A-276 | H | H | 5-Me-3,4-oxadiazol-2yl | H |
| A-277 | H | H | 3,4-thiadiazol-2yl | H |
| A-278 | H | H | 5-Me-3,4-thiadiazol-2yl | H |
| A-279 | H | H | 4-pyridyl | H |
| A-280 | H | H | 4-methyloxy3-pyridyl | H |
| A-281 | H | H | CONHNH$_2$ | H |
| A-282 | H | H | 1-pyrazolyl | H |
| A-283 | H | H | 3,4-methylenedioxy-phenyl | H |
| A-284 | H | H | CONH(cyclopropyl) | H |
| A-285 | H | H | NHCO(4-isoxazolyl) | H |
| A-286 | H | H | NHCO(5-Me-isoxazol-3-yl) | H |
| A-287 | H | H | CF$_3$ | H |
| A-288 | H | H | 3-methyloxypropargyl | H |

TABLE 36

| No. | $R^{6A}$ | $R^{7A}$ | $R^{7B}$ | $R^{7C}$ | $R^{7D}$ |
|---|---|---|---|---|---|
| B-1 | OEt | H | H | H | H |
| B-2 | OCHMe$_2$ | H | H | H | H |
| B-3 | OCHF$_2$ | H | H | H | H |
| B-4 | SCHMe$_2$ | H | H | H | H |
| B-5 | OEt | F | H | H | H |
| B-6 | OEt | Me | H | H | H |

TABLE 36-continued

| No. | $R^{6A}$ | $R^{7A}$ | $R^{7B}$ | $R^{7C}$ | $R^{7D}$ |
|---|---|---|---|---|---|
| B-7 | OEt | H | F | H | H |
| B-8 | OEt | H | Me | H | H |
| B-9 | OEt | F | F | H | H |
| B-10 | OEt | F | H | F | H |
| B-11 | OEt | F | H | H | F |
| B-12 | OEt | F | Me | H | H |
| B-13 | OEt | F | H | Me | H |
| B-14 | OEt | F | H | H | Me |
| B-15 | OEt | Me | F | H | H |
| B-16 | OEt | Me | H | F | H |
| B-17 | OEt | Me | H | H | F |
| B-18 | OEt | Me | Me | H | H |
| B-19 | OEt | Me | H | Me | H |
| B-20 | OEt | Me | H | H | Me |
| B-21 | OCHMe$_2$ | F | H | H | H |
| B-22 | OCHMe$_2$ | Me | H | H | H |
| B-23 | OCHMe$_2$ | H | F | H | H |
| B-24 | OCHMe$_2$ | H | Me | H | H |
| B-25 | OCHMe$_2$ | F | F | H | H |
| B-26 | OCHMe$_2$ | F | H | F | H |
| B-27 | OCHMe$_2$ | F | H | H | F |
| B-28 | OCHMe$_2$ | F | Me | H | H |
| B-29 | OCHMe$_a$ | F | H | Me | H |
| B-30 | OCHMe$_2$ | F | H | H | Me |
| B-31 | OCHMe$_2$ | Me | F | H | H |
| B-32 | OCHMe$_2$ | Me | H | F | H |
| B-33 | OCHMe$_2$ | Me | H | H | F |
| B-34 | OCHMe$_2$ | Me | Me | H | H |
| B-35 | OCHMe$_2$ | Me | H | Me | H |
| B-36 | OCHMe$_2$ | Me | H | H | Me |
| B-37 | OCHF$_2$ | F | H | H | H |
| B-38 | OCHF$_2$ | Me | H | H | H |

TABLE 37

| No. | $R^{6A}$ | $R^{7A}$ | $R^{7B}$ | $R^{7C}$ | $R^{7D}$ |
|---|---|---|---|---|---|
| B-39 | OCHF$_2$ | H | F | H | H |
| B-40 | OCHF$_2$ | H | Me | H | H |
| B-41 | OCHP$_2$ | F | F | H | H |
| B-42 | OCHF$_2$ | F | H | F | H |
| B-43 | OCHF$_2$ | F | H | H | F |
| B-44 | OCHF$_2$ | F | Me | H | H |
| B-45 | OCHF$_2$ | F | H | Me | H |
| B-46 | OCHF$_2$ | F | H | H | Me |
| B-47 | OCHF$_2$ | Me | F | H | H |
| B-48 | OCHF$_2$ | Me | H | F | H |
| B-49 | OCHF$_2$ | Me | H | H | F |
| B-50 | OCHF$_2$ | Me | Me | H | H |
| B-51 | OCHF$_2$ | Me | H | Me | H |
| B-52 | OCHF$_2$ | Me | H | H | Me |
| B-53 | SCHMe$_2$ | F | H | H | H |
| B-54 | SCHMe$_2$ | Me | H | H | H |
| B-55 | SCHMe$_2$ | H | F | H | H |
| B-56 | SCHMe$_2$ | H | Me | H | H |
| B-57 | SCHMe$_2$ | F | F | H | H |
| B-58 | SCHMe$_2$ | F | H | F | H |
| B-59 | SCHMe$_2$ | F | H | H | F |
| B-60 | SCHMe$_2$ | F | Me | H | H |
| B-61 | SCHMe$_2$ | F | H | Me | H |
| B-62 | SCHMe$_2$ | F | H | H | Me |
| B-63 | SCHMe$_2$ | Me | F | H | H |
| B-64 | SCHMe$_2$ | Me | H | F | H |
| B-65 | SCHMe$_2$ | Me | H | H | F |
| B-66 | SCHMe$_2$ | Me | Me | H | H |
| B-67 | SCHMe$_2$ | Me | H | Me | H |
| B-68 | SCHMe$_2$ | Me | H | H | Me |

Compounds of the formula (IB) are shown below; (No. of the compound, part A, part B), (IB-2,A-2,B-2), (IB-3,A-3,B-2), (IB-4,A-4,B-2), (IB-5,A-5,B-2), (IB-6,A-6,B-2), (IB-7,A-7,B-2), (IB-8,A-8,B-2), (IB-9,A-9,B-2), (IB-10,A-10,B-2), (IB-11,A-11,B-2), (IB-12,A-12,B-2), (IB-13,A-13,B-2), (IB-14,A-14,B-2), (IB-15,A-15,B-2), (IB-16,A-16,B-2), (IB-17,A-17,B-2), (IB-18,A-18,B-2), (IB-19,A-19,B-2), (IB-20,A-20,B-2), (IB-21,A-21,B-2), (IB-22,A-22,B-2), (IB-23, A-23,B-2), (IB-24,A-24,B-2), (IB-25,A-25,B-2), (IB-26,A-26,B-2), (IB-27,A-27,B-2), (IB-28,A-28,B-2), (IB-29,A-29,B-2), (IB-30,A-30,B-2), (IB-31,A-31,B-2), (IB-32,A-32,B-2), (IB-33,A-33,B-2), (IB-34,A-34,B-2), (IB-35,A-35,B-2), (IB-36,A-36,B-2), (IB-37,A-37,B-2), (IB-38,A-38,B-2), (IB-39,A-39,B-2), (IB-40,A-40,B-2), (IB-41,A-41,B-2), (IB-42,A-42,B-2), (IB-43,A-43,B-2), (IB-44,A-44,B-2), (IB-45, A-45,B-2), (IB-46,A-46,B-2), (IB-47,A-47,B-2), (IB-48,A-48,B-2), (IB-49,A-49,B-2), (IB-50,A-50,B-2), (IB-51,A-51,B-2), (IB-52,A-52,B-2), (IB-53,A-53,B-2), (IB-54,A-54,B-2), (IB-55,A-55,B-2), (IB-56,A-56,B-2), (IB-57,A-57,B-2), (IB-58,A-58,B-2), (IB-59,A-59,B-2), (IB-60,A-60,B-2), (IB-61,A-61,B-2), (IB-62,A-62,B-2), (IB-63,A-63,B-2), (IB-64,A-64,B-2), (IB-65,A-65,B-2), (IB-66,A-66,B-2), (IB-67, A-67,B-2), (IB-68,A-68,B-2), (IB-69,A-69,B-2), (IB-70,A-70,B-2), (IB-71,A-71,B-2), (IB-72,A-72,B-2), (IB-73,A-73,B-2), (IB-74,A-74,B-2), (IB-75,A-75,B-2), (IB-76,A-76,B-2), (IB-77,A-77,B-2), (IB-78,A-78,B-2), (IB-79,A-79,B-2), (IB-80,A-80,B-2), (IB-81,A-81,B-2), (IB-82,A-82,B-2), (IB-83,A-83,B-2), (IB-84,A-84,B-2), (IB-85,A-85,B-2), (IB-86,A-86,B-2), (IB-87,A-87,B-2), (IB-88,A-88,B-2), (IB-89, A-89,B-2), (IB-90,A-90,B-2), (IB-91,A-91,B-2), (IB-92,A-92,B-2), (IB-93,A-93,B-2), (IB-94,A-94,B-2), (IB-95,A-95,B-2), (IB-96,A-96,B-2), (IB-97,A-97,B-2), (IB-98,A-98,B-2), (IB-99,A-99,B-2), (IB-100,A-100,B-2), (IB-101,A-101,B-2), (IB-102,A-102,B-2), (IB-103,A-103, B-2), (IB-104,A-104,B-2), (IB-105,A-105,B-2), (IB-106,A-106,B-2), (IB-107,A-107,B-2), (IB-108,A-108,B-2), (IB-109,A-109,B-2), (IB-110,A-110,B-2), (IB-111,A-111,B-2), (IB-112,A-112,B-2), (IB-113,A-113,B-2), (IB-114,A-114, B-2), (IB-115,A-115,B-2), (IB-116,A-116,B-2), (IB-117,A-117, B-2), (IB-118,A-118,B-2), (IB-119,A-119,B-2), (IB-120,A-120,B-2), (IB-121,A-121,B-2), (IB-122,A-122,B-2), (IB-123,A-123,B2), (IB-124,A-124,B-2), (IB-125, A-125,B-2), (IB-126, A-126,B-2), (IB-127,A-127,B-2), (IB-128,A-128,B-2), (IB-129,A-129,B-2), (IB-130,A-130,B-2), (IB-131,A-131,B-2), (IB-132,A-132,B-2), (IB-133,A-133,B-2), (IB-134,A-134,B-2), (IB-135,A-135,B-2), (IB-136,A-136, B-2), (IB-137,A-137,B-2), (IB-138,A-138,B-2), (IB-139,A-139,B-2), (IB-140,A-140,B-2), (IB-141,A-141,B-2), (IB-142,A-142,B-2), (IB-143,A-143,B-2), (IB-144,A-144, B-2), (IB-145,A-145,B-2), (IB-146,A-146,B-2), (IB-147,A-147, B-2), (IB-148,A-148,B-2), (IB-149,A-149,B-2), (IB-150,A-150,B-2), (IB-151,A-151,B-2), (IB-152, A-152,B-2), (IB-153,A-153,B-2), (IB-154,A-154,B-2), (IB-155,A-155,B-2), (IB-156,A-156,B-2), (IB-157,A-157,B-2), (IB-158,A-158, B-2), (IB-159,A-159,B-2), (IB-160,A-160,B-2), (IB-161,A-161,B-2), (IB-162,A-162,B-2), (IB-163,A-163,B-2), (IB-164,A-164,B-2), (IB-165,A-165,B-2), (IB-166,A-166,B-2), (IB-167,A-167,B-2), (IB-168,A-168,B-2), (IB-169,A-169, B-2), (IB-170,A-170,B-2), (IB-171,A-171, B-2), (IB-172,A-172,B-2), (IB-173,A-173,B-2), (IB-174,A-174,B-2), (IB-175,A-175,B-2), (IB-176,A-176,B-2), (IB-177,A-177,B-2), (IB-178,A-178,B-2), (IB-179, A-179,B-2), (IB-180,A-180, B-2), (IB-181,A-181,B-2), (IB-182,A-182,B-2), (IB-183,A-183,B-2), (IB-184,A-184,B-2), (IB-185,A-185,B-2), (IB-186,A-186,B-2), (IB-187,A-187,B-2), (IB-188,A-188,B-2), (IB-189,A-189,B-2), (IB-190,A-190,B-2), (IB-191,A-191, B-2), (IB-192,A-192,B-2), (IB-193,A-193,B-2), (IB-194,A-194,B-2), (IB-195,A-195,B-2), (IB-196,A-196,B-2), (IB-197,A-197,B-2), (IB-198,A-198, B-2), (IB-199,A-199,B-2), (IB-200,A-200,B-2), (IB-201,A-201,B-2), (IB-202,A-202, B-2), (IB-203,A-203,B-2), (IB-204,A-204,B-2), (IB-205,A-205,B-2), (IB-206, A-206,B-2), (IB-207,A-207,B-2), (IB-208,A-208,B-2), (IB-209,A-209,B-2), (IB-210,A-210,B-2), (IB-211,A-211,B-2), (IB-212,A-212,B-2), (IB-213,A-213, B-2), (IB-214,A-214,B-2), (IB-215,A-215,B-2), (IB-216,A-216,B-2), (IB-217,A-217,B-2), (IB-218,A-218,B-2), (IB-219,A-219,B-2), (IB-220,A-220,B-2), (IB-224,A-224 B-2), (IB-226,A-226,B-2), (IB-233,A-233,B-2), (IB-238,A-238, B-2), (IB-239,A-239, B-2), (IB-244,A-244,B-2), (IB-246,A-246,B-2), (IB-247,A-247,B-2), (IB-248,A-248,B-2), (IB-251,A-2,B-21), (IB-252,A-3,B-21), (IB-253,A-4,B-21), (IB-254,A-5, B-21), (IB-255,A-6,B-21), (IB-256,A-7,B-21), (IB-257,A-8,B-21), (IB-258,A-9,B-21), (IB-259,A-10,B-21), (IB-260,A-11,B-21), (IB-261,A-12,B-21), (IB-262,A-13, B-21), (IB-263,A-14,B-21), (IB-264,A-15,B-21), (IB-265,A-16,B-21), (IB-266,A-17,B-21), (IB-267,A-18,B-21), (IB-268,A-19,B-21), (IB-269,A-20,B-21), (IB-270, A-21,B-21), (IB-271,A-22,B-21), (IB-272,A-23,B-21), (IB-273,A-24,B-21), (IB-274,A-25,B-21), (IB-275,A-26,B-21), (IB-276,A-27,B-21), (IB-277,A-28,B-21), (I B-278,A-29,B-21), (IB-279,A-30,B-21), (IB-280,A-31,B-21), (IB-281,A-32,B-21), (IB-282,A-33,B-21), (IB-283,A-34,B-21), (IB-284,A-35,B-21), (IB-285,A-36,B-21), (IB-286,A-37,B-21), (IB-287,A-38,B-21), (IB-288,A-39,B-21), (IB-289,A-40, B-21), (IB-290,A-41,B-21), (IB-291,A-42,B-21), (IB-292,A-43,B-21), (IB-293,A-44,B-21), (IB-294,A-45,B-21), (IB-295,A-46,B-21), (IB-296,A-47,B-21), (IB-297, A-48,B-21), (IB-298,A-49,B-21), (IB-299,A-50,B-21), (IB-300,A-51,B-21), (IB-301,A-52,B-21), (IB-302,A-53,B-21), (IB-303,A-54,B-21), (IB-304,A-55,B-21), (IB-305,A-56,B-21), (IB-306,A-57,B-21), (IB-307,A-58,B-21), (IB-308,A-59,B-21), (IB-309,A-60,B-21), (IB-310,A-61,B-21), (IB-311,A-62,B-21), (IB-312,A-63,B-21), (IB-313,A-64,B-21), (IB-314,A-65,B-21), (IB-315,A-66,B-21), (IB-316,A-67, B-21), (IB-317,A-68,B-21), (IB-318,A-69,B-21), (IB-319,A-70,B-21), (IB-320,A-71,B-21), (IB-321,A-72,B-21), (IB-322,A-73,B-21), (IB-323,A-74,B-21), (IB-324, A-75,B-21), (IB-325,A-76,B-21), (IB-326,A-77,B-21), (IB-327,A-78,B-21), (IB-328,A-79,B-21), (IB-329,A-80,B-21), (IB-330,A-81,B-21), (IB-331,A-82,B-21), (IB-332,A-83,B-21), (IB-333,A-84,B-21), (IB-334,A-85,B-21), (IB-335,A-86,B-21), (IB-336,A-87,B-21), (IB-337,A-88,B-21), (IB-338,A-89,B-21), (IB-339,A-90,B-21), (IB-340,A-91,B-21), (IB-341,A-92,B-21), (IB-342,A-93,B-21), (IB-343,A-94, B-21), (IB-344,A-95,B-21), (IB-345,A-96,B-21), (IB-346,A-97,B-21), (IB-347,A-98,B-21), (IB-348,A-99,B-21), (IB-349,A-100,B-21), (IB-350,A-101,B-21), (IB-351,A-102,B-21), (IB-352,A-103,B-21), (IB-353,A-104,B-21), (IB-354,A-105,B-21), (IB-355,A-106,B-21), (IB-356,A-107,B-21), (IB-357,A-108,B-21), (IB-358,A-109,B-21), (IB-359,A-110,B-21), (IB-360,A-111,B-21), (IB-361,A-112,B-21), (IB-362,A-113,B-21), (IB-363,A-114,B-21), (IB-364,A-115,B-21), (IB-365,A-116,B-21), (IB-366,A-117,B-21), (IB-367,A-118,B-21), (IB-368,A-119,B-21), (IB-369,A-120,B-21), (IB-370,A-121,B-21), (IB-371,A-122,B-21), (IB-372,A-123,B-21), (IB-373,A-124,B-21), (IB-374,A-125,B-21), (IB-375,A-126,B-21), (IB-376,A-127, B-21), (IB-377,A-128,B-21), (IB-378,A-129,B-21), (IB-379,A-130,B-21), (IB-380, A-131,B-21), (IB-381,A-132,B-21), (IB-382,A-133,B-21), (IB-383,A-134, 13-21), (IB-384,A-135,B-21), (IB-385,A-136,B-21), (IB-386,A-137,B-21), (IB-387,A-138, B-21), (IB-388,A-139,B-21), (IB-389,A-140,B-21), (IB-390,A-141,B-21), (IB-391, A-142,B-21), (IB-392,A-143,B-21), (IB-393,A-144,B-21), (IB-394,A-145,B-21), (IB-395,A-146,B-21), (IB-396,A-147,B-21), (IB-397,A-148,B-21), (IB-398,A-149, B-21), (IB-399,A-150,B-21), (IB-400,A-151,B-21), (IB-401,A-152,B-21), (IB-402, A-153,B-21), (IB-403,A-154,B-21), (IB-404,A-155,B-21), (IB-405,A-

156,B-21), (IB-406,A-157,B-21), (IB-407,A-158,B-21), (IB-408,A-159,B-21), (IB-409,A-160, B-21), (IB-410,A-161,B-21), (IB-411,A-162,B-21), (IB-412,A-163,B-21), (IB-413, A-164,B-21), (IB-414,A-165,B-21), (IB-415,A-166,B-21), (IB-416,A-167,B-21), (IB-417,A-168,B-21), (IB-418,A-169,B-21), (IB-419,A-170,B-21), (IB-420,A-171, B-21), (IB-421,A-172,B-21), (IB-422,A-173,B-21), (IB-423,A-174,B-21), (IB-424, A-175,B-21), (IB-425,A-176,B-21), (IB-426,A-177,B-21), (IB-427,A-178,B-21), (IB-428,A-179,B-21), (IB-429,A-180,B-21), (IB-430,A-181,B-21), (IB-431,A-182, B-21), (IB-432,A-183,B-21), (IB-433,A-184,B-21), (IB-434,A-185,B-21), (IB-435, A-186,B-21), (IB-436,A-187,B-21), (IB-437,A-188,B-21), (IB-438,A-189,B-21), (IB-439,A-190,B-21), (IB-440,A-191,B-21), (IB-441,A-192,B-21), (IB-442,A-193, B-21), (IB-443,A-194,B-21), (IB-444,A-195,B-21), (IB-445,A-196,B-21), (IB-446, A-197,B-21), (IB-447,A-198,B-21), (IB-448,A-199,B-21), (IB-449,A-200,B-21), (IB-450,A-201,B-21), (IB-451,A-202,B-21), (IB-452,A-203,B-21), (IB-453,A-204, B-21), (IB-454,A-205,B-21), (IB-455,A-206,B-21), (IB-456,A-207,B-21), (IB-457, A-208,B-21), (IB-458,A-209,B-21), (IB-459,A-210,B-21), (IB-460,A-211,B-21), (IB-461,A-212,B-21), (IB-462,A-213,B-21), (IB-463,A-214,B-21), (IB-464,A-215, B-21), (IB-465,A-216,B-21), (IB-466,A-217,B-21), (IB-467,A-218,B-21), (IB-468, A-219,B-21), (IB-469,A-220,B-21), (IB-470,A-221,B-21), (IB-471,A-222,B-21), (IB-472,A-223,B-21), (IB-473,A-224,B-21), (IB-474,A-225,B-21), (IB-475,A-226, B-21), (IB-476,A-227,B-21), (IB-477,A-228,B-21), (IB-478,A-229,B-21), (IB-479, A-230,B-21), (IB-480,A-231,B-21), (IB-481,A-232,B-21), (IB-482,A-233,B-21), (IB-483,A-234,B-21), (IB-484,A-235,B-21), (IB-485,A-236,B-21), (IB-486,A-237, B-21), (IB-487,A-238,B-21), (IB-488,A-239,B-21), (IB-489,A-240,B-21), (IB-490, A-241,B-21), (IB-491,A-242,B-21), (IB-492,A-243,B-21), (IB-493,A-244,B-21), (IB-494,A-245,B-21), (IB-495,A-246,B-21), (IB-496,A-247,B-21), (IB-497,A-248, B-21), (IB-498,A-249,B-21), (IB-500,A-2,B-22), (IB-501,A-3,B-22), (IB-502,A-4, B-22), (IB-503,A-5,B-22), (IB-504,A-6,B-22), (IB-505,A-7,B-22), (IB-506,A-8,B-22), (IB-507,A-9, B-22), (IB-508,A-10,B-22), (IB-509,A-11,B-22), (IB-510, A-12, B-22), (IB-511,A-13,B-22), (IB-512,A-14,B-22), (IB-513,A-15,B-22), (IB-514,A-16,B-22), (IB-515,A-17,B-22), (IB-516,A-18,B-22), (IB-517,A-19,B-22), (IB-518, A-20,B-22), (IB-519,A-21,B-22), (IB-520,A-22,B-22), (IB-521,A-23,B-22), (IB-522,A-24,B-22), (IB-523,A-25,B-22), (IB-524,A-26,B-22), (IB-525,A-27,B-22), (IB-526,A-28,B-22), (IB-527,A-29,B-22), (IB-528,A-30,B-22), (IB-529,A-31,B-22), (IB-530,A-32,B-22), (IB-531,A-33,B-22), (IB-532,A-34,B-22), (IB-533,A-35,B-22), (IB-534,A-36,B-22), (IB-535,A-37,B-22), (IB-536,A-38,B-22), (IB-537,A-39, B-22), (IB-538,A-40,B-22), (IB-539,A-41,B-22), (IB-540,A-42,B-22), (IB-541,A-43,B-22), (IB-542,A-44,B-22), (IB-543,A-45,B-22), (IB-544,A-46,B-22), (IB-545, A-47,B-22), (IB-546,A-48,B-22), (IB-547,A-49,B-22), (IB-548,A-50,B-22), (IB-549,A-51,B-22), (IB-550,A-52,B-22), (IB-551,A-53,B-22), (IB-552,A-54,B-22), (IB-553,A-55,B-22), (IB-554,A-56,B-22), (IB-555, A-57,B-22), (IB-556,A-58,B-22), (IB-557,A-59,B-22), (IB-558,A-60,B-22), (IB-559,A-61,B-22), (IB-560,A-62,B-22), (IB-561,A-63,B-22), (IB-562,A-64,B-22), (IB-563,A-65,B-22), (IB-564,A-66, B-22), (IB-565,A-67,B-22), (IB-566,A-68,B-22), (IB-567,A-69,B-22), (IB-568,A-70,B-22), (IB-569,A-71,B-22), (IB-570,A-72,B-22), (IB-571,A-73,B-22), (IB-572, A-74,B-22), (IB-573,A-75,B-22), (IB-574,A-76,B-22), (IB-575,A-77,B-22), (IB-576,A-78, B-22), (IB-577,A-79,B-22), (IB-578,A-80,B-22), (IB-579, A-81,B-22), (IB-580,A-82,B-22), (IB-581,A-83,B-22), (IB-582,A-84,B-22), (IB-583,A-85,B-22), (IB-584,A-86,B-22), (IB-585,A-87,B-22), (IB-586,A-88,B-22), (IB-587,A-89,B-22), (IB-588,A-90,B-22), (IB-589,A-91,B-22), (IB-590,A-92,B-22), (IB-591,A-93, B-22), (IB-592,A-94,B-22), (IB-593,A-95,B-22), (IB-594,A-96,B-22), (IB-595,A-97,B-22), (IB-596,A-98,B-22), (IB-597,A-99,B-22), (IB-598,A-100, B-22), (IB-599,A-101,B-22), (IB-600,A-102,B-22), (IB-601,A-103,B-22), (IB-602,A-104,B-22), (IB-603,A-105,B-22), (IB-604,A-106,B-22), (IB-605,A-107,B-22), (IB-606, A-108, B-22), (IB-607,A-109,B-22), (IB-608,A-110,B-22), (IB-609,A-111,B-22), (IB-610, A-112,B-22), (IB-611,A-113,B-22), (IB-612,A-114,B-22), (IB-613,A-115,B-22), (IB-614,A-116,B-22), (IB-615,A-117,B-22), (IB-616,A-118,B-22), (IB-617,A-119, B-22), (IB-618,A-120,B-22), (IB-619,A-121,B-22), (IB-620,A-122,B-22), (IB-621, A-123,B-22), (IB-622,A-124,B-22), (IB-623,A-125,B-22), (IB-624,A-126,B-22), (IB-625,A-127,B-22), (IB-626,A-128,B-22), (IB-627,A-129,B-22), (IB-628,A-130, B-22), (IB-629,A-131,B-22), (IB-630,A-132,B-22), (IB-631,A-133,B-22), (IB-632, A-134,B-22), (IB-633,A-135,B-22), (IB-634,A-136,B-22), (IB-635,A-137,B-22), (IB-636,A-138,B-22), (IB-637,A-139,B-22), (IB-638,A-140,B-22), (IB-639,A-141, B-22), (IB-640,A-142,B-22), (IB-641,A-143,B-22), (IB-642,A-144,B-22), (IB-643, A-145,B-22), (IB-644,A-146,B-22), (IB-645,A-147,B-22), (IB-646,A-148,B-22), (IB-647,A-149,B-22), (IB-648,A-150,B-22), (IB-649,A-151,B-22), (IB-650,A-152, B-22), (IB-651,A-153,B-22), (IB-652,A-154,B-22), (IB-653,A-155,B-22), (IB-654, A-156,B-22), (IB-655,A-157,B-22), (IB-656,A-158,B-22), (IB-657,A-159,B-22), (IB-658,A-160,B-22), (IB-659,A-161,B-22), (IB-660,A-162,B-22), (IB-661,A-163, B-22), (IB-662,A-164,B-22), (IB-663,A-165,B-22), (IB-664,A-166,B-22), (IB-665, A-167,B-22), (IB-666,A-168,B-22), (IB-667,A-169,B-22), (IB-668,A-170,B-22), (IB-669,A-171,B-22), (IB-670,A-172,B-22), (IB-671,A-173,B-22), (IB-672,A-174, B-22), (IB-673,A-175,B-22), (IB-674,A-176,B-22), (IB-675,A-177,B-22), (IB-676, A-178,B-22), (IB-677,A-179,B-22), (IB-678,A-180,B-22), (IB-679,A-181,B-22), (IB-680,A-182,B-22), (IB-681,A-183,B-22), (IB-682,A-184,B-22), (IB-683,A-185, B-22), (IB-684,A-186,B-22), (IB-685,A-187,B-22), (IB-686,A-188,B-22), (IB-687, A-189,B-22), (IB-688,A-190,B-22), (IB-689,A-191,B-22), (IB-690,A-192,B-22), (IB-691,A-193,B-22), (IB-692,A-194,B-22), (IB-693,A-195,B-22), (IB-694,A-196, B-22), (IB-695,A-197,B-22), (IB-696,A-198,B-22), (IB-697,A-199,B-22), (IB-698, A-200,B-22), (IB-699,A-201,B-22), (IB-700,A-202,B-22), (IB-701,A-203,B-22), (IB-702,A-204,B-22), (IB-703,A-205,B-22), (IB-704,A-206,B-22), (IB-705,A-207, B-22), (IB-706,A-208,B-22), (IB-707,A-209,B-22), (IB-708,A-210,B-22), (IB-709, A-211,B-22), (IB-710,A-212,B-22), (IB-711,A-213,B-22), (IB-712,A-214,B-22), (IB-713,A-215,B-22), (IB-714,A-216,B-22), (IB-715,A-217,B-22), (IB-716,A-218, B-22), (IB-717,A-219,B-22), (IB-718,A-220,B-22), (IB-719,A-221,B-22), (IB-720, A-222,B-22), (IB-721,A-223,B-22), (IB-722,A-224,B-22), (IB-723,A-225,B-22), (IB-724,A-226,B-22), (IB-725,A-227,B-22), (IB-726,A-228,B-22), (IB-727,A-229, B-22), (IB-728,A-230,B-22), (IB-729,A-231,B-22), (IB-730,A-232,B-22), (IB-731, A-233,B-22), (IB-732,A-234,B-22), (IB-733,A-235,B-22), (IB-734,A-236,B-22), (IB-735,A-237,B-22), (IB-736,A-238,B-22), (IB-737,A-239,B-22), (IB-738,A-240, B-22), (IB-739,A-241,B-22), (IB-740,A-242,B-22), (IB-741,A-243,B-22), (IB-742, A-244,B-22), (IB-743,A-245,B-22), (IB-744,A-246, B-22), (IB-745,A-247,B-22), (IB-746,A-248,B-22), (IB-747,A-249,B-22), (IB-749,A-2,B-23), (IB-750,A-3,B-23), (IB-751,A-4,B-23), (IB-752,A-5,B-23), (IB-

753,A-6,B-23), (IB-754,A-7,B-23), (IB-755,A-8,B-23), (IB-756,A-9,B-23), (IB-757,A-10,B-23), (IB-758,A-11,B-23), (IB-759,A-12,B-23), (IB-760,A-13,B-23), (IB-761,A-14,B-23), (IB-762,A-15,B-23), (IB-763,A-16,B-23), (IB-764,A-17,B-23), (IB-765,A-18,B-23), (IB-766,A-19, B-23), (IB-767,A-20,B-23), (IB-768,A-21,B-23), (IB-769,A-22,B-23), (IB-770,A-23,B-23), (IB-771,A-24,B-23), (IB-772,A-25,B-23), (IB-773,A-26,B-23), (IB-774, A-27,B-23), (IB-775,A-28,B-23), (IB-776,A-29,B-23), (IB-777,A-30,B-23), (IB-778,A-31,B-23), (IB-779,A-32,B-23), (IB-780,A-33,B-23), (IB-781,A-34,B-23), (IB-782,A-35,B-23), (IB-783,A-36,B-23), (IB-784,A-37,B-23), (IB-785,A-38,B-23), (IB-786,A-39,B-23), (IB-787,A-40,B-23), (IB-788,A-41,B-23), (IB-789,A-42,B-23), (IB-790,A-43,B-23), (IB-791,A-44,B-23), (IB-792,A-45,B-23), (IB-793,A-46, B-23), (IB-794,A-47,B-23), (IB-795,A-48,B-23), (IB-796,A-49, B-23), (IB-797,A-50,B-23), (IB-798,A-51,B-23), (IB-799,A-52,B-23), (IB-800,A-53,B-23), (IB-801, A-54,B-23), (IB-802,A-55,B-23), (IB-803,A-56,B-23), (IB-804,A-57,B-23), (IB-805,A-58,B-23), (IB-806,A-59,B-23), (IB-807,A-60,B-23), (IB-808,A-61,B-23), (IB-809,A-62,B-23), (IB-810,A-63,B-23), (IB-811,A-64,B-23), (IB-812,A-65,B-23), (IB-813,A-66,B-23), (IB-814,A-67,B-23), (IB-815,A-68,B-23), (IB-816,A-69,B-23), (IB-817,A-70,B-23), (IB-818,A-71,B-23), (IB-819,A-72,B-23), (IB-820,A-73, B-23), (IB-821,A-74,B-23), (IB-822,A-75,B-23), (IB-823,A-76,B-23), (IB-824,A-77,B-23), (IB-825,A-78,B-23), (IB-826,A-79,B-23), (IB-827,A-80,B-23), (IB-828, A-81,B-23), (IB-829,A-82,B-23), (IB-830,A-83,B-23), (IB-831,A-84,B-23), (IB-832,A-85,B-23), (IB-833,A-86,B-23), (IB-834,A-87,B-23), (IB-835,A-88,B-23), (IB-836,A-89,B-23), (IB-837,A-90,B-23), (IB-838,A-91,B-23), (IB-839,A-92,B-23), (IB-840,A-93,B-23), (IB-841,A-94,B-23), (IB-842,A-95,B-23), (IB-843,A-96,B-23), (IB-844,A-97,B-23), (IB-845,A-98,B-23), (IB-846,A-99,B-23), (IB-847,A-100, B-23), (IB-848,A-101,B-23), (IB-849,A-102,B-23), (IB-850,A-103,B-23), (IB-851, A-104,B-23), (IB-852,A-105,B-23), (IB-853,A-106,B-23), (IB-854,A-107,B-23), (IB-855,A-108,B-23), (IB-856,A-109,B-23), (IB-857,A-110,B-23), (IB-858,A-111, B-23), (IB-859,A-112,B-23), (IB-860,A-113,B-23), (IB-861,A-114,B-23), (IB-862, A-115,B-23), (IB-863,A-116,B-23), (IB-864,A-117,B-23), (IB-865,A-118,B-23), (IB-866,A-119,B-23), (IB-867,A-120,B-23), (IB-868,A-121,B-23), (IB-869,A-122, B-23), (IB-870,A-123,B-23), (IB-871,A-124,B-23), (IB-872,A-125,B-23), (IB-873, A-126,B-23), (IB-874,A-127,B-23), (IB-875,A-128,B-23), (IB-876,A-129,B-23), (IB-877,A-130,B-23), (IB-878,A-131,B-23), (IB-879,A-132,B-23), (IB-880,A-133, B-23), (IB-881,A-134,B-23), (IB-882,A-135,B-23), (IB-883,A-136,B-23), (IB-884, A-137,B-23), (IB-885,A-138,B-23), (IB-886,A-139,B-23), (IB-887,A-140,B-23), (IB-888,A-141,B-23), (IB-889,A-142,B-23), (IB-890,A-143,B-23), (IB-891,A-144, B-23), (IB-892,A-145,B-23), (IB-893,A-146,B-23), (IB-894,A-147,B-23), (IB-895, A-148,B-23), (IB-896,A-149,B-23), (IB-897,A-150,B-23), (IB-898,A-151,B-23), (IB-899,A-152,B-23), (IB-900,A-153, B-23), (IB-901,A-154,B-23), (IB-902,A-155, B-23), (IB-903,A-156,B-23), (IB-904,A-157,B-23), (IB-905,A-158,B-23), (IB-906, A-159,B-23), (IB-907,A-160,B-23), (IB-908,A-161,B-23), (IB-909,A-162,B-23), (IB-910,A-163,B-23), (IB-911,A-164,B-23), (IB-912,A-165,B-23), (IB-913,A-166, B-23), (IB-914,A-167,B-23), (IB-915,A-168,B-23), (IB-916,A-169,B-23), (IB-917, A-170,B-23), (IB-918,A-171,B-23), (IB-919,A-172,B-23), (IB-920,A-173,B-23), (IB-921,A-174,B-23), (IB-922,A-175,B-23), (IB-923,A-176,B-23), (IB-924,A-177, B-23), (IB-925,A-178,B-23), (IB-926,A-179,B-23), (IB-927,A-180,B-23), (IB-928, A-181,B-23), (IB-929,A-182,B-23), (IB-930,A-183,B-23), (IB-931,A-184,B-23), (IB-932,A-185,B-23), (IB-933,A-186,B-23), (IB-934,A-187,B-23), (IB-935,A-188, B-23), (IB-936,A-189,B-23), (IB-937,A-190,B-23), (IB-938,A-191,B-23), (IB-939, A-192,B-23), (IB-940,A-193,B-23), (IB-941,A-194,B-23), (IB-942,A-195,B-23), (IB-943,A-196,B-23), (IB-944,A-197,B-23), (IB-945,A-198,B-23), (IB-946,A-199; B-23), (IB-947,A-200,B-23), (IB-948,A-201,B-23), (IB-949,A-202,B-23), (IB-950, A-203,B-23), (IB-951,A-204,B-23), (IB-952,A-25,B-23), (IB-953,A-206,B-23), (IB-954,A-207, B-23), (IB-955,A-208,B-23), (IB-956,A-209,B-23), (IB-957,A-210, B-23), (IB-958,A-211,B-23), (IB-959,A-212,B-23), (IB-960,A-213,B-23), (IB-961, A-214,B-23), (IB-962, A-215,B-23), (IB-963,A-216,B-23), (IB-964,A-217,B-23), (IB-965,A-218,B-23), (IB-966,A-219,B-23), (IB-967,A-220,B-23), (IB-968,A-221, B-23), (IB-969,A-222,B-23), (IB-970,A-223,B-23), (IB-971,A-224,B-23), (IB-972, A-225,B-23), (IB-973,A-226,B-23), (IB-974,A-227,B-23), (IB-975,A-228,B-23), (IB-976,A-229,B-23), (IB-977,A-230,B-23), (IB-978,A-231,B-23), (IB-979,A-232, B-23), (IB-980,A-233,B-23), (IB-981,A-234,B-23), (IB-982,A-235,B-23), (IB-983, A-236,B-23), (IB-984,A-237,B-23), (IB-985,A-238,B-23), (IB-986,A-239,B-23), (IB-987,A-240,B-23), (IB-988,A-241,B-23), (IB-989,A-242,B-23), (IB-990,A-243, B-23), (IB-991,A-244,B-23), (IB-992,A-245,B-23), (IB-993,A-246,B-23), (IB-994, A-247,B-23), (IB-995,A-248,B-23), (IB-996,A-249,B-23), (IB-998,A-2, B-24), (IB-999,A-3,B-24), (IB-1000,A-4,B-24), (IB-1001, A-5,B-24), (IB-1002,A-6,B-24), (IB-1003,A-7,B-24), (IB-1004,A-8,B-24), (IB-1005,A-9,B-24), (IB-1006,A-10,B-24), (IB-1007,A-11,B-24), (IB-1008,A-12,B-24), (IB-1009, A-13,B-24), (IB-1010,A-14,B-24), (IB-1011,A-15,B-24), (IB-1012,A-16,B-24), (IB-1013,A-17,B-24), (IB-1014,A-18,B-24), (IB-1015,A-19,B-24), (IB-1016,A-20,B-24), (IB-1017,A-21,B-24), (IB-1018,A-22,B-24), (IB-1019,A-23,B-24), (IB-1020,A-24,B-24), (IB-1021, A-25,B-24), (IB-1022, A-26,B-24), (IB-1023,A-27,B-24), (IB-1024,A-28,B-24), (IB-1025,A-29,B-24), (IB-1026,A-30,B-24), (IB-1027,A-31,B-24), (IB-1028,A-32, B-24), (IB-1029,A-33,B-24), (IB-1030,A-34,B-24), (IB-1031,A-35,B-24), (IB-1032,A-36,B-24), (IB-1033,A-37,B-24), (IB-1034,A-38,B-24), (IB-1035, A-39,B-24), (IB-1036,A-40,B-24), (IB-1037,A-41,B-24), (IB-1038,A-42,B-24), (IB-1039,A-43, B-24), (IB-1040,A-44,B-24), (IB-1041,A-45,B-24), (IB-1042,A-46,B-24), (IB-1043,A-47,B-24), (IB-1044,A-48,B-24), (IB-1045,A-49,B-24), (IB-1046,A-50,B-24), (IB-1047,A-51,B-24), (IB-1048, A-52,B-24), (IB-1049,A-53,B-24), (IB-1050,A-54, B-24), (IB-1051,A-55,B-24), (IB-1052,A-56,B-24), (IB-1053,A-57,B-24), (IB-1054,A-58,B-24), (IB-1055,A-59,B-24), (IB-1056,A-60,B-24), (IB-1057,A-61,B-24), (IB-1058,A-62,B-24), (IB-1059,A-63,B-24), (IB-1060,A-64,B-24), (IB-1061, A-65, B-24), (IB-1062,A-66,B-24), (IB-1063,A-67,B-24), (IB-1064,A-68,B-24), (IB-1065,A-69,B-24), (IB-1066,A-70,B-24), (IB-1067,A-71,B-24), (IB-1068,A-72,B-24), (IB-1069,A-73,B-24), (IB-1070,A-74,B-24), (IB-1071,A-75,B-24), (IB-1072,A-76, B-24), (IB-1073,A-77,B-24), (IB-1074, A-78,B-24), (IB-1075,A-79,B-24), (IB-1076,A-80,B-24), (IB-1077,A-81,B-24), (IB-1078,A-82,B-24), (IB-1079,A-83,B-24), (IB-1080,A-84,B-24), (IB-1081,A-85,B-24), (IB-1082,A-86,B-24), (IB-1083,A-87, B-24), (IB-1084,A-88,B-24), (IB-1085,A-89,B-24), (IB-1086,A-90,B-24), (IB-1087, A-91,B-24), (IB-1088,A-92,B-24), (IB-1089,A-93,B-24), (IB-1090,A-94,B-24), (IB-1091,A-95,B-24), (IB-1092,A-96,B-24), (IB-1093,A-97,B-24), (IB-1094,A-98, B-24), (IB-1095,A-99,B-24), (IB-1096,A-100,B-24), (IB-1097,A-101, B-24), (IB-1098,A-102,B-24), (IB-1099,A-103,B-24), (IB-100,A-104,B-24), (IB-1101,A-105, B-24), (IB-1102,A-106,

B-24), (IB-1103,A-107,B-24), (IB-1104,A-108,B-24), (IB-1105,A-109,B-24), (IB-1106,A-110,B-24), (IB-1107,A-111,B-24), (IB-1108,A-112,B-24), (IB-1109,A-113,B-24), (IB-1110,A-114,B-24), (IB-1111,A-115,B-24), (IB-1112,A-116,B-24), (IB-1113,A-117,B-24), (IB-1114,A-118,B-24), (IB-1115,A-119,B-24), (IB-1116,A-120,B-24), (IB-1117,A-121,B-24), (IB-1118,A-122,B-24), (IB-1119,A-123,B-24), (IB-1120,A-124,B-24), (IB-1121,A-125,B-24), (IB-1122,A-126,B-24), (IB-1123,A-127,B-24), (IB-1124,A-128,B-24), (IB-1125,A-129,B-24), (IB-1126,A-130,B-24), (IB-1127,A-131,B-24), (IB-1128,A-132,B-24), (IB-1129,A-133,B-24), (IB-1130,A-134,B-24), (IB-1131,A-135,B-24), (IB-1132,A-136,B-24), (IB-1133,A-137,B-24), (IB-1134,A-138,B-24), (IB-1135,A-139,B-24), (IB-1136,A-140,B-24), (IB-1137,A-141,B-24), (IB-1138,A-142,B-24), (IB-1139,A-143,B-24), (IB-1140,A-144,B-24), (IB-1141,A-145,B-24), (IB-1142,A-146,B-24), (IB-1143,A-147,B-24), (IB-1144,A-148,B-24), (IB-1145,A-149,B-24), (IB-1146,A-150,B-24), (IB-1147,A-151,B-24), (IB-1148,A-152,B-24), (IB-1149,A-153,B-24), (IB-1150,A-154,B-24), (IB-1151,A-155,B-24), (IB-1152,A-156,B-24), (IB-1153,A-157,B-24), (IB-1154,A-158,B-24), (IB-1155,A-159,B-24), (IB-1156,A-160,B-24), (IB-1157,A-161,B-24), (IB-1158,A-162,B-24), (IB-1159,A-163,B-24), (IB-1160,A-164,B-24), (IB-1161,A-165,B-24), (IB-1162,A-166,B-24), (IB-1163,A-167,B-24), (IB-1164,A-168,B-24), (IB-1165,A-169,B-24), (IB-1166,A-170,B-24), (IB-1167,A-171,B-24), (IB-1168,A-172,B-24), (IB-1169,A-173,B-24), (IB-1170,A-174,B-24), (IB-1171,A-175,B-24), (IB-1172,A-176,B-24), (IB-1173,A-177,B-24), (IB-1174,A-178,B-24), (IB-1175,A-179,B-24), (IB-1176,A-180,B-24), (IB-1177,A-181, B-24), (IB-1178,A-182,B-24), (IB-1179,A-183,B-24), (IB-1180,A-184,B-24), (IB-1181,A-185,B-24), (IB-1182,A-186,B-24), (IB-1183,A-187,B-24), (IB-1184,A-188,B-24), (IB-1185,A-189,B-24), (IB-1186,A-190,B-24), (IB-1187,A-191,B-24), (IB-1188,A-192,B-24), (IB-1189,A-193,B-24), (IB-1190,A-194,B-24), (IB-1191,A-195,B-24), (IB-1192,A-196,B-24), (IB-1193,A-197,B-24), (IB-1194,A-198,B-24), (IB-1195,A-199,B-24), (IB-1196,A-200,B-24), (IB-1197,A-201,B-24), (IB-1198,A-202,B-24), (IB-1199,A-203,B-24), (IB-1200,A-204,B-24), (IB-1201,A-205,B-24), (IB-1202,A-206,B-24), (IB-1203,A-207,B-24), (IB-1204,A-208,B-24), (IB-1205,A-209,B-24), (IB-1206,A-210,B-24), (IB-1207,A-211,B-24), (IB-1208,A-212,B-24), (IB-1209,A-213,B-24), (IB-1210,A-214,B-24), (IB-1211,A-215,B-24), (IB-1212,A-216,B-24), (IB-1213,A-217,B-24), (IB-1214,A-218,B-24), (IB-1215,A-219, B-24), (IB-1216,A-220,B-24), (IB-1217,A-221,B-24), (IB-1218,A-222,B-24), (IB-1219,A-223,B-24), (IB-1220,A-224,B-24), (IB-1221,A-225,B-24), (IB-1222,A-226,B-24), (IB-1223,A-227,B-24), (IB-1224,A-228,B-24), (IB-1225,A-229,B-24), (I B-1226,A-230,B-24), (IB-1227,A-231,B-24), (IB-1228,A-232,B-24), (IB-1229,A-233,B-24), (IB-1230,A-234,B-24), (IB-1231,A-235,B-24), (IB-1232,A-236,B-24), (IB-1233,A-237,B-24), (IB-1234,A-238,B-24), (IB-1235,A-239,B-24), (IB-1236, A-240;B-24), (IB-1237,A-241,B-24), (IB-1238,A-242,B-24), (IB-1239,A-243,B-24), (IB-1240,A-244,B-24), (IB-1241,A-245,B-24), (IB-1242,A-246,B-24), (IB-1243,A-247,B-24), (IB-1244,A-248,B-24), (IB-1245,A-249,B-24), (IB-1249,A-1,B-5), (IB-1250,A-1,B-6), (IB-1251,A-1,B-7), (IB-1252,A-1,B-8), (IB-1253,A-1,B-25), (IB-1254,A-1,B-26), (IB-1255,A-1,B-27), (IB-1256,A-1,B-28), (IB-1257,A-1,B-29), (IB-1258,A-1,B-30), (IB-1259,A-1,B-31), (IB-1260,A-1,B-32), (IB-1261,A-1, B-33), (IB-1262,A-1,B-34), (IB-1263,A-1,B-35), (IB-1264,A-1,B-36), (IB-1265,A-1,B-37), (IB-1266,A-1,B-38), (IB-1267,A-1,B-39), (IB-1268,A-1,B-40), (IB-1269, A-1,B-53), (IB-1270,A-1,B-54), (IB-1271,A-1,B-55), (IB-1272,A-1,B-56), (IB-1273, A-222,B-1), (IB-1274,A-222,B-3), (IB-1275,A-222,B-4), (IB-1276,A-222,B-5), (IB-1277,A-222,B-6), (IB-1278,A-222,B-7), (IB-1279,A-222,B-8), (IB-1280,A-222,B-25), (IB-1281,A-222,B-26), (IB-1282,A-222,B-27), (IB-1283,A-222,B-28), (IB-1284,A-222,B-29), (IB-1285,A-222,B-30), (IB-1286,A-222,B-31), (IB-1287,A-222,B-32), (IB-1288,A-222,B-33), (IB-1289,A-222,B-34), (IB-1290,A-222,B-35), (IB-1291,A-222,B-36), (IB-1292,A-222,B-37), (IB-1293,A-222,B-38), (IB-1294, A-222,B-39), (IB-1295,A-222,B-40), (IB-1296,A-222,B-53), (IB-1297,A-222,B-54), (IB-1298,A-222,B-55), (IB-1299,A-222,B-56), (IB-1300,A-225,B-1), (IB-1301, A-225,B-3), (IB-1302,A-225,B-4), (IB-1303,A-225,B-5), (IB-1304,A-225,B-6), (IB-1305,A-225,B-7), (IB-1306,A-225,B-8), (IB-1307,A-225,B-25), (IB-1308,A-225,B-26), (IB-1309,A-225,B-27), (IB-1310,A-225,B-28), (IB-1311,A-225,B-29), (IB-1312,A-225,B-30), (IB-1313,A-225,B-31), (IB-1314,A-225,B-32), (IB-1315,A-225,B-33), (IB-1316,A-225,B-34), (IB-1317,A-225,B-35), (IB-1318,A-225,B-36), (IB-1319,A-225,B-37), (IB-1320,A-225,B-38), (IB-1321,A-225,B-39), (IB-1322, A-225,B-40), (IB-1323,A-225,B-53), (IB-1324,A-225,B-54), (IB-1325,A-225,B-55), (IB-1326,A-225,B-56), (IB-1327,A-240,B-1), (IB-1328,A-240,B-3), (IB-1329, A-240, B-4), (IB-1330,A-240,B-5), (IB-1331,A-240,B-6), (IB-1332,A-240,B-7), (IB-1333,A-240,B-8), (IB-1334,A-240,B-25), (IB-1335,A-240,B-26), (IB-1336,A-240,B-27), (IB-1337,A-240,B-28), (IB-1338,A-240,B-29), (IB-1339,A-240, B-30), (IB-1340,A-240,B-31), (IB-1341,A-240,B-32), (IB-1342,A-240,B-33), (IB-1343, A-240,B-34), (IB-1344,A-240,B-35), (IB-1345,A-240,B-36), (IB-1346,A-240,B-37), (IB-1347,A-240,B-38), (IB-1348,A-240,B-39), (IB-1349,A-240,B-40), (IB-1350,A-240,B-53), (IB-1351,A-240,B-54), (IB-1352,A-240,B-55), (IB-1353,A-240,B-56), (IB-1354,A-241,B-1), (IB-1355,A-241,B-3), (IB-1356,A-241,B-4), (IB-1357, A-241,B-5), (IB-1358,A-241,B-6), (IB-1359,A-241, B-7), (IB-1360,A-241,B-8), (IB-1361,A-241,B-25), (IB-1362,A-241,B-26), (IB-1363,A-241,B-27), (IB-1364,A-241,B-28), (IB-1365,A-241,B-29), (IB-1366,A-241,B-30), (IB-1367,A-241,B-31), (IB-1368,A-241,B-32), (IB-1369,A-241,B-33), (IB-1370,A-241,B-34), (IB-1371, A-241,B-35), (IB-1372,A-241,B-36), (IB-1373,A-241,B-37), (IB-1374,A-241,B-38), (IB-1375,A-241,B-39), (IB-1376,A-241,B-40), (IB-1377,A-241,B-53), (IB-1378,A-241,B-54), (IB-1379,A-241,B-55), (IB-1380,A-241,B-56), (IB-1381,A-245,B-1), (IB-1382,A-245,B-3), (IB-1383,A-245,B-4), (IB-1384,A-245,B-5), (IB-1385, A-245,B-6), (IB-1386,A-245,B-7), (IB-1387, A-245,B-8), (IB-1388,A-245,B-25), (IB-1389,A-245,B-26), (IB-1390,A-245,B-27), (IB-1391,A-245,B-28), (IB-1392, A-245,B-29), (IB-1393,A-245,B-30), (IB-1394,A-245,B-31), (IB-1395,A-245,B-32), (IB-1396,A-245,B-33), (IB-1397,A-245,B-34), (IB-1398,A-245,B-35), (IB-1399,A-245, B-36), (IB-1400,A-245,B-37), (IB-1401,A-245,B-38), (IB-1402,A-245,B-39), (IB-1403,A-245,B-40), (IB-1404,A-245,B-53), (IB-1405,A-245,B-54), (IB-1406,A-245,B-55), (IB-1407,A-245,B-56), (IB-1408,A-250,B-2), (IB-1409,A-250, B-21), (IB-1410,A-250,B-22), (IB-1411,A-250,B-23), (IB-1412,A-250,B-24), (IB-1414,A-251,B-21), (IB-1415,A-251, B-22), (IB-1416,A-251,B-23), (IB-1417,A-251,B-24), (IB-1419,A-252,B-21), (IB-1420,A-252,B-22), (IB-1421,A-252, B-23), (IB-1422,A-252,B-24), (IB-1424,A-253,B-21), (IB-1425,A-253,B-22), (IB-1426,A-253,B-23), (IB-1427,A-253, B-24), (IB-1428, A-254,B-2), (IB-1429,A-254,B-21), (IB-1430,A-254,B-22), (IB-1431,A-254,B-23), (IB-1432,A-254, B-24), (IB-1433, A-255,B-2), (IB-1434, A-255,B-21), (IB-1435,A-255,B-22), (IB-1436,A-255,B-23), (IB-1437,A-255, B-24), (IB-1438,A-256,B-2), (IB-1439,A-256,B-21), (IB-1440, A-256,B-22), (IB-1441, A-256,B-23), (IB-1442,A-256,B-24), (IB-1443,A-257,B-2), (IB-1444,A-257,B-21), (IB-1445,A-257,B-22), (IB-1446,A-257,B-23), (IB-1447,A-257,B-24), (IB-1448,A-258,B-2), (IB-1449,A-258,B-21), (IB-1450,A-258,B-22), (IB-1451,A-258,B-23), (IB-1452,A-258,B-24), (IB-1453,A-259,B-2), (IB-1454,A-260,B-2), (IB-1455,A-261,B-2), (IB-1456,A-262,B-2), (IB-1457,A-263,B-2), (IB-1458,A-264,B-2), (IB-1459,A-265,B-2), (IB-1460,A-266,B-2), (IB-1461,A-267,B-2), (IB-1462,A-268,B-2), (IB-1463,A-269,B-2), (IB-1464,A-270,B-2), (IB-1465,A-271,B-2), (IB-1466,A-272,B-2), (IB-1467,A-273,B-2), (IB-1468,A-274,B-2), (IB-1469,A-275,B-2), (IB-1470,A-276,B-2), (IB-1471,A-277,B-2), (IB-1472,A-278,B-2), (IB-1473,A-279,B-2), (IB-1474,A-280,B-2), (IB-1475,A-281,B-2), (IB-1476,A-282,B-2), (IB-1477,A-283,B-2), (IB-1478,A-284,B-2), (IB-1479,A-285,B-2), (IB-1480,A-286,B-2), (IB-1481,A-287,B-2), (IB-1482,A-288,B-2)

Moreover, compounds of the next formula (IC):

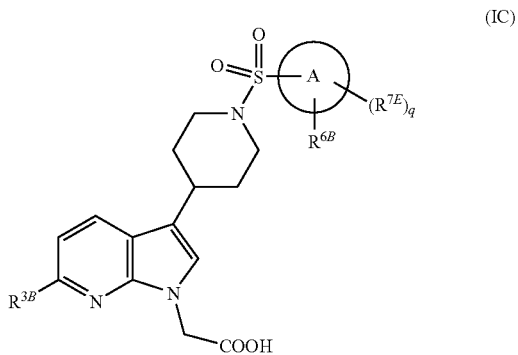

wherein the ring A is 3-pyridyl, 2-furyl, 2-thienyl, 2-oxazolyl, 2-thiazolyl, 2-benzoxazolyl, or 2-benzothiazolyl;

$R^{3B}$ is a hydrogen atom, a bromine atom, methyloxy, ethyloxy, methylamino, 2-thiazolyl, a chlorine atom, methyl, amino, acetylamino, acetyl, N-methylcarbamoyl, phenyl, 4-fluorophenyl, 2-pyridyl, 3-pyridyl, 2-oxazolyl, pyrrolidino, t-butyloxycarbonylamino, 2-furyl, 3-furyl, 2-thienyl, 3-thienyl, 5-oxazolyl, a fluorine atom, phenoxy, cyano, nitro, carbamoyl, N-n-propylcarbamoyl, N-phenylcarbamoyl, methyloxycarbonylamino, i-propyloxycarbonylamino, 3-pyridylcarbonylamino, 2-furylcarbonylamino, 3-methyloxyphenyl, 4-methyloxyphenyl, 4-cyanophenyl, 4-oxazolyl, 5-methyl-2-oxazolyl, 3,4-oxadiazol-2-yl, 5-methyl-3,4-oxadiazol-2-yl, 3,4-thiadiazol-2-yl, 5-methyl-3,4-thiadiazol-2-yl, 4-pyridyl, 4-methyloxy-3-pyridyl, hydrazinocarbonyl, 3,4-methylenedioxyphenyl, N-cyclopropylcarbamoyl, 4-isooxazolylcarbonylamino, 5-methyl-4-isooxazolylacrbonylamino, trifluoromethyl, or 3-methyloxypropargyl;

$R^{6B}$ is a hydrogen atom or isopropoxy;

$R^{7E}$ is independently a fluorine atom, a chlorine atom or methyl;

q is 0 or 1;

can be synthesized in the same manner as set forth above.

Compounds of the formula (IC) are shown below; (No. of the compound, $R^{3B}$, $A(R^{6B})(R^{7e})_q$), (IC-1,H,4-F-6-isopropyloxy-3-pyridyl), (IC-2,H, 2-furyl), (IC-3,H,5-Me-2-furyl), (IC-4,H,2-thienyl), (IC-5,H,5-Me-2-thienyl), (IC-6,H,2-oxazolyl), (IC-7,H, 5-methyl-2-oxazolyl), (IC-8,H,4-F-2-oxazolyl), (IC-9,H,4-isopropyloxy-2-oxazolyl), (IC-10,H,5-methyl-2-thiazolyl), (IC-11,H,4-F-2-thiazolyl), (IC-12,H,4-isopropyloxy-2-thiazolyl), (IC-13,H,5-F-2-benzoxazolyl), (IC-14,H,5-Cl-2-benzoxazolyl), (IC-15,H,5-Me-2-benzoxazolyl), (IC-16,H,5-isopropyloxy-2-benzoxazolyl), (IC-17, H,5-F-2-benzothiazolyl), (IC-18,H,5-Cl-2-benzothiazolyl), (IC-19,H,5-Me-2-benzothiazolyl), (IC-20,H,5-isopropyloxy-2-benzothiazolyl), (IC-21,Br,6-isopropyloxy-3-pyridyl), (IC-22,Br,4-F-6-isopropyloxy-3-pyridyl), (IC-23,Br, 2-furyl), (IC-24,Br,5-Me-2-furyl), (IC-25,Br,2-thienyl), (IC-26,Br,5-Me-2-thienyl), (IC-27,Br,2-oxazolyl), (IC-28,Br,5-methyl-2-oxazolyl), (IC-29,Br,4-F-2-oxazolyl), (IC-30,Br,4-isopropyloxy-2-oxazolyl), (IC-31,Br,5-methyl-2-thiazolyl), (IC-32,Br,4-F-2-thiazolyl), (IC-33,Br,4-isopropyloxy-2-thiazolyl), (IC-34,Br,5-F-2-benzoxazolyl), (IC-35,Br,5-Cl-2-benzoxazolyl), (IC-36,Br,5-Me-2-benzoxazolyl), (IC-37, Br,5-isopropyloxy-2-benzoxazolyl), (IC-38,Br,5-F-2-benzothiazolyl), (IC-39,Br,5-Cl-2-benzothiazolyl), (IC-40, Br,5-Me-2-benzothiazolyl), (IC-41,Br,5-isopropyloxy-2-benzothiazolyl), (IC-42,OMe,6-isopropyloxy-3-pyridyl), (IC-43,OMe,4-F-6-isopropyloxy-3-pyridyl), (IC-44,OMe,2-furyl), (IC-45,O Me,5-Me-2-furyl), (IC-46,OMe,2-thienyl), (IC-47,OMe,5-Me-2-thienyl), (IC-48, OMe,2-oxazolyl), (IC-49,OMe,5-methyl-2-oxazolyl), (IC-50,OMe,4-F-2-oxazolyl), (IC-51,OMe,4-isopropyloxy-2-oxazolyl), (IC-52, OMe,5-methyl-2-thiazolyl), (IC-53,OMe,4-F-2-thiazolyl), (IC-54,OMe,4-isopropyloxy-2-thiazolyl), (IC-55,OMe,5-F-2-benzoxazolyl), (IC-56,OMe,5-Cl-2-benzoxazolyl), (IC-57,OMe,5-Me-2-benzoxazolyl), (IC-58,OMe,5-isopropyloxy-2-benzoxazolyl), (IC-59,OMe,5-F-2-benzothiazolyl), (IC-60,OMe,5-Cl-2-benzothiazolyl), (IC-61,OMe,5-Me-2-benzothiazolyl), (IC-62,OMe,5-isopropyloxy-2-benzothiazolyl), (IC-63,OEt,6-isopropyloxy-3-pyridyl), (IC-64,OEt,4-F-6-isopropyloxy-3-pyridyl), (IC-65,OEt,2-furyl), (IC-66, OEt,5-Me-2-furyl), (IC-67,OEt,2-thienyl), (IC-68,OEt,5-Me-2-thienyl), (IC-69,OEt,2-oxazolyl), (IC-70,OEt,5-methyl-2-oxazolyl), (IC-71,OEt,4-F-2-oxazolyl), (IC-72, OEt,4-isopropyloxy-2-oxazolyl), (IC-73,OEt,5-methyl-2-thiazolyl), (IC-74,OEt,4-F-2-thiazolyl), (IC-75,OEt,4-isopropyloxy-2-thiazolyl), (IC-76,OEt,5-F-2-benzoxazolyl), (IC-77,OEt,5-Cl-2-benzoxazolyl), (IC-78,OEt,5-Me-2-benzoxazolyl), (IC-79,OEt,5-isopropyloxy-2-benzoxazolyl), (IC-80,OEt,5-F-2-benzothiazolyl), (IC-81,OEt,5-Cl-2-benzothiazolyl), (IC-82,OEt,5-Me-2-benzothiazolyl), (IC-83, OEt,5-isopropyloxy-2-benzothiazolyl), (IC-84,NHMe,6-iisopropyloxy-3-pyridyl), (IC-85,NHMe,4-F-6-isopropyloxy-3-pyridyl), (IC-86,NHMe,2-furyl), (IC-87, NHMe,5-Me-2-furyl), (IC-88,NHMe,2-thienyl), (IC-89, NHMe,5-Me-2-thienyl), (IC-90,NHMe,2-oxazolyl), (IC-91, NHMe,5-methyl-2-oxazolyl), (IC-92,NHMe, 4-F-2-oxazolyl), (IC-93,NHMe,4-isopropyloxy-2-oxazolyl), (IC-94,NHMe,5-methyl-2-thiazolyl), (IC-95,NHMe,4-F-2-thiazolyl), (IC-96,NHMe,4-isopropyloxy-2-thiazolyl), (IC-97,NHMe,5-F-2-benzoxazolyl), (IC-98,NHMe,5-Cl-2-benzoxazolyl), (IC-99,NHMe,5-Me-2-benzoxazolyl), (IC-100,NHMe,5-isopropyloxy-2-benzoxazolyl), (IC-101, NHMe,5-F-2-benzothiazolyl), (IC-102,NHMe,5-Cl-2-benzothiazolyl), (IC-103,NHMe,5-Me-2-benzothiazolyl), (IC-104,NHMe,5-isopropyloxy-2-benzothiazolyl), (IC-105, 2-thiazolyl,6-isopropyloxy-3-pyridyl), (IC-106,2-thiazolyl, 74-F-6-isopropyloxy-3-pyridyl), (IC-107,2-thiazolyl,2-furyl), (IC-108,2-thiazolyl,5-Me-2-furyl), (IC-109,2-thiazolyl, 2-thienyl), (IC-110,2-thiazolyl,5-Me-2-thienyl), (IC-111,2-thiazolyl,2-oxazolyl), (IC-112,2-thiazolyl,5-methyl-2-oxazolyl), (IC-113,2-thiazolyl,4-F-2-oxazolyl), (IC-114,2-thiazolyl,4-isopropyloxy-2-oxazolyl), (IC-115,2-thiazolyl, 5-methyl-2-thiazolyl), (IC-116,2-thiazolyl,4-F-2-thiazolyl), (IC-117,2-thiazolyl,4-isopropyloxy-2-thiazolyl), (IC-118,2-thiazolyl,5-F-2-benzoxazolyl), (IC-119,2-thiazolyl,5-Cl-2-benzoxazolyl), (IC-120,2-thiazolyl,5-Me-2-benzoxazolyl), (IC-121,2-thiazolyl,5-isopropyloxy-2-benzoxazolyl), (IC-122,2-thiazolyl,5-F-2-benzothiazolyl), (IC-123,2-thiazolyl, 5-Cl-2-benzothiazolyl), (IC-124,2-thiazolyl,5-Me-2-benzothiazolyl), (IC-125,2-thiazolyl,5-isopropyloxy-2-benzothiazolyl), (IC-126,Cl,6-isopropyloxy-3-pyridyl), (IC-127,Me,6-isopropyloxy-3-pyridyl), (IC-128,NH2,6-isopropyloxy-3-pyridyl), (IC-129,NHAc,6-isopropyloxy-3-pyridyl), (IC-130,Ac,6-isopropyloxy-3-pyridyl), (IC-131,CONHMe,6-isopropyloxy-3-pyridyl), (IC-132,Ph,6-isopropyloxy-3-pyridyl), (IC-133,4-F-phenyl,6-isopropyloxy-3-pyridyl), (IC-134,2-pyridyl,6-isopropyloxy-3-pyridyl), (I C-135,3-pyridyl,6-isopropyloxy-3-pyridyl), (IC-136,2-oxazolyl,6-isopropyloxy-3-pyridyl), (IC-137,pyrrolidino,6-isopropyloxy-3-pyridyl), (IC-138,NHBoc,6-isopropyloxy-3-pyridyl), (IC-139,2-furyl,6-isopropyloxy-3-pyridyl), (IC-140,3-furyl,6-isopropyloxy-3-pyridyl), (IC-141,2-thienyl,6-isopropyloxy-3-pyridyl), (IC-142,3-thienyl,6-isopropyloxy-3-pyridyl), (IC-143,5-oxazolyl,6-isopropyloxy-3-pyridyl), (IC-144,F,6-isopropyloxy-3-pyridyl), (IC-145,OPh,6-isopropyloxy-3-pyridyl), (IC-146,CN,6-isopropyloxy-3-pyridyl), (IC-147,NO2,6-isopropyloxy-3-pyridyl), (IC-148,CONH2,6-isopropyloxy-3-pyridyl), (IC-149,CONHn-Pr,6-isopropyloxy-3-pyridyl), (IC-150,CONHPh,6-isopropyloxy-3-pyridyl), (IC-151,NHCOOM e,6-isopropyloxy-3-pyridyl), (IC-152,NHCOOi-Pr,6-isopropyloxy-3-pyridyl), (IC-153,NHCO(3-pyridyl),(6-isopropyloxy-3-pyridyl), (IC-154,NHCO(2-furyl), (6-isopropyloxy-3-pyridyl), (IC-155,3-methyloxyphenyl,6-isopropyloxy-3-pyridyl), (IC-156,4-methyloxyphenyl,6-isopropyloxy-3-pyridyl), (IC-157,4-cyanophenyl,6-isopropyloxy-3-pyridyl), (IC-158,4-oxazolyl,6-isopropyloxy-3-pyridyl), (IC-159,5-Me-2-oxazolyl,6-isopropyloxy-3-pyridyl), (IC-160,3,4-oxadiazol-2-yl,6-isopropyloxy-3-pyridyl), (IC-161,5-Me-3,4-oxadiazol-2-yl,6-isopropyloxy-3-pyridyl), (IC-162,3,4-thiadiazol-2-yl,6-isopropyloxy-3-pyridyl), (IC-163,5-Me-3,4-thiadiazol-2-yl,6-isopropyloxy-3-pyridyl), (IC-164,4-pyridyl,6-isopropyloxy-3-pyridyl), (IC-165,4-methyloxy-3-pyridyl,6-isopropyloxy-3-pyridyl), (IC-166,CONHNH2,6-isopropyloxy-3-pyridyl), (IC-167,1-pyrazolyl,6-isopropyloxy-3-pyridyl), (IC-168,3,4-methylenedioxyphenyl,6-isopropyloxy-3-pyridyl), (IC-169,CONH(cyclopropyl), (6-isopropyloxy-3-pyridyl), (IC-170,NHCO(4-isoxazolyl), (6-isopropyloxy-3-pyridyl), (IC-171,NHCO(5-Me-isoxazol-3-yl), (6-isopropyloxy-3-pyridyl),(IC-172,CF3,6-isopropyloxy-3-pyridyl), (IC-173,3-methyloxypropargyl,6-isopropyloxy-3-pyridyl), (IC-174,2-methyloxyethyloxy,6-isopropyloxy-3-pyridyl), (IC-175, benzyloxy,6-isopropyloxy-3-pyridyl), (IC-176,3-furylmethyloxy,6-isopropyloxy-3-pyridyl), (IC-177,2-oxopyrrolidino,6-isopropyloxy-3-pyridyl).

Test Example 1

DP Inhibitory Activity In Vitro

1) Preparation of Platelet and a Method of cAMP Assay 30 ml of peripheral blood was collected from a healthy volunteer using a syringe containing one ninth amount of 3.8% sodium citrate for diagnosis. After being centrifuged at 180 g for 10 minutes at room temperature, a supernatant was collected and used as Platelet Rich Plasma (PRP). The resulting PRP was washed with wash buffer and centrifuged three times (Washed Platelet: WP) and platelets were counted by a microcell counter. WP was added to a plate in amount of $1.5 \times 10^8$/assay and the plate was treated with 3-isobutyl-1-methylxanthin (IBMX; 0.5 mM) for 5 minutes. A reaction was initiated by adding 100 nM of $PGD_2$ 5 min after an addition of a test compound. The reaction was terminated with an addition of 1N hydrochloric acid after 2 minutes and the cells were destructed using 12% triton X-100. An amount of cAMP in the supernatant was assayed by Homogeneous Trangient Fluorescence (HTRF)

2) Receptor Binding Assay

A prepared WP was homogenated and a membrane fraction was collected with high-speed centrifugation. A compound of the present invention or a reference compound A (No. IC-73 in WO 2003/097598) was added to the plate and $[^3H]$-$PGD_2$ was also added. A platelet membrane, a protein concentration is 2 mg/mL, was added and mixed in the plate, and placed on ice for 2 hours. The reaction solution was transferred to a low protein-adsorptive filter and washed with a wash solution eight times using a cell harvester. After the final washing, water was removed sufficiently, and microscint was added. DP inhibitory activity was investigated by measuring $[^3H]$ by using Micro Beta.

50% DP-inhibitory concentrations (IC50) in the cAMP assay and Ki values in the receptor binding assay were shown in Table 29.

3) Prostanoid Agonist and Antagonist Assay

Agonistic and antagonistic activities of the compounds of the present invention were evaluated based on intracellular calcium flux or cAMP-production as an indicator using HEK 293 cells expressing human EP1, EP2, EP3, EP4, FP, TP and IP respectively. Any compounds did not show an agonistic activity against each prostanoid. In the other hand, more than twenty times potent antagonistic activity ($IC_{50}$) was found in every compound compared with $IC_{50}$ of cAMP assay with WP.

[Table 38]

| compound No. | $IC_{50}$ (nM) | Ki (nM) |
|---|---|---|
| I-1 | 0.58 | 1.0 |
| I-6 | 0.93 | 1.0 |
| I-12 | 1.6 | 0.91 |
| I-13 | 0.51 | 0.85 |
| I-14 | 0.33 | 0.61 |
| I-16 | 0.64 | |
| I-17 | 0.88 | 0.25 |
| Reference Compound A | 23 | |
| I-19 | 2.2 | |
| I-20 | 0.64 | 0.48 |
| I-21 | 1.9 | 0.51 |
| I-25 | 1.1 | |
| I-26 | 1.7 | |
| I-29 | 1.5 | |
| I-31 | 1.7 | |

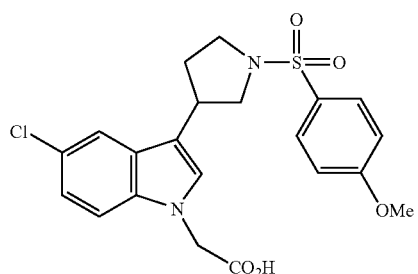

Reference Compound A

Test Example 2

Test Using OVA Asthma Model of Rat

Brown Norway (BN) Rats were sensitized by i.p. administration of 0.1 mg/mL of ovalbumin (OVA) and 1 mg of aluminum hydroxide gel. A solution of 1% OVA was aerosolized by ultrasonic nebulizer (NE-U17) and the rats were subjected to inhalation exposure of the aerosol for 30 minutes in an exposing chamber 12, 19, 26 and 33 days after the sensitization. One hour before the 4th exposure of the antigen, compounds of the present invention were administered in a dose of 10 mg/kg p.o. once a day for three days consecutively. In a control group, 0.5% of methyl cellulose was administered in place of the compound of the present invention.

Under pentobarbital anesthesia (80 mg/kg, i.p.), acetylcholine (3.9, 7.8, 15.6, 31.3, 62.5, 125, 250 and 500 μg/kg) was injected to jugular vein of the rats successively from a lower dose at intervals of 5 minutes three days after the fourth exposure to the antigen, and immediate contractile reaction of airways (an increase of insufflation pressure) was measured by a modified method of Konnzett & Rössler. Inhibition rate of increased hyperresponsive airway against the control group was calculated based on area under curve (AUC) obtained from concentration-response curve of acetylcholine.

After the measurement of increased hyperresponsive airway was completed, bronchoalveoli of the rats were washed with 5 mL of saline three times. Total cell number in the washings was counted by a hemacytometer under light microscope, and inhibition rates of infiltration of inflammatory cells against the control group were calculated. Further, muchin in the airway lavage fluid was measured by ELIZA method using jacalin, a muchin-binding lectin, and the inhibition rates of mucus-secretion against the control group were calculated.

Results were shown in Table 39.

TABLE 39

| compound No. | dose (mg/kg) | inhibition rate (%) | | |
|---|---|---|---|---|
| | | increased hyperresponsive airway | infiltration of inflammatory cells | mucus-secretion |
| I-1 | 10 | 55 | 63 | 68 |
| I-6 | 10 | 69 | 60 | 77 |
| I-12 | 10 | 64 | 48 | 55 |
| I-13 | 10 | 58 | 62 | 44 |
| I-14 | 10 | 84 | 68 | 88 |

Test Example 3

Test Using Nasal Congestion Model of Guinea Pig

Methods of measuring nasal airway resistance and evaluating anti-nasal congestion activity using a rat were illustrated below.

A 1% solution of ovalbumin (OVA) was aerosolized by ultrasonic nebulizer, a male Hartley guinea pigs was sensitized by inhalation of the aerosol for 10 minutes twice at an interval of a week and a reaction was initiated by exposure to the antigen 7 days later. Trachea of the guinea pig was incised under pentobarbital anesthesia (30 mg/kg, i.p.), and cannulae were fitted at the sides of nasal cavity and lung respectively. To the lung side, a ventilator supplying 4 mL of air every time at a rate of 60 times/min was connected. Spontaneous breathing of the guinea pig was stopped by the administration of gallamine (2 mg/kg, i.v.) and 4 mL of air every time was supplied at a rate of 70 times/minute to rostrum of nose through the cannula of the nasal side using a ventilator. Air pressure necessary for supplying the air was measured by a transducer fitted at the side branch and used as an indicator for resistance of nasal cavity. Exposure to the antigen was performed by generating the aerosol of 3% OVA solution between the ventilator and the nasal cavity cannula for three minutes. Compounds of the present invention were administered intravenously 10 minutes before the exposure to the antigen. Resistance of nasal cavity was continuously measured during a period from 0 to 30 minutes, and the inhibition rate against the vehicle was obtained based on AUC of the 30 minutes, which was recorded with resistance of nasal cavity (cm $H_2O$) as a longitudinal axis, and time (from 0 to 30 min.) as an abscissa axis.

FORMULATION EXAMPLE

The following formulating examples are just for illustrative purposes and not intended to limit the range of the present invention. A term of "active ingredient" means the compounds of the present invention, pharmaceutically acceptable salt or hydrate thereof.

Formulation Example 1

A hard-gelatin capsule is prepared with the following ingredients;

| | Amount (mg/capsule) |
|---|---|
| active ingredient | 250 |
| starch (dried) | 200 |
| magnesium stearate | 10 |
| Total | 460 mg |

Formulation Example 2

A tablet is prepared with the following ingredients;

| | Amount (mg/tablet) |
|---|---|
| active ingredient | 250 |
| cellulose(micro crystalline) | 400 |
| silicon dioxide (fume) | 10 |
| stearic acid | 5 |
| Total | 665 mg |

The ingredients above are mixed and compressed to give a tablet weighing 665 mg/tablet.

Formulation Example 3

An aerosol solution is prepared with the following ingredients;

|  | weight |
| --- | --- |
| active ingredient | 0.25 |
| ethanol | 25.75 |
| propellant 22(chlorodifluoroethane) | 74.00 |
| Total | 100.00 |

The active ingredient and ethanol are mixed and the mixture is added to a part of propellant 22, and the resulting solution is transferred to a filling apparatus after being cooled to −30° C. Next, the necessary amount is provided to a stainless-steel vessel and the content is diluted with the remaining propellant. A valve unit is fitted to the vessel.

Formulation Example 4

A tablet containing 60 mg of an active ingredient is prepared as follows;

| active ingredient | 60 mg |
| --- | --- |
| starch | 45 mg |
| macrocrystalline cellulose | 35 mg |
| polyvinylpyrrolidone (10% aq. solution) | 4 mg |
| sodium carboxymethylstarch | 4.5 mg |
| magnesium stearate | 0.5 mg |
| talc | 1 mg |
| Total | 150 mg |

The active ingredient, starch and cellulose are put through a sieve of No. 45 mesh US and mixed sufficiently. The resulting powder is mixed with a solution containing polyvinylpyrrolidone and the mixture is put through a sieve of No. 14 mesh US. The granulated powder is dried at 50° C. and put through a sieve of No. 18 mesh US. Sodium carboxymethylstarch, magnesium stearate and talc are put through a sieve of No. 60 mesh US in advance and added to the granulated powder, mixed and compressed by a tableting machine to give a tablet weighing 150 mg/tablet.

Formulation Example 5

A capsule containing 80 mg of an active ingredient is prepared as follows;

| active ingredient | 80 mg |
| --- | --- |
| starch | 59 mg |
| microcrystalline cellulose | 59 mg |
| magnesium stearate | 2 mg |
| Total | 200 mg |

The active ingredient, starch, cellulose and magnesium stearate are mixed, put through a sieve of No. 45 mesh US and filled in hard-gelatin capsules to give a capsule formulation containing 200 mg/capsule.

Formulation Example 6

A suppository containing 225 mg of an active ingredient is prepared as follows;

| active ingredient | 225 mg |
| --- | --- |
| saturated fatty acid gliceride | 2000 mg |
| Total | 2225 mg |

The active ingredient is put through a sieve of No. 60 mesh US and suspended in the saturated fatty acid glyceride melted by the least amount of heating. Then, the mixture was cooled in a mold of 2 g in appearance.

Formulation Example 7

A suspension containing 50 mg of an active ingredient is prepared as follows;

| active ingredient | 50 mg |
| --- | --- |
| sodium carboxymethylcellulose | 50 mg |
| syrup | 1.25 ml |
| solution of benzoic acid | 0.10 ml |
| flavor | q.v. |
| pigment | q.v. |
| Total (adding purified water) | 5 ml |

The active ingredient is put through a sieve of No. 45 mesh US and mixed with sodium carboxymethylcellulose and syrup to give a smooth paste. The solution of benzoic acid and flavor are diluted with a part of water and added to the paste and stirred. A necessary amount of water is added to give the objective suspension.

Formulation Example 8

A formulation for i.v. injection is prepared as follows;

| active ingredient | 100 mg |
| --- | --- |
| saturated fatty acid gliceride | 1000 ml |

The solution containing the active ingredient above is usually injected intravenously to a patient at a rate of 1 ml/min.

INDUSTRIAL APPLICABILITY

It was found that a novel indole derivative had a DP receptor antagonistic activity and was effective on treating allergic diseases.

The invention claimed is:

1. A compound of the general formula (II):

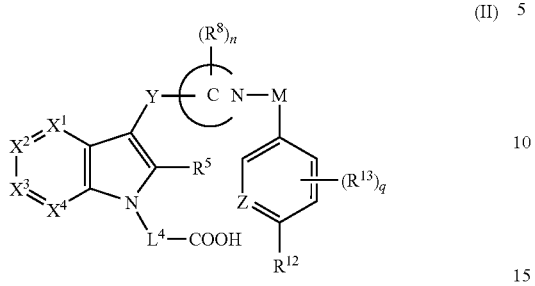

wherein the ring C is a formula of

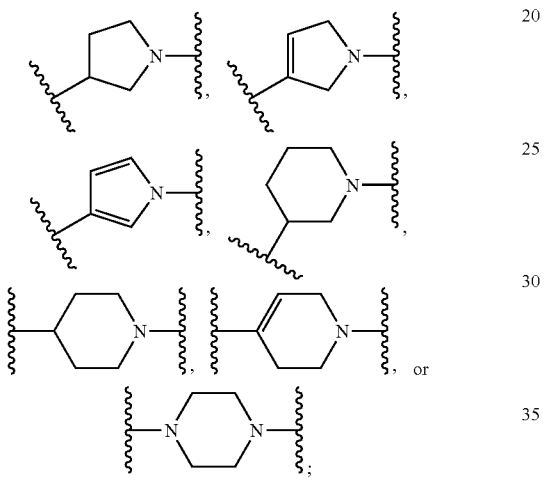

the formula of —$X^1$=$X^2$—$X^3$=$X^4$— is a formula of ᵥ—C($R^1$)=C($R^2$)—C($R^3$)=N—;

$R^1$, $R^2$, $R^3$ and $R^5$ are independently a hydrogen atom, halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfonyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, optionally substituted sulfamoyl, cyano, nitro, optionally substituted aryl, optionally substituted aryloxy, optionally substituted arylthio, optionally substituted arylsulfonyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or optionally substituted non-aromatic heterocyclic group;

$R^{12}$ is optionally substituted C1-C6 alkyloxy, optionally substituted C2-C6 alkenyloxy, optionally substituted C2-C6 alkynyloxy, optionally substituted C1-C6 alkylthio, optionally substituted C2-C6 alkenylthio, optionally substituted C2-C6 alkynylthio, optionally substituted C3-C6 cycloalkyloxy, optionally substituted C3-C6 cycloalkylthio, optionally substituted aryloxy or optionally substituted arylthio;

$R^{13}$ is independently a halogen atom, optionally substituted alkyl, optionally substituted cycloalkyl, optionally substituted amino, acyl, optionally substituted alkyloxycarbonyl, optionally substituted carbamoyl, optionally substituted sulfamoyl, cyano, nitro, optionally substituted aryl, optionally substituted arylsulfonyloxy, optionally substituted heteroaryl or optionally substituted non-aromatic heterocyclic group;

$R^{14}$ is independently optionally substituted alkyl, optionally substituted alkenyl, optionally substituted alkynyl, oxo, optionally substituted aryl, optionally substituted heteroaryl, or optionally substituted non-aromatic heterocyclic group;

M is carbonyl or sulfoyl;

Y and $L^4$ are independently a single bond or optionally substituted alkylene optionally containing one or two heteroatom(s);

Z is CH, C($R^{13}$) or N;

n is 0, 1 or 2; and q is 0, 1, 2 or 3;

or a pharmaceutically acceptable salt thereof.

2. A compound of the general formula (III):

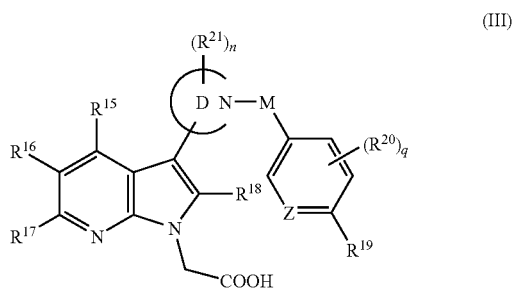

wherein the ring D is a formula of

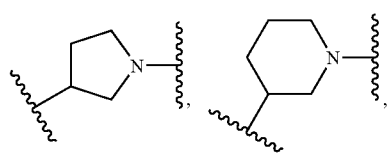

-continued

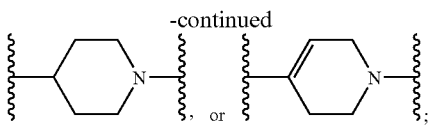

$R^{15}$, $R^{16}$ and $R^{18}$ are independently a hydrogen atom, a halogen atom, optionally substituted alkyl, optionally substituted alkyloxy, optionally substituted alkylthio, optionally substituted alkylsulfinyl, optionally substituted alkylsulfonyl, optionally substituted amino, cyano, nitro, optionally substituted aryl, optionally substituted heteroaryl or optionally substituted non-aromatic heterocyclic group;

$R^{17}$ is independently a hydrogen atom, a halogen atom, optionally substituted alkyl, optionally substituted alkenyl, optionally substituted alkynyl, optionally substituted cyloalkyl, optionally substituted cyloalkenyl, hydroxy, optionally substituted alkyloxy, optionally substituted alkenyloxy, optionally substituted alkynyloxy, mercapto, optionally substituted alkylthio, optionally substituted alkenylthio, optionally substituted alkynylthio, optionally substituted alkylsulfinyl, optionally substituted alkynylsulfonyl, optionally substituted alkynylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, optionally substituted sulfamoyl, cyano, nitro, optionally substituted aryl, optionally substituted aryloxy, optionally substituted arylthio, optionally substituted arylsulfonyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group;

$R^{19}$ is optionally substituted C1-C6 alkyloxy, optionally substituted C2-C6 alkenyloxy, optionally substituted C2-C6 alkynyloxy, optionally substituted C1-C6 alkylthio, optionally substituted C2-C6 alkenylthio, optionally substituted C2-C6 alkynylthio, optionally substituted C3-C6 cycloalkyloxy, optionally substituted C3-C6 cycloalkylthio, optionally substituted aryloxy or optionally substituted arylthio;

$R^{20}$ is independently a halogen atom, optionally substituted alkyl, optionally substituted cyloalkyl, optionally substituted amino, acyl, optionally substituted alkyloxycarbonyl, optionally substituted carbamoyl, optionally substituted sulfamoyl, cyano, nitro, optionally substituted aryl, optionally substituted arylsulfonyloxy, optionally substituted heteroaryl or an optionally substituted non-aromatic heterocyclic group;

$R^{21}$ is independently optionally substituted alkyl, optionally substituted alkenyl, optionally substituted alkynyl, oxo, optionally substituted aryl, optionally substituted heteroaryl, or an optionally substituted non-aromatic heterocyclic group;

M is carbonyl or sulfonyl;

Z is CH, C($R^{20}$), or N;

n is 0, 1 or 2 and q is 0, 1, 2 or 3;

or a pharmaceutically acceptable salt thereof.

3. A compound of claim 2 wherein $R^{17}$ is a hydrogen atom, a halogen atom, optionally substituted alkyl, optionally substituted alkyloxy, optionally substituted amino, optionally substituted carbamoyl, optionally substituted aryl, optionally substituted heteroaryl or an optionally substituted non-aromatic heterocyclic ring;

or a pharmaceutically acceptable salt thereof.

4. A compound of claim 2 wherein $R^{15}$, $R^{16}$ and $R^{18}$ are hydrogen atoms, or a pharmaceutically acceptable salt thereof.

5. A compound of claim 2 wherein $R^{19}$ is optionally substituted C1-C6 alkyl or optionally substituted C1-C6 alkylthio, or a pharmaceutically acceptable salt thereof.

6. A compound of claim 2 wherein $R^{20}$ is a halogen atom, optionally substituted alkyl or optionally substituted alkyloxy, and q is 0 or 1, or a pharmaceutically acceptable salt thereof.

7. A compound of claim 2 wherein M is sulfonyl, or a pharmaceutically acceptable salt thereof.

8. A compound of any of claim 2-7 wherein $R^{21}$ is alkyl or oxo, and n is 0, or a pharmaceutically acceptable salt thereof.

9. A pharmaceutical composition comprising the compound or claim 1 or 2, or a pharmaceutically acceptable salt thereof, and a pharmaceutically acceptable carrier.

10. A method for inhibiting DP receptor which comprises administering the compound of claim 1 or 2, or a pharmaceutically acceptable salt thereof, to a patient in need thereof.

11. A method of treating asthma which comprises administering the compound of claim 1 or 2, or a pharmaceutically acceptable salt thereof, to a patient in need thereof.

* * * * *

UNITED STATES PATENT AND TRADEMARK OFFICE
CERTIFICATE OF CORRECTION

PATENT NO.        : 7,842,692 B2
APPLICATION NO.   : 11/989132
DATED             : November 30, 2010
INVENTOR(S)       : Akira Kugimiya et al.

It is certified that error appears in the above-identified patent and that said Letters Patent is hereby corrected as shown below:

On the first page, item (75), delete "; Naohiro Onodera, Osaka (JP)".

Signed and Sealed this
Thirtieth Day of August, 2011

David J. Kappos
*Director of the United States Patent and Trademark Office*